US009446175B2

(12) United States Patent
Breuer et al.

(10) Patent No.: US 9,446,175 B2
(45) Date of Patent: Sep. 20, 2016

(54) COMPOSITIONS AND METHODS FOR TREATING AND PREVENTING NEOINTIMAL STENOSIS

(75) Inventors: Christopher Breuer, New Albany, OH (US); Tarek Fahmy, New Haven, CT (US); Michael Simons, Hamden, CT (US); Pei-Yu Chen, East Haven, CT (US); Daniel Rowe Duncan, Boston, MA (US); Joseph Patterson, New Haven, CT (US)

(73) Assignee: Yale University, New Haven, CT (US)

( * ) Notice: Subject to any disclaimer, the term of this patent is extended or adjusted under 35 U.S.C. 154(b) by 12 days.

(21) Appl. No.: 14/123,728

(22) PCT Filed: Jun. 4, 2012

(86) PCT No.: PCT/US2012/040759
§ 371 (c)(1),
(2), (4) Date: Jun. 16, 2014

(87) PCT Pub. No.: WO2012/167261
PCT Pub. Date: Dec. 6, 2012

(65) Prior Publication Data
US 2014/0348889 A1  Nov. 27, 2014

Related U.S. Application Data

(60) Provisional application No. 61/520,040, filed on Jun. 3, 2011, provisional application No. 61/494,683, filed on Jun. 8, 2011, provisional application No. 61/555,712, filed on Nov. 4, 2011.

(51) Int. Cl.

| | | |
|---|---|---|
| *A61K 48/00* | (2006.01) | |
| *C07H 21/02* | (2006.01) | |
| *C07H 21/04* | (2006.01) | |
| *A61L 31/16* | (2006.01) | |
| *A61K 31/4178* | (2006.01) | |
| *A61L 27/50* | (2006.01) | |
| *A61L 27/54* | (2006.01) | |
| *A61K 45/06* | (2006.01) | |
| *A61K 31/4439* | (2006.01) | |
| *A61K 31/444* | (2006.01) | |
| *A61K 31/4709* | (2006.01) | |
| *A61K 31/498* | (2006.01) | |
| *A61K 38/18* | (2006.01) | |
| *A61L 31/06* | (2006.01) | |
| *A61L 31/14* | (2006.01) | |
| *C07K 16/28* | (2006.01) | |
| *C12N 15/113* | (2010.01) | |
| *A61K 39/00* | (2006.01) | |

(52) U.S. Cl.
CPC ............ *A61L 31/16* (2013.01); *A61K 31/4178* (2013.01); *A61K 31/444* (2013.01); *A61K 31/4439* (2013.01); *A61K 31/4709* (2013.01); *A61K 31/498* (2013.01); *A61K 38/1825* (2013.01); *A61K 45/06* (2013.01); *A61L 27/507* (2013.01); *A61L 27/54* (2013.01); *A61L 31/06* (2013.01); *A61L 31/14* (2013.01); *C07K 16/2863* (2013.01); *C12N 15/113* (2013.01); *A61K 2039/505* (2013.01); *A61L 2300/204* (2013.01); *A61L 2300/25* (2013.01); *A61L 2300/258* (2013.01); *A61L 2300/432* (2013.01); *A61L 2300/61* (2013.01); *A61L 2300/622* (2013.01)

(58) Field of Classification Search
CPC ............................. A61K 48/00; C12N 15/113
See application file for complete search history.

(56) References Cited

U.S. PATENT DOCUMENTS

| | | |
|---|---|---|
| 2004/0063654 A1 | 4/2004 | Davis |
| 2005/0124534 A1 | 6/2005 | Noble |
| 2006/0045905 A1 | 3/2006 | Ozeki |
| 2006/0217437 A1 | 9/2006 | Burmester |
| 2009/0069368 A1 | 3/2009 | Bono |

FOREIGN PATENT DOCUMENTS

| | | |
|---|---|---|
| WO | 0012497 | 3/2000 |
| WO | 0061578 | 10/2000 |
| WO | 2004016606 | 2/2004 |
| WO | 2004050659 | 6/2004 |
| WO | 2004080982 | 9/2004 |
| WO | 2004112710 | 12/2004 |
| WO | 2005013915 | 2/2005 |

(Continued)

OTHER PUBLICATIONS

Costa and Simon, "Molecular basis of restenosis and drug-eluting stents", Circulation., 111(17):2257-73 (2005).

(Continued)

*Primary Examiner* — Amy Bowman
(74) *Attorney, Agent, or Firm* — Pabst Patent Group LLP

(57) ABSTRACT

Methods for treating or preventing neointima stenosis are disclosed. The methods generally involve the use of a TGFβ inhibitor, a SMAD2 inhibitor, an FGF Receptor agonist, a Let-7 agonist, or a combination thereof, to inhibit endothelial-to-mesenchymal transition (Endo-MT) of vascular endothelial cells into smooth muscle cells (SMC) at sites of endothelial damage. The disclosed methods can therefore be used to prevent or inhibit neointimal stenosis or restenosis, e.g., after angioplasty, vascular graft, or stent. Also disclosed are methods for increasing the patency of biodegradable, synthetic vascular grafts using a composition that inhibits Endo-MT. A cell-free tissue engineered vascular graft (TEVG) produced by this method is also disclosed.

19 Claims, 27 Drawing Sheets

(56) References Cited

FOREIGN PATENT DOCUMENTS

| | | |
|---|---|---|
| WO | 2006026306 | 3/2006 |
| WO | 2008047198 | 4/2008 |

OTHER PUBLICATIONS

Duncan, et al., "Challenges in translating vascular tissue engineering to the pediatric clinic", Vasc. Cell, 3(1):23 (2011).

Fahmy, et al., "Surface modification of biodegradable polyesters with fatty acid conjugates for improved drug targeting", Biomaterials 26:5727-36 (2005).

Fu, et al., "SM16, an orally active TGF-beta type I receptor inhibitor prevents myofibroblast induction and vascular fibrosis in the rat carotid injury model", Arterioscler Thromb Vasc Biol., 28(4):665-71 (2008).

Gotoh, et al., "Tyrosine phosphorylation sites on FRS2alpha responsible for Shp2 recruitment are critical for induction of lens and retina", PNAS, 101(49):17144-9 (2004).

Itoh and Ornitz, et al., "Evolution of the Fgf and Fgfr gene families", Trends in Genet., 20(11):563-9 (2004).

Khurana, et al., "Angiogenesis-dependent and independent phases of intimal hyperplasia", Circulation., 110(16):2436-43 (2004).

Lin, et al., "Generation of an Frs2alpha conditional null allele", Genesis. 45(9):554-9 (2007).

Malavaud, et al., "Direct FGF receptor 1 activation through an anti-idiotypic strategy mimicks the biological activity of FGF-2 and inhibits the progression of the bladder carcinoma derived from NBT-II cells", Oncogene, 23:6769-78 (2004).

Mood, et al., "SNT1/FRS2 mediates germinal vesicle breakdown induced by an activated FGF receptor1 in Xenopus oocytes", J Biol Chem., 277(36):33196-204 (2002).

Murakami, et al., "The FGF system has a key role in regulating vascular integrity", J Clin Invest. 118(10):3355-66 (2008).

Ohtani, et al., "Blockade of vascular endothelial growth factor suppresses experimental restenosis after intraluminal injury by inhibiting recruitment of monocyte lineage cells", Circulation., 110(16):2444-52 (2004).

Park, et al., "EW-7203, a novel small molecule inhibitor of transforming growth factor-$\beta$ (TGF-$\beta$) type I receptor/activin receptor-like kinase-5, blocks TGF-$\beta$1-mediated epithelial-to-mesenchymal transition in mammary epithelial cells", Cancer Sci., 102(10)1889-96 (2011).

Partovian, et al., "Syndecan-4 regulates subcellular localization of mTOR Complex2 and Akt activation in a PKCalpha-dependent manner in endothelial cells", Mol Cell, 32(1):140-9 (2008).

Poh, et al., "Blood vessels engineered from human cells", Lancet, 365:2122-4 (2005).

Robinson, et al., "A constitutively active and nuclear form of the MAP kinase ERK2 is sufficient for neurite outgrowth and cell transformation", Curr Biol., 8(21):1141-50 (1998).

Roh, et al., "Small-diameter biodegradable scaffolds for functional vascular tissue engineering in the mouse model", Biomaterials. 29(10):1454-63 (2008).

Roh, et al., "Tissue-engineered vascular grafts transform into mature blood vessels via an inflammation-mediated process of vascular remodeling", PNAS, 107:4669-74 (2010).

Solan and Niklason, et al., "Age effects on vascular smooth muscle: an engineered tissue approach", Cell Transplant., 14(7):481-8 (2005).

Viswanathan and Daley, "Lin28: A microRNA regulator with a macro role", Cell, 140(4):445-9 (2010).

Watabe, et al., "TGF-beta receptor kinase inhibitor enhances growth and integrity of embryonic stem cell-derived endothelial cells", J. Cell Biol., 163:1303-11 (2003).

Wolf, et al., "Antibodies against transforming growth factor-beta-1 suppress intimal hyperplasia in a rat model", Clinical Investigation, 93(3):1172-8 (1994).

(75-82): site 1
SEQ ID NO:99  5'...GGGAGGUCAAUUGUUCUACCUCA...-3'
              | | |         | | | | | |
SEQ ID NO:91  3' UUGGUGUGUUGGAU–GAUGGAGU  5'

(3889-3895): site 2
SEQ ID NO:100 5'...AGACCAAGGUACAUUUACCUCAU...-3'
                              | | | | | |
SEQ ID NO:91  3' UUGGUGUGUUGGAUGAUGGAGU  5'

(3771-3777): site 1
SEQ ID NO:101 5'...ACCCAGUUGGUUUCUCUACCUCU...-3'
                              | | | | | |
SEQ ID NO:91  3' UUGGUGUGUUGGAUGAUGGAGU  5'

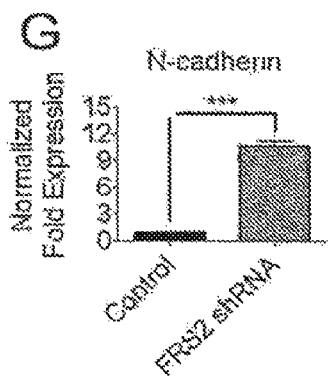
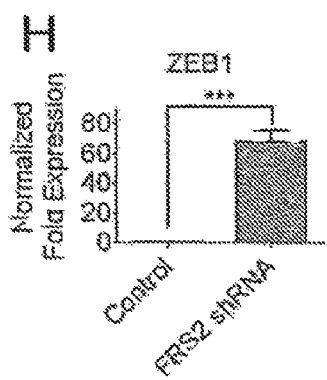
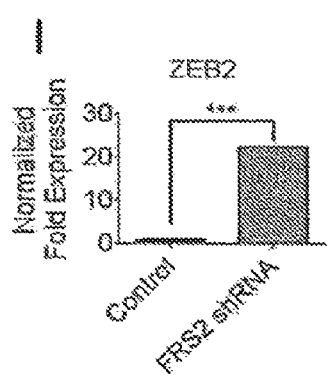
FIG. 11GFIG. 11HFIG. 11I
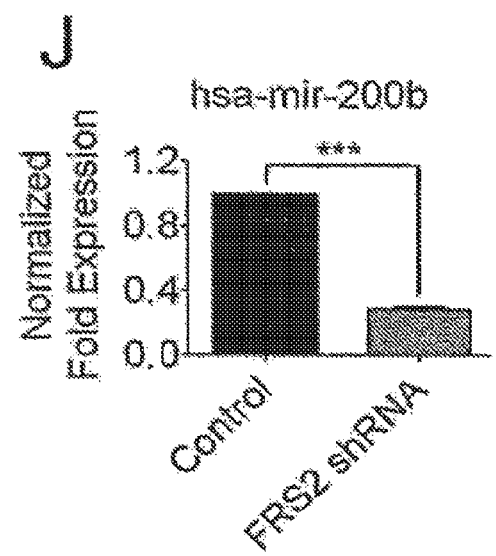
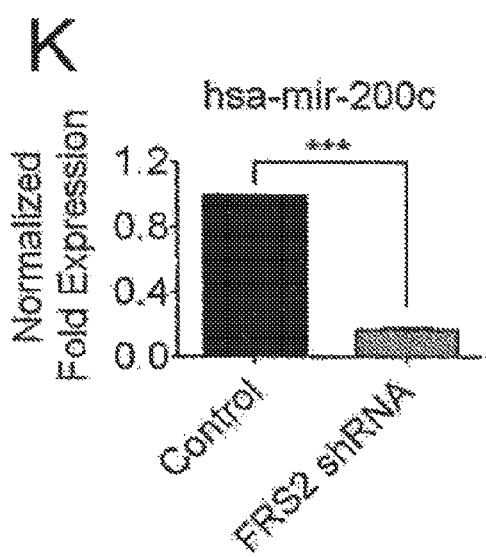
FIG. 11JFIG. 11K

COMPOSITIONS AND METHODS FOR TREATING AND PREVENTING NEOINTIMAL STENOSIS

CROSS REFERENCE TO RELATED APPLICATIONS

This application is a 371 application of the International Application No. PCT/US2012/040759 entitled "Compositions and Methods for Treating and Preventing Neointimal Stenosis", filed in the United States Receiving Office for the PCT on Jun. 4, 2012, which claims the benefit of and priority to U.S. Provisional Application No. 61/520,040 filed Jun. 3, 2011, U.S. Provisional Application No. 61/494,683, filed Jun. 8, 2011, and U.S. Provisional Application No. 61/555,712, filed Nov. 4, 2011, which are hereby incorporated herein by reference in their entirety.

REFERENCE TO SEQUENCE LISTING

The Sequence Listing submitted Dec. 3, 2013 as a text file named "YU_5546_5658_5689_ST25.txt," created on Dec. 3, 2013, and having a size of 22,666 bytes is hereby incorporated by reference pursuant to 37 C.F.R. §1.52(e)(5).

STATEMENT REGARDING FEDERALLY SPONSORED RESEARCH OR DEVELOPMENT

This invention was made with government support under Agreement Nos. AR046032, R01-HL 053793 and R01-HL 098228 by the National Institutes of Health. The government has certain rights in the invention.

FIELD OF THE INVENTION

The invention is generally related to the field of vascular stenosis and restenosis, more particularly to compositions and methods for the prevention and treatment of neointimal hyperplasia or the formation of tissue engineered vascular graft stenosis.

BACKGROUND OF THE INVENTION

Intimal or Neointima formation underlies a number of common vascular diseases, including vascular graft stenosis and restenosis after an angioplasty or stent. Despite decades of investigations, the origin of neointima still remains controversial with studies variously pointing to the role of medial smooth muscle cell (SMC) proliferation (Costa M A and Simon D I. *Circulation.* 111(17):2257 (2005)), vessel wall inflammation (Ohtani K, et al. *Circulation.* 110(16):2444 (2004)) and adventitial angiogenesis (Khurana R, et al. *Circulation.* 110(16):2436 (2004)).

Neointimal stenosis followed by thrombosis is the major cause of synthetic vascular graft failure. Tissue engineered vascular grafts (TEVGs) offer many advantages to these synthetic grafts, but also have limitations of their own. TEVGs are typically prepared by seeding autologous cells onto a biodegradable polymeric tubular scaffold. The scaffold degrades by hydrolysis, ultimately leaving only the living vessel in the patient.

The methodology of seeding synthetic vascular grafts with autologous cells, however, is still problematic for many reasons. First, it requires an invasive procedure (biopsy) in addition to the need for a substantial period of time in order to expand the cells in culture that limited its clinical utility. This approach also faces the inherent difficulty in obtaining healthy autologous cells from diseased donors (Poh, et al., *Lancet,* 365:2122-24 (2005); Solan, et al., *Cell Transplant.,* 14(7):481-8 (2005)). The use of cell culture also results in an increased risk of contamination and even the potential for dedifferentiation of the cultured cells. The use of autologous cells to seed the polymeric grafts also limits the off-the-shelf availability of tissue engineered vascular grafts, thereby limiting their overall clinical utility. TEVGs that do not require cell seeding would offer many therapeutic, economic, and safety advantages.

It is an object of the invention to provide compositions and methods for treating and preventing neointimal stenosis.

It is a further object of the invention to provide methods for increasing the patency of biodegradable, synthetic vascular grafts with or without using cell seeding.

It is a further object of the invention to provide a cell-free TEVG with improved patency and reduced graft stenosis.

SUMMARY OF THE INVENTION

The disclosed compositions and methods are based on the discovery that an endothelial-to mesenchymal transition (Endo-MT) of vascular endothelial cells into smooth muscle cells (SMC) contributes to neointimal stenosis. Endo-MT in blood vessels is initiated by transforming growth factor β (TGFβ) signaling. In some embodiments, this TGFβ signaling is through TGFβ receptor I (TGFβRI) and SMAD2. Endo-MT is normally suppressed by ongoing fibroblast growth factor (FGF) signaling, which maintains Let-7 microRNA expression, which in turn prevents the activation of TGFβ, TGFβR1 and SMAD2 expression.

A method for treating or preventing neointimal stenosis by inhibiting or reversing Endo-MT is therefore disclosed. The method generally involves the use of a composition contains a TGFβ inhibitor, a SMAD2 inhibitor, an FGF receptor agonist, a Let-7 agonist, or a combination thereof to inhibit or prevent Endo-MT in blood vessels with damaged endothelium to prevent or inhibit neointimal stenosis. These compositions may be used to inhibit or prevent Endo-MT at the site of potential or actual neointima. For example, in some embodiments, the composition is coated on or incorporated into a vascular device, such as a vascular graft, balloon, or stent prior to administration to a blood vessel of the subject. In other embodiments, the composition is administered directly to the subject, e.g., after administration of a vascular device or after diagnosis of a neointimal stenosis. In these embodiments, the composition is preferably administered locally to the site of actual or potential neointima formation.

Also disclosed are methods for increasing the patency of biodegradable, synthetic vascular grafts by inhibiting Endo-MT. Cell-free tissue engineered vascular graft (TEVG) produced by this method are also disclosed. The methods involve either administering a composition containing a TGFβ inhibitor, a SMAD2 inhibitor, an FGF Receptor agonist, a Let-7 agonist, or a combination thereof either to the subject receiving the TEVG or to the TEVG prior to implantation. The TEVGs are tubular, porous structures that allow for recruitment and integration of host cells into the graft that mediate remodeling and vascular neotissue formation. The TEVGs are biodegradable, which allows for the grafts to be completely replaced by forming neotissue as they degrade.

The disclosed TEVGs do not require cell seeding, avoiding many problems associated with seeding, including the need for an invasive procedure to obtain autologous cells, the need for a substantial period of time in order to expand the cells in culture, the inherent difficulty in obtaining healthy autologous cells from diseased donors, and an increased risk of contamination and the potential for dedifferentiation of the cells. The disclosed cell-free TEVGs therefore have a greater off-the-shelf availability and increased overall clinical utility.

The cell-free TEVGs may be fabricated from biodegradable polymers using any known method. In one embodiment, the polymeric vascular grafts are fabricated from woven or non-woven sheets or felts or polymeric fibers. The polymers and fabrication methods are selected to produce vascular grafts with biomechanical properties, such as initial burst pressure, suture retention strength, elasticity and tensile strength, suitable for use as vascular conduits. Polymeric woven or non-woven sheets or felts may be further treated with polymeric sealants to modify the biomechanical properties of the graft and/or to control the total porosity and pore size distribution range of the vascular graft.

A composition containing a TGTGFβ inhibitor, a SMAD2 inhibitor, an FGF Receptor agonist, a Let-7 agonist, or a combination thereof, may be administered in an effective amount to prevent, inhibit or reduce restenosis, thrombus or aneurysm formation in implanted polymeric vascular grafts. The composition may be administered prior to vascular graft implantation, at the same time as vascular graft implantation, following vascular graft implantation, or any combination thereof. In one embodiment, the composition is administered either locally or systemically from a controlled release formulation.

In a preferred embodiment, the composition is administered locally at the site of graft implantation using a controlled release formulation. In some embodiments, the composition is incorporated into or onto the polymeric vascular graft which functions as a controlled release formulation. The composition may be dispersed evenly throughout the polymeric vascular graft using any known suitable method. In another embodiment, the composition is encapsulated in a second polymeric matrix that is coated on or incorporated into the polymeric vascular graft. In some embodiments, the composition is encapsulated into microspheres, nanospheres, microparticles and/or microcapsules, and seeded into the porous vascular graft.

The cell-free TEVGs may be used as venous, arterial or artero-venous conduits for any vascular or cardiovascular surgical application. Exemplary applications include, but are not limited to, congenital heart surgery, coronary artery bypass surgery, peripheral vascular surgery and angioaccess.

BRIEF DESCRIPTION OF THE DRAWINGS

after transduction with lentivirus vector expressing pre-let-7b (open bars) or pre-let-7c (shaded bars). qRT-PCR was performed for mature let-7 miRNAs.

FIGS. 11A-11I are bar graphs showing qRT-PCR mRNA expression (relative mRNA level) of TGFβR1 (FIG. 11A), TGFβRII (FIG. 11B), Smad2 (FIG. 11C), SM α-actin (FIG. 11D), Fibronectin (FIG. 11E), Vimentin (FIG. 11F), N-cadherin (FIG. 11G), ZEB1 (FIG. 11H), or ZEB2 (FIG. 11I) in control (solid bars) and FRS2 knockdown (shaded bars) primary human mammary epithelial cells. FIGS. 11J-11M are bar graphs showing qRT-PCR miRNA expression (relative mRNA level) of hsa-mir-200b (FIG. 11J), hsa-mir-200c (FIG. 11K), hsa-let-7b (FIG. 11L), hsa-let7c (FIG. 11M) in control (solid bars) and FRS2 knockdown (shaded bars) primary human mammary epithelial cells.

FIG. 14B, bar 3), SB-431542 microparticles (FIG. 14A, bar 2; FIG. 14B, bar 4), control scaffold (FIG. 14D, bar 1), and SB-431542 scaffold (FIG. 14D, bar 2).

DETAILED DESCRIPTION OF THE INVENTION

I. Definitions

Figures 1A, 1B, 1C, 1D, 1E, 1F:
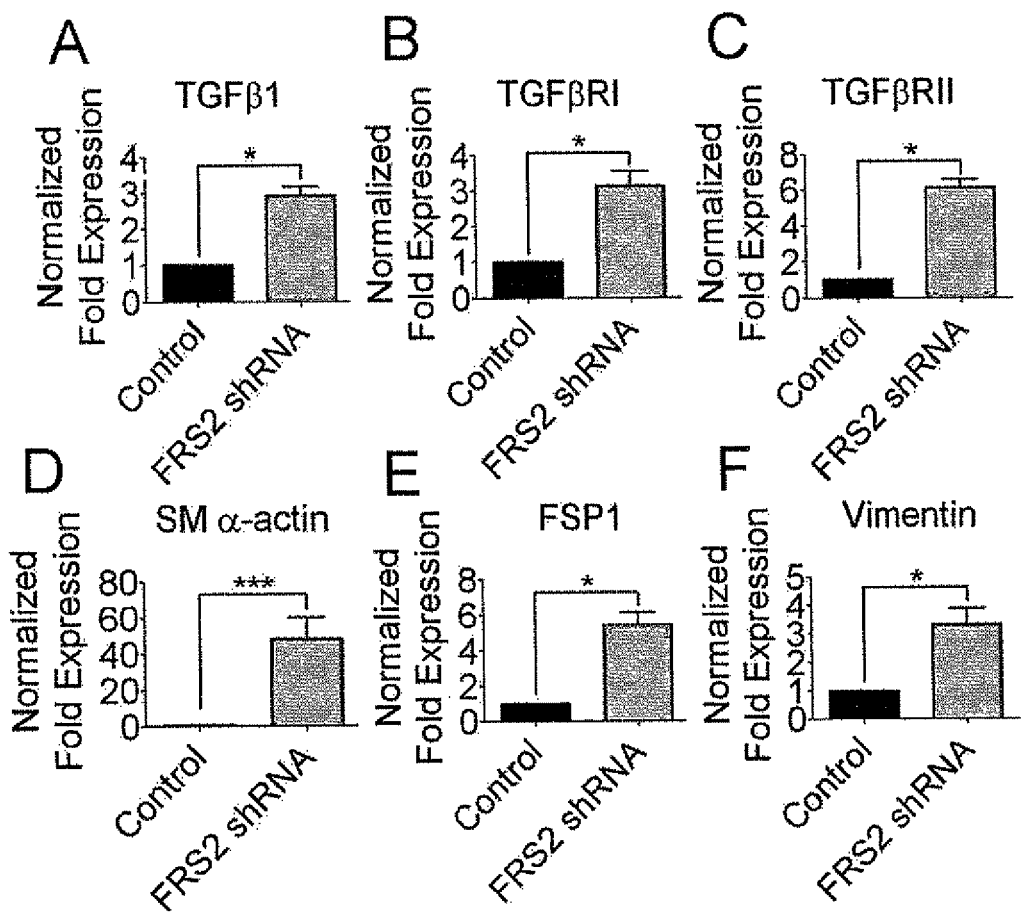
FIGS. 1A-1F are bar graphs showing qRT-PCR mRNA expression (normalized fold expression) of TGFβ1 (FIG. 1A), TGFβRI (FIG. 1B), TGFβRII (FIG. 1C), SM α-actin (FIG. 1D), FSP1 (FIG. 1E), and Vimentin (FIG. 1F) in control (sold bar) and FRS2 knockdown (shaded bar) HUAEC. $*p<0.05$; $***p<0.001$ compared to control.

The term "vascular stenosis" refers to an abnormal narrowing in a blood vessel that occurs following an injury to the vessel wall (endothelium). In some embodiments, stenosis involves a reduction in the circumference of a lumen of 50% or more. The term "restenosis" refers to stenosis at a previously stenotic site. Restenosis, as used herein, encompasses occlusion. Exemplary injuries that result in stenosis or restenosis include trauma to an atherosclerotic lesion (as seen with angioplasty or stent), a resection of a lesion (as seen with endarterectomy), an external trauma (e.g., a cross-clamping injury), or a surgical anastomosis.

The term "neointimal stenosis" refers abnormal narrowing in a blood vessel resulting from neointimal formation.

The term "neointima" refers to a new or thickened layer of intima (inner lining) formed in a blood vessel in response to signals from injured endothelial cells.

The term "TGFβ inhibitor" as used herein refers to a composition that directly inhibits TGFβ or TGFβRI expression, TGFβ or TGFβRI bioavailability, binding of TGFβ to TGFβRI, or the binding of TGFβRI to SMAD2.

The term "SMAD2 inhibitor" as used herein refers to a composition that directly inhibits an activity of SMAD2, such as the phosphorylation of SMAD2 protein by TGFβRI, the translocation of SMAD2 to the nucleus, or the binding of SMAD2 to a DNA substrate.

The term "FGF receptor agonist" refers to a composition that directly promotes FGF signaling through an FGF receptor (FGFR). The agonist may be an FGF protein (e.g., natural or recombinant FGF), an expression vector encoding an FGF protein, or any fragment or variant thereof that activates FGFR signaling.

The term "Let-7 agonist" refers to a composition that promotes one or more activities of a Let-7 microRNA. The agonist may be a Let-7 miRNA or an expression vector encoding one or more Let-7 microRNA.

The term "vascular device" refers to a medical device administered to a blood vessel during a medical procedure. The term covers devices that may damage the vascular wall and cause neointimal stenosis. The term includes vascular grafts, angioplasty balloons, and vascular stents.

The tend "vector" refers to a replicon, such as a plasmid, phage, or cosmid, into which another DNA segment may be inserted so as to bring about the replication of the inserted segment. The vectors can be expression vectors.

The term "expression vector" refers to a vector containing a gene construct in a form suitable for expression by a cell (e.g., operably linked to a transcriptional control element).

The term "operatively linked to" refers to the functional relationship of a nucleic acid with another nucleic acid sequence. Promoters, enhancers, transcriptional and translational stop sites, and other signal sequences are examples of nucleic acid sequences operatively linked to other sequences. For example, operative linkage of DNA to a transcriptional control element refers to the physical and functional relationship between the DNA and promoter such that the transcription of such DNA is initiated from the promoter by an RNA polymerase that specifically recognizes, binds to and transcribes the DNA.

The term "individual," "host," "subject," and "patient" are used interchangeably to refer to any individual who is the target of administration or treatment. The subject can be a vertebrate, for example, a mammal. Thus, the subject can be a human or veterinary patient.

The term "treat" or "treatment" refers to the medical management of a patient with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder.

The term "prevent" does not require absolute forestalling of the condition or disease but can also include a reduction in the onset or severity of the disease or condition. Thus, if a therapy can treat a disease in a subject having symptoms of the disease, it can also prevent that disease in a subject who has yet to suffer some or all of the symptoms.

The term "inhibit" refers to a decrease in an activity, response, condition, disease, or other biological parameter. This can include but is not limited to the complete ablation of the activity, response, condition, or disease. This may also include, for example, a 10% reduction in the activity, response, condition, or disease as compared to the native or control level. Thus, the reduction can be a 10, 20, 30, 40, 50, 60, 70, 80, 90, 100%, or any amount of reduction in between as compared to native or control levels.

The term "therapeutically effective" means that the amount of the composition used is of sufficient quantity to ameliorate one or more causes or symptoms of a disease or disorder. Such amelioration only requires a reduction or alteration, not necessarily elimination.

The term "pharmaceutically acceptable" refers to those compounds, materials, compositions, and/or dosage forms which are, within the scope of sound medical judgment, suitable for use in contact with the tissues of human beings and animals without excessive toxicity, irritation, allergic response, or other problems or complications commensurate with a reasonable benefit/risk ratio.

The term "small molecule" refers to a molecule, such as an organic or organometallic compound, with a molecular weight of less than 2,000 Daltons, more preferably less than 1,500 Daltons, most preferably less than 1,000 Daltons. The small molecule can be a hydrophilic, hydrophobic, or amphiphilic compound.

The term "antibodies" refers to natural or synthetic antibodies that selectively bind a target antigen. The term includes polyclonal and monoclonal antibodies. In addition to intact immunoglobulin molecules, also included in the term "antibodies" are fragments or polymers of those immunoglobulin molecules, and human or humanized versions of immunoglobulin molecules that selectively bind the target antigen.

The term "copolymer" refers to a single polymeric material that is comprised of two or more different monomers. The copolymer can be of any form, such as random, block, graft, etc. The copolymers can have any end-group, including capped or acid end groups.

The term "biocompatible" refers to a material and any metabolites or degradation products thereof that are generally non-toxic to the recipient and do not cause any significant adverse effects to the subject.

The term "biodegradable" refers to a material that will degrade or erode under physiologic conditions to smaller units or chemical species that are capable of being metabolized, eliminated, or excreted by the subject.

The term "controlled release" or "modified release" refers to a release profile in which the active agent release characteristics of time course and/or location are chosen to accomplish therapeutic or convenience objectives not offered by conventional dosage forms such as solutions, suspensions, or promptly dissolving dosage forms. Delayed release, extended release, and pulsatile release and their combinations are examples of modified release.

The term "bioactive agent" or "active agent" refers to therapeutic, prophylactic, and/or diagnostic agents. It includes without limitation physiologically or pharmacologically active substances that act locally or systemically in the body. A biologically active agent is a substance used for, for example, the treatment, prevention, diagnosis, cure, or mitigation of disease or disorder, a substance which affects the structure or function of the body, or pro-drugs, which become biologically active or more active after they have been placed in a predetermined physiological environment. Bioactive agents include biologically, physiologically, or pharmacologically active substances that act locally or systemically in the human or animal body. Examples can include, but are not limited to, small-molecule drugs, peptides, proteins, antibodies, sugars, polysaccharides, nucleotides, oligonucleotides, aptamers, siRNA, nucleic acids, and combinations thereof. "Bioactive agent" includes a single agent or a plurality of bioactive agents including, for example, combinations of two or more bioactive agents.

II. Compositions

A. TGFβ and SMAD2 Inhibitors

As discussed above endothelial-to-mesenchymal transition (Endo-MT) is initiated in blood vessels after angioplasty, vascular graft, or other injury, by TGFβ signaling. In some embodiments, this TGFβ signaling is TGFβRI- and SMAD2-dependent. Therefore, TGFβ inhibitors and SMAD2 inhibitors are disclosed for inhibiting, preventing, and/or reversing Endo-MT in blood vessels.

1. SB431542

In some embodiments, the TFGβ or SMAD2 inhibitor is 4-[4-(1,3-Benzodioxol-5-yl)-5-(2-pyridinyl)-1H-imidazol-2-yl]-benzamide (SB431542).

SB431542 inhibits the activity of transforming growth factor β1 (TGF-β1) activin receptor-like kinases (ALKs). It is a selective and potent inhibitor of the phylogenetically related subset of ALK-4 (activin type I receptor), ALK-5 (TGFβRI), and ALK-7 (nodal type I receptor). SB431542 inhibits endogenous activin and TGF-β signaling but is without effect on the more divergent ALK-1, -2, -3, and -6 and hence BMP signaling. Phosphorylation of Smad2 by ectopically expressed constitutively active ALK-4, ALK-5, and ALK-7 in transfected NIH 3T3 cells is completely abolished by SB431542 at 10 mM (Watabe, T., et al., *J. Cell Biol.*, 163, 1303 (2003)). In addition, the compound inhibits ligand dependent activation of wild type ALK-4 and endogenous ALK-5 with an $IC_{50}$ of approximately 0.25 mM (Watabe, T., et al., *J. Cell Biol.*, 163, 1303 (2003)).

2. SB208

In some embodiments, the TFGβ or SMAD2 inhibitor is 2-(5-Chloro-2-fluorophenyl)-4-[(4-pyridyl)amino]pteridine (SB208). SB208 is a potent, orally active, ATP-competitive TGF-βRI inhibitor ($IC_{50}$=49 nM).

3. SB525334

In some embodiments, the TFGβ or SMAD2 inhibitor is 6-[2-(1,1-Dimethylethyl)-5-(6-methyl-2-pyridinyl)-1H-imidazol-4-yl]quinoxaline (SB525334). SB525334 is a selective inhibitor of TGF-βRI ($IC_{50}$=14.3 nM). It inhibits TGF-β1-induced smad2/3 nuclear localization and TGF-β1-induced mRNA expression.

4. LY2157299

In some embodiments, the TFGβ or SMAD2 inhibitor is 4-(2-(6-methylpyridin-2-yl)-5,6-dihydro-4H-pyrrolo[1,2-b]pyrazol-3-yl)quinoline-6-carboxamide (LY2157299). LY2157299 is a selective kinase inhibitor for TGF-βR1 with $IC_{50}$ of 86 nM. LY2157299 is well tolerated at doses of 40 mg and 80 mg.

5. EW-7203

In some embodiments, the TFGβ or SMAD2 inhibitor is 3-((5-([1,2,4]triazolo[1,5-a]pyridin-6-yl)-4-(6-methylpyridin-2-yl)thiazol-2-ylamino)methyl)benzonitrile (EW-7203). EW-7203 inhibits TGF-β1-induced Smad signaling and Endo-MT in mammary epithelial cells (Park C Y, et al. *Cancer Sci.* 102(10):1889-96 (2011)).

6. SM16

In some embodiments, the TFGβ or SMAD2 inhibitor is 4-(5-(benzo[d][1,3]dioxol-5-yl)-4-(6-methylpyridin-2-yl)-1H-imidazol-2-yl)bicyclo[2.2.2]octane-1-carboxamide (SM16). SM16 is a 430.5 MW ALK5/ALK4 kinase inhibitor that blocks TGF-β and activin-induced Smad2/3 phosphorylation.

7. Losartan

In some embodiments, the TFGβ inhibitor is (2-butyl-4-chloro-1-{[2'-(1H-tetrazol-5-yl)biphenyl-4-yl]methyl}-1H-imidazol-5-yl)methanol (Losartan). Losartan (rINN) is an angiotensin II receptor antagonist drug used mainly to treat high blood pressure that has also been shown to downregulate the expression of TGF-β types I and II receptors.

8. Competitive Binding Molecules

The SMAD pathway is the canonical signaling pathway that TGF-β family members signal through. In this pathway, TGF-β dimers bind to a type II receptor which recruits and phosphorylates a type I receptor. The type I receptor then recruits and phosphorylates a receptor regulated SMAD (R-SMAD).

Therefore, TGFβ signaling can also be inhibited with molecules that competitively bind TGFβ or TGFβRII and inhibit TGFβ signaling. SMAD2 activity can also be inhibited with molecules that competitively bind TGFβRI or SMAD2 and inhibit SMAD2 phosphorylation, translocation, or binding to DNA substrates. Examples of such competitive binding molecules as antibodies, soluble receptors (ligand trap), and mutant ligands.

Antibodies that can be used in the disclosed compositions and methods include whole immunoglobulin (i.e., an intact antibody) of any class, fragments thereof, and proteins containing at least the antigen binding variable domain of an antibody. The variable domains differ in sequence among antibodies and are used in the binding and specificity of each particular antibody for its particular antigen. The variability is not usually evenly distributed through the variable domains of antibodies. It is typically concentrated in three segments called complementarity determining regions (CDRs) or hypervariable regions both in the light chain and the heavy chain variable domains. The more highly conserved portions of the variable domains are called the framework (FR). The variable domains of native heavy and light chains each comprise four FR regions, largely adopting a beta-sheet configuration, connected by three CDRs, which form loops connecting, and in some cases forming part of the beta-sheet structure. The CDRs in each chain are held together in close proximity by the FR regions and, with the CDRs from the other chain, contribute to the formation of the antigen binding site of antibodies. Therefore, the disclosed antibodies contain at least the CDRs necessary to bind TGFβ, TGFβRI, TGFβRII, or SMAD2 and inhibit TGFβ signaling.

Techniques can also be adapted for the production of single-chain antibodies that bind TGFβ, TGFβRI, TGFβRII, or SMAD2 and inhibit TGFβ signaling. Methods for the production of single-chain antibodies are well known to those of skill in the art. A single chain antibody can be created by fusing together the variable domains of the heavy and light chains using a short peptide linker, thereby reconstituting an antigen binding site on a single molecule. Single-chain antibody variable fragments (scFvs) in which the C-terminus of one variable domain is tethered to the N-terminus of the other variable domain via a 15 to 25 amino acid peptide or linker have been developed without significantly disrupting antigen binding or specificity of the binding. The linker is chosen to permit the heavy chain and light chain to bind together in their proper conformational orientation. Divalent single-chain variable fragments (di-scFvs) can be engineered by linking two scFvs. This can be done by producing a single peptide chain with two VH and two VL regions, yielding tandem scFvs. ScFvs can also be designed with linker peptides that are too short for the two variable regions to fold together (about five amino acids), forcing scFvs to dimerize. This type is known as diabodies. Diabodies have been shown to have dissociation constants up to 40-fold lower than corresponding scFvs, meaning that they have a much higher affinity to their target. Still shorter linkers (one or two amino acids) lead to the formation of trimers (triabodies or tribodies). Tetrabodies have also been produced. They exhibit an even higher affinity to their targets than diabodies.

Soluble TGFβ receptors, such as a soluble TGFβRII receptor, may also be used to bind free TGFβ and prevent activation of TGFβ signaling. Soluble TGFβRI receptor may also be used to bind free SMAD2 and prevent phosphorylation of SMAD2. Soluble receptors are generally chimeric fusion proteins containing the extracellular domain of the receptor fused to the Fc portion of an immunoglobulin.

A mutant TGFβ ligands that bind TGFβRII without activating receptor signaling may be used to compete with endogenous TGFβ and inhibit TGFβRI signaling. A mutant SMAD2 that binds TGFβRI without being phosphorylated and activating downstream targets may be used to compete with endogenous TGFβRI for binding to endogenous SMAD2.

B. FGF Receptor Agonists

FGF signaling suppresses Endo-MT. Therefore, FGF agonists are disclosed for use in the disclosed compositions and methods. Therefore, FGF Receptor agonists are disclosed for use in the disclosed compositions and methods. Any FGF receptor agonists, i.e., agents composition that directly promotes FGF signaling through an FGF receptor (FGFR) can be used in the disclosed compositions and methods.

In some embodiments, the FGF Receptor agonist is natural, synthetic, or recombinant FGF peptide or protein that can bind and activate FGF Receptor signaling in an endothelial cell, such as a human endothelial cell. The FGF protein is preferably human. Recombinant human FGF-2 proteins are commercially available from, for example, INVITROGEN (Grand Island, N.Y.) and R&D SYSTEMS (Minneapolis, Minn.). Other examples of FGF proteins which are FGF agonists include FGF1, FGF4 and FGF-5, however, over 20 FGF family proteins (FGF 1-14 and FGF 1-23) have been identified, most of which bind to one or more of the 4 FOP receptors. Reviewed in Itoh, et al., *Trends in Genetics*, 20(11):563-9 (2004).

Expression vectors encoding an FGF protein, or fragment thereof, that binds and activates FGF Receptor may also be used. The expression vector may contain a nucleic acid encoding an FGF agonist operably linked to an expression control sequence.

Small molecule FGF Receptor agonist that may be used in the disclosed compositions and methods are described in U.S. Patent Publication No. 2009/0069368 by Bono, et al. Other FGF Receptor agonists include agonistic antibodies specific for FGF receptors, described for example in Malavaud, et al., *Oncogene*, 23:6769-6778 (2004).

C. Let-7 microRNA Agonists

FGF signaling suppresses Endo-MT by maintaining Let-7 microRNA expression, which prevents the activation of TGFβ, TGFβR1 and SMAD2. Therefore, Let-7 agonists are disclosed for use in the disclosed compositions and methods.

In preferred embodiments, the Let-7 agonist is a Let-7 miRNA or a polynucleotide encoding a Let-7 miRNA. In some embodiments, the Let-7 agonist is a pri-miRNA, pre-miRNA, mature miRNA, or a fragment or variant thereof effective in gene silencing, e.g., silencing TGFBRI gene expression. In other embodiments, the let-7 miRNA is an RNA interference-inducing (RNAi) molecule including, but not limited to, a siRNA, dsRNA, stRNA, shRNA, or gene silencing variants thereof. In alternative embodiments the let-7 miRNA is an agent which binds and inhibits an RNA transcript comprising a let-7 target sequence. Examples of such agents include, but are not limited to a small molecule, protein, antibody, aptamer, ribozyme, nucleic acid or nucleic acid analogue.

In some embodiments, the Let-7 miRNA is human let-7a1, let-7a2, let-7a4, let-7b, let-7e, let-7d, let-7d, let-7f1, let-7f2, let-7g, let-7i, or mir-98. Of these let-7 family members, Let-7b and Let-7c have the best sequence match with TGFβR1. The following are sequences for the human let-7 family members. Also disclosed are conservative variants of these sequences having 1, 2, 3, 4, 5, or 6 substitutions, deletions, or insertions

```
let-7a1
                                    SEQ ID NO: 102
UGGGAUGAGG UAGUAGGUUG UAUAGUUUUA

GGGUCACACC CACCACUGGG AGAUAACUAU

ACAAUCUACU GUCUUUCCUA let-7a2
                                    SEQ ID NO: 103
AGGUUGAGGU AGUAGGUUGU AUAGUUUAGA

AUUACAUCAA GGGAGAUAAC UGUACAGCCU

CCUAGCUUUC CU let-7a3
                                    SEQ ID NO: 104
GGGUGAGGUA GUAGGUUGUA UAGUUUGGGG

CUCUGCCCUG CUAUGGGAUA ACUAUACAAU

CUACUGUCUU UCCU let-7b
                                    SEQ ID NO: 105
CGGGGUGAGG UAGUAGGUUG UGUGGUUUCA

GGGCAGUGAU GUUGCCCCUC GGAAGAUAAC

UAUACAACCU ACUGCCUUCC CUG let-7c
                                    SEQ ID NO: 106
GCAUCCGGGU UGAGGUAGUA GGUUGUAUGG

UUUAGAGUUA CACCCUGGGA GUUAACUGUA

CAACCUUCUA GCUUUCCUUG GAGC let-7d
                                    SEQ ID NO: 107
CCUAGGAAGA GGUAGUAGGU UGCAUAGUUU

UAGGGCAGGG AUUUUGCCCA CAAGGAGGUA

ACUAUACGAC CUGCUGCCUU UCUUAGG let-7e
                                    SEQ ID NO: 108
CCCGGGCUGA GGUAGGAGGU UGUAUAGUUG

AGGAGGACAC CCAAGGAGAU CACUAUACGG

CCUCCUAGCU UUCCCCAGG
```

```
let-7f1
                                       SEQ ID NO: 109
UCAGAGUGAG GUAGUAGAUU GUAUAGUUGU

GGGGUAGUGA UUUUACCCUG UUCAGGAGAU

AACUAUACAA UCUAUUGCCU UCCCUGA let-7f2
                                       SEQ ID NO: 110
UGUGGGAUGA GGUAGUAGAU UGUAUAGUUU

UAGGGUCAUA CCCCAUCUUG GAGAUAACUA

UACAGUCUAC UGUCUUUCCC ACG let-7g
                                       SEQ ID NO: 111
AGGCUGAGGU AGUAGUUUGU ACAGUUUGAG

GGUCUAUGAU ACCACCCGGU ACAGGAGAUA

ACUGUACAGG CCACUGCCUU GCCA let-7i
                                       SEQ ID NO: 112
CUGGCUGAGG UAGUAGUUUG UGCUGUUGGU

CGGGUUGUGA CAUUGCCCGC UGUGGAGAUA

ACUGCGCAAG CUACUGCCUU GCUA mir-98
                                       SEQ ID NO: 113
AGGAUUCUGC UCAUGCCAGG GUGAGGUAGU

AAGUUGUAUU GUUGUGGGGU AGGGAUAUUA

GGCCCCAAUU AGAAGAUAAC UAUACAACUU

ACUACUUUCC CUGGUGUGUG GCAUAUUCA
```

In some embodiments, the Let-7 agonist is a vector encoding one or more let-7 miRNA operably linked to a transcription control element. For example, genes inserted in viral and retroviral systems usually contain promoters and/or enhancers to help control the expression of the desired gene product. A promoter is generally a sequence or sequences of DNA that function when in a relatively fixed location in regard to the transcription start site. A promoter contains core elements required for basic interaction of RNA polymerase and transcription factors, and may contain upstream elements and response elements. Enhancer generally refers to a sequence of DNA that function at no fixed distance from the transcription start site and can be either 5' or to the transcription unit. Furthermore, enhancers can be within an intron as well as within the coding sequence itself. They are usually between 10 and 300 bp in length, and they function in cis. Enhancers function to increase transcription from nearby promoters.

In some embodiments, the promoter is inducible. In other embodiments, the promoter is a constitutive to maximize expression of the region of the transcription unit to be transcribed. In some embodiments, the promoter is tissue-specific, e.g., expressed only in vascular endothelial cells.

D. Pharmaceutical Compositions

Pharmaceutical compositions containing therapeutically effective amounts of a TGFβ inhibitor, a SMAD2 inhibitor, an FGF Receptor agonist, a Let-7 agonist, or a combination thereof optionally in a pharmaceutically acceptable carrier/excipient are disclosed.

1. Formulations for Parenteral Administration

In one embodiment, the pharmaceutical composition is administered in an aqueous solution by parenteral injection. The formulation may also be in the form of a suspension or emulsion. In general, pharmaceutical compositions are provided including effective amounts of a TGFβ inhibitor, a SMAD2 inhibitor, an FGF Receptor agonist, a Let-7 agonist, or a combination thereof, and optionally include pharmaceutically acceptable diluents, preservatives, solubilizers, emulsifiers, adjuvants and/or carriers. Such compositions include diluents sterile water, buffered saline of various buffer content (e.g., Tris-HCl, acetate, phosphate), pH and ionic strength; and optionally, additives such as detergents and solubilizing agents (e.g., TWEEN® 20, TWEEN® 80, Polysorbate 80), anti-oxidants (e.g., ascorbic acid, sodium metabisulfite), and preservatives (e.g., Thimersol, benzyl alcohol) and bulking substances (e.g., lactose, mannitol). Examples of non-aqueous solvents or vehicles are propylene glycol, polyethylene glycol, vegetable oils, such as olive oil and corn oil, gelatin, and injectable organic esters such as ethyl oleate. The formulations may be lyophilized and redissolved/resuspended immediately before use. The formulation may be sterilized by, for example, filtration through a bacteria retaining filter, by incorporating sterilizing agents into the compositions, by irradiating the compositions, or by heating the compositions.

2. Controlled Delivery Polymeric Matrices

In one embodiment, the pharmaceutical composition containing a TGFTGFβ inhibitor, a SMAD2 inhibitor, an FGF Receptor agonist, a Let-7 agonist, or a combination thereof is administered systemically or locally using controlled release formulations. In a preferred embodiment, the pharmaceutical composition is administered locally at the site of a vascular device using a controlled release formulation.

In one embodiment, the pharmaceutical composition is coated on or incorporated into a polymeric vascular graft which functions as a controlled release formulation. The pharmaceutical composition may be dispersed throughout the polymeric vascular graft using any known suitable method. For example, the pharmaceutical composition is may be added to the polymeric scaffold during fabrication by adding it to the polymer solution or emulsion or during the fabrication of a polymeric textile, such as by an electro spinning process. Additionally, or alternatively, the pharmaceutical composition may be added to the polymeric graft following fabrication. In some embodiments, the pharmaceutical composition is localized to either the exterior or the lumen of the tubular polymeric vascular graft.

In another embodiment, the pharmaceutical composition may be encapsulated in a polymeric matrix that is either administered to the site of actual or potential neointimal stenosis or incorporated into the polymeric vascular graft. In some embodiments, the pharmaceutical composition is encapsulated into microspheres, nanospheres, microparticles and/or microcapsules. The matrix can be in the form of microparticles such as microspheres, where the active agent is dispersed within a solid polymeric matrix or microcapsules, where the core is of a different material than the polymeric shell, and the active agent is dispersed or suspended in the core, which may be liquid or solid in nature. Unless specifically defined herein, microparticles, microspheres, and microcapsules are used interchangeably. Alternatively, the polymer may be cast as a thin slab or film, ranging from nanometers to four centimeters, a powder produced by grinding or other standard techniques, or even a gel such as a hydrogel, and used as a coating for the vascular graft.

Either non-biodegradable or biodegradable matrices can be used for delivery of the pharmaceutical composition, although biodegradable matrices are preferred. These may be natural or synthetic polymers, although synthetic polymers are preferred due to the better characterization of degradation and release profiles. The polymer is selected based on the period over which release is desired. In some cases linear release may be most useful, although in others a pulse release or "bulk release" may provide more effective results. The polymer may be in the form of a hydrogel (typically in absorbing up to about 90% by weight of water), and can optionally be crosslinked with multivalent ions or polymers.

The matrices can be formed by solvent evaporation, spray drying, solvent extraction and other methods known to those skilled in the art. Bioerodible microspheres can be prepared using any of the methods developed for making microspheres for drug delivery.

3. Formulations for Enteral Administration

Bioactive agents that are not peptides or polypeptides can also be formulated for oral delivery. Oral solid dosage forms are known to those skilled in the art. Solid dosage forms include tablets, capsules, pills, troches or lozenges, cachets, pellets, powders, or granules or incorporation of the material into particulate preparations of polymeric compounds such as polylactic acid, polyglycolic acid, etc. or into liposomes. Such compositions may influence the physical state, stability, rate of in vivo release, and rate of in vivo clearance of the present proteins and derivatives. =Liposomal or polymeric encapsulation may be used to formulate the compositions. In general, the formulation will include the active agent and inert ingredients which protect peptide in the stomach environment, and release of the biologically active material in the intestine.

Another embodiment provides liquid dosage forms for oral administration, including pharmaceutically acceptable emulsions, solutions, suspensions, and syrups, which may contain other components including inert diluents; adjuvants such as wetting agents, emulsifying and suspending agents; and sweetening, flavoring, and perfuming agents.

Controlled release oral formulations may be desirable. Non-polypeptide bioactive agents can be incorporated into an inert matrix which permits release by either diffusion or leaching mechanisms, e.g., films or gums. Slowly disintegrating matrices may also be incorporated into the formulation. Another form of a controlled release is one in which the drug is enclosed in a semipermeable membrane which allows water to enter and push drug out through a single small opening due to osmotic effects. For oral formulations, the location of release may be the stomach, the small intestine (the duodenum, the jejunem, or the ileum), or the large intestine. Preferably, the release will avoid the deleterious effects of the stomach environment, either by protection of the active agent (or derivative) or by release of the active agent beyond the stomach environment, such as in the intestine. To ensure full gastric resistance an enteric coating (i.e, impermeable to at least pH 5.0) is preferred. Examples of the more common inert ingredients that are used as enteric coatings are cellulose acetate trimellitate (CAT), hydroxypropylmethylcellulose phthalate (HPMCP), HPMCP 50, HPMCP 55, polyvinyl acetate phthalate (PVAP), Eudragit L30D, Aquateric, cellulose acetate phthalate (CAP), Eudragit L, Eudragit S, and Shellac. These coatings may be used as mixed films or as capsules such as those available from Banner Pharmacaps.

4. Drug Eluting Steals

The pharmaceutical composition containing a TGFβ inhibitor, a SMAD2 inhibitor, an FGF Receptor agonist, a Let-7 agonist, or a combination thereof, may also be released from a drug-eluting stent. A typical drug-eluting stent is a peripheral or coronary stent (a scaffold) placed into narrowed, diseased peripheral or coronary arteries that slowly releases a drug to block cell proliferation. The disclosed stent can contain a TGFβ inhibitor, a SMAD2 inhibitor, an FGF Receptor agonist, a Let-7 agonist, or a combination thereof instead of, or in addition to, a drug that blocks cell proliferation.

Drug-eluting stents have three parts: a stent platform, a coating, and a drug. The stent itself is generally an expandable metal alloy framework. Many drug-eluting stents are based on a bare-metal stent (BMS). The stents have elaborate mesh-like designs to allow expansion, flexibility and in some cases the ability to make/enlarge side openings for side vessels. A coating, typically of a polymer, holds and elutes (releases) the drug into the arterial wall by contact transfer. Coatings are typically spray coated or dip coated. There can be one to three or more layers in the coating e.g. a base layer for adhesion, a main layer for holding the drug, and sometimes a top coat to slow down the release of the drug and extend its effect.

The main purpose of the drug is to inhibit neointimal growth which would cause restenosis. Existing drugs attempt to block proliferation of smooth muscle cells (SMC). The disclosed compositions containing a TGFβ inhibitor, a SMAD2 inhibitor, an FGF Receptor agonist, a Let-7 agonist, or a combination thereof, to inhibit Endo-MT of endothelial cells into SMC. Therefore, these compositions may also be used in combination with anti-proliferative drugs for a combinatorial effect. Immunosuppressive and antiproliferative drugs may also be included.

5. Dosage

In one embodiment, the TGFβ TGFβ inhibitor, a SMAD2 inhibitor, an FGF Receptor agonist, a Let-7 agonist, or a combination thereof is administered in a dose equivalent to parenteral administration of about 0.1 ng to about 100 g per kg of body weight, about 10 ng to about 50 g per kg of body weight, about 100 ng to about 1 g per kg of body weight, from about 1 µg to about 100 mg per kg of body weight, from about 1 µg to about 50 mg per kg of body weight, from about 1 mg to about 500 mg per kg of body weight; and from about 1 mg to about 50 mg per kg of body weight. Alternatively, the amount of pharmaceutical composition administered to achieve a therapeutic effective dose is about 0.1 ng, 1 ng, 10 ng, 100 ng, 1 µg, 10 µg, 100 µg, 1 mg, 2 mg, 3 mg, 4 mg, 5 mg, 6 mg, 7 mg, 8 mg, 9 mg, 10 mg, 11 mg, 12 mg, 13 mg, 14 mg, 15 mg, 16 mg, 17 mg, 18 mg, 19 mg, 20 mg, 30 mg, 40 mg, 50 mg, 60 mg, 70 mg, 80 mg, 90 mg, 100 mg, 500 mg per kg of body weight or greater.

Area under the curve (AUC) refers to the area under the curve that tracks the serum concentration (nmol/L) of the TGFTGFβ inhibitor, a SMAD2 inhibitor, an FGF Receptor agonist, a Let-7 agonist, or a combination thereof over a given time following the IV administration of the reference standard. By "reference standard" is intended the formulation that serves as the basis for determination of the total dose to be administered to a human subject to achieve the desired positive effect, i.e., a positive therapeutic response that is improved with respect to that observed without administration of the pharmaceutical composition. In a preferred embodiment, the dose of the TGFβ inhibitor, Let-7 agonist, or combination thereof provides a final serum level of TTGFβ inhibitor, a SMAD2 inhibitor, an FGF Receptor agonist, a Let-7 agonist, or a combination thereof of about 100 ng/ml to about 1000 ng/ml, about 1100 ng/ml to about 1450 ng/ml, 100 ng/ml to about 250 ng/ml, about 200 ng/ml to about 350 ng/ml, about 300 ng/ml to about 450 ng/ml, about 350 ng/ml to about 450 ng/ml, about 400 ng/ml to about 550 ng/ml, about 500 ng/ml to about 650 ng/ml, about 600 ng/ml to about 750 ng/ml, about 700 ng/ml to about 850 ng/ml, about 800 ng/ml to about 950 ng/ml, about 900 ng/ml to about 1050 ng/ml, about 1000 ng/ml to about 1150 ng/ml, about 100 ng/ml to about 1250 ng/ml, about 1200 ng/ml to about 1350 ng/ml, about 1300 ng/ml to about 1500 ng/m. In specific embodiments, the serum level of the TGFβ inhibitor, a SMAD2 inhibitor, an FGF Receptor agonist, a Let-7 agonist, or a combination thereof is about 100 ng/ml, 250 ng/ml, 300 ng/ml, 350 ng/ml, 360 ng/ml, 370 ng/ml, 380 ng/ml, 390 ng/ml, 400 ng/ml, 410 ng/ml, 420 ng/ml, 430 ng/ml, 440 ng/ml, 450 ng/ml, 500 ng/ml, 750 ng/ml, 900 ng/ml, 1200 ng/ml, 1400 ng/ml, or 1600 ng/ml.

Pharmaceutical formulations can be designed for immediate release, sustained release, delayed release and/or burst release of one or more active agents in a therapeutically effective amount. In a preferred embodiment, the formulation provides an initial burst release of a "loading dosage", followed by a sustained release to maintain the therapeutically effective dosage. This can be accomplished using a delayed and/or extended release formulation.

III. Methods for Inhibiting Neointima Stenosis

Methods are disclosed for inhibiting neointima stenosis. In some embodiments, the neointima stenosis results from injury to the vascular wall (endothelium) after a medical procedure, such as angioplasty, vascular graft implantation, or stent placement. The method involves inhibiting the endothelial to mesenchymal transition (Endo-MT) of vascular endothelial cells into smooth muscle cells (SMC). FGF signaling suppresses Endo-MT by maintaining Let-7 microRNA expression, which prevents the activation of TGFβ, TGFβR1 and SMAD2 expression. Therefore, the disclosed method involves the use of a composition containing a TGFβ inhibitor, a SMAD2 inhibitor, an FGF Receptor agonist, a Let-7 agonist, or a combination thereof to inhibit Endo-MT at the site of actual or potential neointima formation.

In some embodiments, the composition is coated on or incorporated into a vascular device, such as a vascular graft, angioplasty balloon, or vascular stent prior to its use. The composition may coated on or incorporated into the vascular device using any known suitable method. The composition may be encapsulated in the form of microspheres, nanospheres, microparticles and/or microcapsules, and seeded on or into the vascular device.

In other embodiments, the composition is administered directly to the subject before, during, or after a medical procedure that may damage a vascular wall. In these embodiments, the composition is preferably administered locally to the site of actual or potential neointima formation.

A. Administration

In some embodiments, a pharmaceutical composition containing a TGFβ inhibitor, a SMAD2 inhibitor, an FGF Receptor agonist, a Let-7 agonist, or a combination thereof is administered to a subject receiving a vascular device in an effective amount to prevent, inhibit or reduce neointimal stenosis. The precise dosage will vary according to a variety of factors such as the nature of the compound being administered, the route of administration, and subject-dependent variables (e.g., age, etc.).

The pharmaceutical composition may be administered systemically or locally at the site of vascular graft implantation. The compositions may be administered prior to vascular device implantation, at the same time as vascular device implantation, following vascular device implantation, or any combination thereof. In one embodiment, the composition is administered either locally or systemically from a controlled release formulation. The composition may be administered separately from additional bioactive agents or may be co-administered.

Pharmaceutical compositions containing a TGFβ inhibitor, a SMAD2 inhibitor, an FGF Receptor agonist, a Let-7 agonist, or a combination thereof may be administered by parenteral (intramuscular, intraperitoneal, intravenous (IV) or subcutaneous injection), transdermal (either passively or using iontophoresis or electroporation), or transmucosal (nasal, vaginal, rectal, or sublingual) routes of administration. The compositions can be formulated in dosage forms appropriate for each route of administration. Compositions containing bioactive agents that are not peptides or polypeptides can additionally be formulated for enteral administration.

IV. Methods for Promoting Patency of Biodegradable, Synthetic Vascular Grafts The patency of biodegradable, synthetic vascular grafts may be increased using a composition that inhibits Endo-MT. Therefore, a method for promoting patency of a biodegradable, synthetic vascular graft is disclosed that involves administering a composition that inhibits Endo-MT to the graft or to the subject prior to or after implantation. Also disclosed is a cell-free tissue engineered vascular graft (TEVG) produced by this method.

Suitable Endo-MT inhibitors include TGFTGFβ inhibitor, a SMAD2 inhibitor, an FGF Receptor agonist, a Let-7 agonist, or a combination thereof. The administration of Endo-MT inhibitors increases the patency of the biodegradable, synthetic vascular grafts.

The disclosed biodegradable, synthetic vascular grafts do not require cell seeding to maintain patency of the grafts. This is advantageous, because it avoids problems associated with cell seeding, including the need for an invasive procedure to obtain autologous cells, the need for a substantial period of time in order to expand the cells in culture, the inherent difficulty in obtaining healthy autologous cells from diseased donors, and an increased risk of contamination and the potential for dedifferentiation of the cells. The disclosed biodegradable, synthetic vascular grafts therefore have a greater the off-the-shelf availability and increased overall clinical utility.

A. Polymeric Vascular Grafts

The disclosed polymeric vascular grafts are typically tubular porous conduits fabricated using biodegradable polymers. The pores in the polymeric vascular grafts allow for recruitment and integration of host cells into the graft. It is believed that recruited host cells mediate outward vascular tissue remodeling and vascular neotissue formation. Unlike synthetic vascular grafts that are currently in clinical use, the disclosed polymeric vascular grafts are biodegradable, which allows for the grafts to become replaced by forming neotissue as they degrade. Thus, the disclosed polymeric vascular grafts offer growth potential that is not possible with currently used synthetic vascular grafts.

The disclosed grafts are preferably substantially tubular in shape with a round or substantially round cross section. The tubular grafts have a lumen extending throughout the length of the graft. The grafts may be of any appropriate length and diameter that is suitable for the intended surgical use of the graft. Typically, the graft should be slightly longer than the length of artery or vein that is to be replaced.

The porous polymeric vascular grafts may be fabricated using any appropriate method, such as melt processing, solvent processing, leaching, foaming, extrusion, injection molding, compression molding, blow molding, spray drying, extrusion coating, and spinning of fibers with subsequent processing into woven or non-woven constructs. Pores in the graft may be derived by any suitable method, including salt leaching, sublimation, solvent evaporation, spray drying, foaming, processing of the materials into fibers and subsequent processing into woven or non-woven devices. Preferably, the pores of the device are between 5 μm and 500 μm, more preferably between 5 μm and 250 μm, more preferably between 5 μm and 100 μm, in diameter.

In some embodiments, the grafts are formed from a felt or sheet like material of the polymer that can be formed into a tubular conduit. For example the device could be fabricated as a nonwoven, woven or knitted structure from extruded polymeric fibers. The polymeric sheet may be formed using any textile construction, including, but not limited to, weaves, knits, braids or filament windings. Any suitable method, such as electrospinning, may be used to fabricate the nonwoven or woven polymeric textile.

The polymers and fabrication methods selected to fabricate the polymeric vascular grafts are suitable to produce grafts with biomechanical properties suitable for use as vascular conduits. Biomechanical properties that are important for vascular graft function include initial burst pressure, suture retention strength and elasticity. In some embodiments, the initial burst pressure of the polymeric vascular graft is between about 1,500 mmHg and about 4,500 mmHg, preferably between about 2,000 mmHg and about 4,500 mmHg. In another embodiment, the polymeric vascular grafts possess suture retention strengths between about 1 N and about 5 N, preferably between about 2 N and about 4 N. In another embodiment, the intrinsic elasticity of the vascular grafts is between about 10 MPa and about 50 MPa, preferably between about 15 MPa and about 40 MPa. In another embodiment, the initial tensile strength of the vascular grafts is between about 1 MPa and about 10 MPa, preferably between about 3 MPa and about 6 MPa.

1. Biodegradable Polymers

The biodegradable, synthetic vascular grafts may be fabricated using any known biodegradable polymer, co-polymer, or mixture thereof. Many suitable biodegradable polymers are known in art.

Examples of preferred biodegradable polymers include synthetic polymers that degrade by hydrolysis such as poly(hydroxy acids), such as polymers and copolymers of lactic acid and glycolic acid, polyanhydrides, poly(ortho) esters, polyesters, polyurethanes, poly(butic acid), poly(valeric acid), poly(caprolactone), poly(hydroxyalkanoates), and poly(lactide-co-caprolactone). The foregoing materials may be used alone, as physical mixtures (blends), or as co-polymers. In a preferred embodiment, the biodegradable, synthetic vascular grafts are fabricated from polyglycolic acid or poly-L-lactic acid.

2. Sealants

Synthetic vascular grafts fabricated from nonwoven, woven or knitted sheets or felts of biodegradable polymers may be further treated with polymeric sealants. The polymeric sealants function to modify the biomechanical properties of the vascular grafts, such as tensile strength and elasticity. Polymeric sealants may also be used to control the total porosity and pore size distribution range of the vascular graft.

Polymeric sealants for the disclosed biodegradable synthetic vascular grafts may be any biodegradable polymer, including, but not limited to, the list of biodegradable polymers listed above. In one embodiment, the polymeric sealant is a copolymer of poly(ε-caprolactone) and poly(L-lactide). The copolymer can be at a ratio from 5:95 to 95:5, preferably from 30:70 to 70:30, more preferably from 40:60 to 60:40, most preferably about 50:50.

Polymeric sealants may be added to tubular synthetic grafts dissolved in an appropriate solvent to allow for the sealant to penetrate the nonwoven, woven or knitted sheet or felt of biodegradable polymers forming the graft. The polymeric sealant may then be quickly transformed from liquid to solid phase by lowering the temperature of the graft. Solvents may then be removed by an appropriate technique, such as lyophilization.

C. Additional Bioactive Agents

Additional bioactive agents that promote vascular graft adaptation may also be administered. Suitable bioactive agents or drugs include, but are not limited to: anti-thrombogenic agents, such as heparin, heparin derivatives, urokinase, and PPack (dextrophenylalanine praline arginine chloromethylketone; anti-proliferative agents, such as enoxaprin, angiopeptin, hirudin, acetylsalicylic acid, paclitaxel, 5-fluorouracil, cisplatin, vinblastine, vincristine, epothilones, endostatin, angiostatin and thymidine kinase inhibitors; anesthetic agents, such as lidocaine, bupivacaine, and ropivacaine; anti-coagulants, such as D-Phe-Pro-Arg chloromethyl keton, RGD peptide-containing compounds, heparin, antithrombin compounds, platelet receptor antagonists, anti-thrombin antibodies, anti-platelet receptor antibodies, aspirin, prostaglandin inhibitors, platelet inhibitors and tick antiplatelet peptides; cholesterol-lowering agents; vasodilating agents; and agents which interfere with endogenous vascoactive mechanisms.

D. Uses for Biodegradable, Synthetic Vascular Grafts

The disclosed biodegradable, synthetic vascular grafts may be used as venous, arterial or artero-venous conduits for any vascular or cardiovascular surgical application. Exemplary applications include, but are not limited to, congenital heart surgery, coronary artery bypass surgery, peripheral vascular surgery and angioaccess.

Vascular bypass grafting is most commonly performed for the treatment of vessel stenosis. However, vascular grafts are also used for the treatment of other conditions such as arterial aneurysm or chronic renal failure (as access for hemodialysis). Vascular grafting can be performed by conventional surgery or endovascular techniques.

Coronary artery bypass grafting (CABG) is one example of vascular bypass surgery. With this procedure, a bypass graft is used to bypass the coronary artery distal to the site of stenosis or occlusion. When a vein graft is used, one end is anastomosed to the aorta and the other end is anastomosed to the coronary artery beyond the stenosis or occlusion. When an arterial graft is used, the proximal end is left undisturbed (thus preserving the artery's normal blood inflow) and the distal end is anastomosed to the coronary artery beyond the stenosis or occlusion.

Typically, an anastomosis (i.e., the surgical union of tubular parts) between the in situ artery or vein and the synthetic graft is created by sewing the graft to the in situ vessel with suture. Commonly used suture materials include proline (extruded polypropyline) and ePTFE.

EXAMPLES

Example 1

Basal FGF Signaling Suppresses TGFβ-Mediated Endo-MT

Materials and Methods
Cell Culture and Reagents

Human 293T T17 cells (ATCC CRL-11268) were maintained in Dulbecco's modified Eagle's medium (Gibco) with 10% fetal bovine serum (Invitrogen) and penicillinstreptomycin (Gibco). Primary human mammary epithelial cells (HuMEC, Invitrogen), were maintained in HuMEC basal serum free medium with HuMEC supplement (Invitrogen 12754-016) and bovine pituitary extract (Invitrogen 13028-014). Human foreskin cells (ATCC CRL-1079Sk) were maintained in Minimum Essential Medium (ATCC) with 10% fetal bovine serum (Hyclone), β-mercaptoethanol (Sigma), and penicillin-streptomycin (Gibco). Primary human atrial cells (passage 3-5; gift from Y. Qyang, Yale University School of Medicine) were maintained in Dulbecco's modified Eagle's medium (Gibco) with 10% fetal bovine serum (Invitrogen), L-glutamine (Gibco), Sodium pyruvate (Gibco), Non-essential amino acid (Gibco), and penicillin-streptomycin (Gibco). HUAEC (human umbilical artery endothelial cells, passage 5-10, Lonza) were cultured in EBM-2 supplemented with EGM-2-MV bullet kit (Lonza). HUVEC (human umbilical vein endothelial cells, passage 3-7, Yale Vascular Biology and Therapeutics) were cultured in M199 with ECGS, supplemented with 20% FBS (Sigma), L-glutamine (Gibco), and penicillin-streptomycin (Gibco). Culture vessels were coated with 0.1% gelatin (Sigma) for 30 min at 37° C. immediately prior to cell seeding. Primary mouse endothelial cells were isolated from the heart using rat anti-mouse CD31 antibody and Dynabeads (Invitrogen) as previously described (Partovian C, et al. Mol. Cell. 32(1):140 (2008)).

Antibodies Used for Immunodetection of Proteins

The following antibodies were used for flow cytometry (F), immunoblotting (IB), immunofluorescence (IF), or immunohistochemistry (IHC): antibodies to 5G11 (IB; Mood K, et al. J Biol. Chem. 277(36):33196 (2002)), β-galactosidase (Ab9361, Abcam; IF), Calponin, clone hCP (C-2687, Sigma; IB), CD31 (sc-1506, Santa Cruz; IB), CD31 (Ab28364-100, Abcam; IF), CD31 (550274, BD Pharmingen; EC isolation), CD31-APC (FAB3567A, R&D; F), FLAG (F1804, Sigma; IB), FRS2 (H-91, Santa Cruz; IB), Lin28A (3695, Cell Signaling; IB), N-cadherin (610920, BD Transduction Laboratories; IB), Smad2 (3122, Cell Signaling; IB), p-Smad2 (Ser465/467) (3108, Cell Signaling; IB), SM22 alpha (ab14106, Abcam; IB), smooth muscle α-actin clone 1A4 (A2547, Sigma; IB), smooth muscle α-actin (M0851, Dako; IF), TGFβ (Ab53169, Abcam; IHC), TGFβR1 (sc-398, Santa Cruz; IB), β-tubulin (T7816, Sigma; IB), VE-cadherin (C-19, Santa Cruz; IB, IF), Vimentin clone V9 (V6630, Sigma; IB), VEGFR2 (2479, Cell Signaling; IB), ZEB1 (HPA027525, Sigma; IB).

Plasmid and Lentivirus Constructs

TGFβR1, TGFβR1 T202D, and TGFβR1 K230R were purchased from Addgene and subcloned into the lentivirus pLVX-IRES-Puro vector (Clontech). BamH1-cleaved cDNAs fragments encoding Xenopus dominant negative FGFR1, constitutively active FGFR1 K562E, and its derivative mutants were inserted into the lentivirus pLVX-IRESPuro vector. Plasmids containing multiple mutations were generated using the QuickChange site-directed mutagenesis kit (Stratagene) employing the mouse FRS2 construct as template according to the manufacturer's recommendation. The FRS2 mutants were introduced using the primers in Table 1.

TABLE 1

Primers for introducing FRS1 mutants

| Primer | Primer Sequence (5' → 3') | |
|---|---|---|
| FRS2 Y196F | GCTGAGGAAC AAGTACATAC TTTTGTTAAC ACTACAGGTG TGCAA | SEQ ID NO: 1 |
| | CTTGCACACC TGTAGTGTTA ACAAAAGTAT GTACTTGTTC CTCAGC | SEQ ID NO: 2 |
| FRS2 Y306F | GCCCCCTGTC AACAAACTGG TGTTTGAAAA TATAAACGGG CTATCTATTC | SEQ ID NO: 3 |
| | GAATAGATAG CCCGTTTATA TTTTCAAACA CCAGTTTGTT GACAGGGGGC | SEQ ID NO: 4 |
| FRS2 Y349F | GAGAAGACCT GCACTATTAA ACTTTGAAAA TTTACCATCT TTGCCTCC | SEQ ID NO: 5 |
| | GGAGGCAAAG ATGGTAAATT TTCAAAGTTT AATAGTGCAG GTCTTCTC | SEQ ID NO: 6 |
| FRS2 Y392F | GATCCAATGC ATAACTTTGT TAATACAGAG AATGTAACAG TGCCG | SEQ ID NO: 7 |
| | CGGCACTGTT ACATTCTCTG TATTAACAAA GTTATGCATT GGATC | SEQ ID NO: 8 |
| FRS2 Y436F | GTTTAGAACA TAGGCAACTC AATTTTATAC AGGTGGATTT GGAAGG | SEQ ID NO: 9 |
| | CCTTCCAAAT CCACCTGTAT AAAATTGAGT TGCCTATGTT CTAAAC | SEQ ID NO: 10 |
| FRS2 Y471F | CACGCGGCGC ACAGAGCTGT TCGCTGTGAT AGACATTGAG AGAA | SEQ ID NO: 11 |
| | TTCTCTCAAT GTCTATCACA GCGAACAGCT CTGTGCGCCG CGTG | SEQ ID NO: 12 |

The constructs were verified by sequence analysis (Yale Keck DNA sequencing core facility), and protein expression was confirmed by immunoblot analysis.

Generation of Lentiviruses

The production of FRS2 lentivirus was previously described (Murakami JCI in press). For the production of miRNA lentivirus, 10 µg of pMIRNA1 carrying the let-7 miRNA expression cassette (System Biosciences), 5 µg of pMDLg/PRRE, 2.5 µg of RSV-REV, and 3 µg of pMD.2G were co-transfected into 293T cells using Fugene 6. Forty eight hr later, the medium was harvested, cleared by 0.45 µm filter, mixed with polybrene (Sigma), and applied to the cells. After 6 hr incubation, the virus-containing medium was replaced by fresh medium.

Western Blot Analysis

Tissues and cells were lysed with T-PER (Thermo scientific) containing complete mini protease inhibitors (Roche) and phosphatase inhibitors (Roche). 20 µg of total protein from each sample was resolved on a 4%-12% Bis-Tris Gel (Bio-Rad) with MOPs Running Buffer (Bio-Rad) and transferred to nitrocellulose membranes (Bio-Rad). The blots were then probed with various antibodies. Chemiluminescence measurements were performed using SuperSignal West Femto Maximum Sensitivity Substrate (Thermo Fisher Scientific).

RNA Isolation, qRT-PCR, and Gene Expression Profiling

RNA was isolated using RNeasy® plus Mini Kit (Qiagen) and converted to cDNA using iScript™ cDNA synthesis kit (Bio-Rad). Quantitative real-time PCR (qRT-PCR) was performed using Bio-Rad CFX94 (Bio-Rad) by mixing equal amount of cDNAs, iQ™ SYBR® Green Supermix (Bio-Rad) and gene specific primers. All reactions were done in a 25 µl reaction volume in duplicate. Data were normalized to endogenous β-actin. Values are expressed as fold change in comparison to control. Primers are listed in Table 2. Mouse TGFβ gene expression was quantified via qRT-PCR with TaqMan® Gene Expression Assays (Mm00441726_m1; Applied Biosystems) and HPRT (Mm00441258_1; Applied Biosystems) as endogenous control followed the manufacturer's recommendation. Quantitative PCR analysis of 84 TGFβ and epithelial to mesenchymal transition (EMT) related genes were performed using Human TGFβ BMP signaling pathway (PAHS-035D, QIAGEN) and Human Epithelial to Mesenchymal Transition (PAHS-090D, QIAGEN) RT$^2$ Profiler™ PCR Arrays following the manufacturer's protocol. RT$^2$ Profiler™ PCR arrays were nm on a Bio-Rad CFX96 machine (Bio-Rad). Duplicate arrays were run per condition for control and FRS2 knockdown human umbilical arterial endothelial cells (HUAEC). Data analysis was performed using the manufacturer's integrated web-based software package for the PCR Array System using cycle threshold (Ct)-based fold-change calculations.

TABLE 2

Primers used for quantitative RT-PCR analysis of mouse and human genes

| Gene | Primer sequence 5' → 3' | |
|---|---|---|
| Mouse Lin28 | GGCATCTGTAAGTGGTTCAACG | SEQ ID NO: 13 |
| | CCCTCCTTGAGGCTTCGGA | SEQ ID NO: 14 |
| Mouse Myocardin | GATGGGCTCTCTCCAGATCAG | SEQ ID NO: 15 |
| | GGCTGCATCATTCTTGTCACTT | SEQ ID NO: 16 |
| Mouse NG2 | GGGCTGTGCTGTCTGTTGA | SEQ ID NO: 17 |
| | TGATTCCCTTCAGGTAAGGCA | SEQ ID NO: 18 |
| Mouse PDGFRα | TCCATGCTAGACTCAGAAGTCA | SEQ ID NO: 19 |
| | TCCCGGTGGACACAATTTTTC | SEQ ID NO: 20 |
| Mouse PDGFRβ | TTCCAGGAGTGATACCAGCTT | SEQ ID NO: 21 |
| | AGGGGGCGTGATGACTAGG | SEQ ID NO: 22 |
| Mouse Runx1 | GCAGGCAACGATGAAAACTACT | SEQ ID NO: 23 |
| | GCAACTTGTGGCGGATTTGTA | SEQ ID NO: 24 |
| Mouse SM α-actin | GTCCCAGACATCAGGGAGTAA | SEQ ID NO: 25 |
| | TCGGATACTTCAGCGTCAGGA | SEQ ID NO: 26 |
| Mouse SM22_ | CAACAAGGGTCCATCCTACGG | SEQ ID NO: 27 |
| | ATCTGGGCGGCCTACATCA | SEQ ID NO: 28 |
| Mouse SM-calponin | AAACAAGAGCGGAGATTTGAGC | SEQ ID NO: 29 |
| | TGTCGCAGTGTTCCATGCC | SEQ ID NO: 30 |
| Mouse SM-MHC | AAGCTGCGGCTAGAGGTCA | SEQ ID NO: 31 |
| | CCCTCCCTTTGATGGCTGAG | SEQ ID NO: 32 |
| Mouse TGFβRI | TCCCAACTACAGGACCTTTTTCA | SEQ ID NO: 33 |
| | GCAGTGGTAAACCTGATCCAGA | SEQ ID NO: 34 |
| Mouse Vimentin | CGGCTGCGAGAGAAATTGC | SEQ ID NO: 35 |
| | CCACTTTCCGTTCAAGGTCAAG | SEQ ID NO: 36 |
| Mouse β-actin | GTTGTCGACGACGAGCG | SEQ ID NO: 37 |
| | GCACAGAGCCTCGCCTT | SEQ ID NO: 38 |
| Human CD31 | AACAGTGTTGACATGAAGAGCC | SEQ ID NO: 39 |
| | TGTAAAACAGCACGTCATCCTT | SEQ ID NO: 40 |

TABLE 2-continued

Primers used for quantitative RT-PCR analysis of mouse and human genes

| Gene | Primer sequence 5' → 3' | |
|---|---|---|
| Human Collagen 1A1 | TTCTGTTCGCAGGTGATTGG | SEQ ID NO: 41 |
| | CATGTTCAGCTTTGTGGACC | SEQ ID NO: 42 |
| Human FSP1 | AACTTGTCACCCTCTTTGCC | SEQ ID NO: 43 |
| | TCCTCAGCGCTTCTTCTTTC | SEQ ID NO: 44 |
| Human Fibronectin | AAACCAATTCTTGGAGCAGG | SEQ ID NO: 45 |
| | CCATAAAGGGCAACCAAGAG | SEQ ID NO: 46 |
| Human HMGA2 | GATCCAACTGCTGCTGAGGT | SEQ ID NO: 47 |
| | AGGCAGACCTAGGAAATGGC | SEQ ID NO: 48 |
| Human Lin28 | CGGGCATCTGTAAGTGGTTC | SEQ ID NO: 49 |
| | CAGACCCTTGGCTGACTTCT | SEQ ID NO: 50 |
| Human N-cadherin | GAGGAGTCAGTGAAGGAGTCA | SEQ ID NO: 51 |
| | GGCAAGTTGATTGGAGGGATG | SEQ ID NO: 52 |
| Human Smad2 | GCCATCACCACTCAAAACTGT | SEQ ID NO: 53 |
| | GCCTGTTGTATCCCACTGATCTA | SEQ ID NO: 54 |
| Human SM α-actin | CAAAGCCGGCCTTACAGAG | SEQ ID NO: 55 |
| | AGCCCAGCCAAGCACTG | SEQ ID NO: 56 |
| Human SM22α | GATTTTGGACTGCACTTCGC | SEQ ID NO: 57 |
| | GTCCGAACCCAGACACAAGT | SEQ ID NO: 58 |
| Human SM-calponin | CTGGCTGCAGCTTATTGATG | SEQ ID NO: 59 |
| | CTGAGAGAGTGGATCGAGGG | SEQ ID NO: 60 |
| Human TGFβ1 | CAAGCAGAGTACACACAGCAT | SEQ ID NO: 61 |
| | TGCTCCACTTTTAACTTGAGCC | SEQ ID NO: 62 |
| Human TGFβRI | ACGGCGTTACAGTGTTTCTG | SEQ ID NO: 63 |
| | GCACATACAAACGGCCTATCT | SEQ ID NO: 64 |
| Human TGFβRII | TCTGGTTGTCACAGGTGGAA | SEQ ID NO: 65 |
| | GCACGTTCAGAAGTCGGTTA | SEQ ID NO: 66 |
| Human VE-cadherin | CATGAGCCTCTGCATCTTCC | SEQ ID NO: 67 |
| | ACAGAGCTCCACTCACGCTC | SEQ ID NO: 68 |
| Human VEGFR2 | CGGCTCTTTCGCTTACTGTT | SEQ ID NO: 69 |
| | TCTCTCTGCCTACCTCACCTG | SEQ ID NO: 70 |
| Human Vimentin | GCAAAGATTCCACTTTGCGT | SEQ ID NO: 71 |
| | GAAATTGCAGGAGGAGATGC | SEQ ID NO: 72 |
| Human ZEB1 | CAGTCAGCTGCATCTGTAACAC | SEQ ID NO: 73 |
| | CCAGGTGTAAGCGCAGAAAG | SEQ ID NO: 74 |
| Human ZEB2 | CAAGAGGCGCAAACAAGCC | SEQ ID NO: 75 |
| | GGTTGGCAATACCGTCATCC | SEQ ID NO: 76 |
| Human β-actin | ATCAAGATCATTGCTCCTCCTGAG | SEQ ID NO: 77 |
| | CTGCTTGCTGATCCACATCTG | SEQ ID NO: 78 |

MicroRNA Target Prediction

To identify potential miRNA binding sites within the 3'UTR of TGFβR1, the following bioinformatic databases were used: TargetScan, PitTar, and DIANA-microT v3.0.

microRNA Real-Time PCR Analysis

Quantitative PCR analysis of 88 miRNA was performed using Human Cell Differentiation & Development RT² Profiler™ PCR Arrays (MAH-103A, QIAGEN) following the manufacturer's protocol. Validation of microRNA array data was performed with the RT² miRNA qPCR Assays and RT-PCR Primer Sets according to the manufacturer's instructions (QIAGEN). Primers for human mature let-7a (MPH00001A), let-7b (MPH00002A), let-7c (MPH00003A), let-7d (MPH00004A), let-7e (MPH00005A), let-7f (MPH00006A), let-7g (MPH00007A), mir-98 (MPH00480A), SNORD47 (MPH01660A) were from QIAGEN. Primers for mouse mature let-7a (MPM00483A), let-7b (MPM00484A), let-7c (MPM485A), let-7d (MPM00486A), let-7e (MPM00487A), let-7f (MPM00488A), let-7g (MPM00489A), let-7i (MPM00490A), mir-98 (MPM00875A) were from QIAGEN. Individual miRNA expression was normalized in relation to expression of small nuclear U6B RNA, a commonly used internal control for miRNA quantification assay.

PCR amplification consisted of 10 min of an initial denaturation step at 95° C., followed by 45 cycles of PCR at 95° C. for 30 s, 60° C. for 30 s.

Flow Cytometry

Cells were incubated with 10 µg/ml Dil-Ac-LDL for 4 hr at 37° C. Cells were then trypsinized, stained with APC-conjugated anti-PECAM-1 antibody or isotype control (R&D) and analyzed by FACScan™ (Becton Dickinson) and Flow-Jo Software (TreeStar). Two independent experiments were performed by duplicate.

Transfection of miRNA Mimics and Luciferase Reporter Assays

For reporter assays, cells were plated in 6-well plates and co-transfected with 1 µg let-7 core 4 firefly luciferase reporter plasmid using Fugene® 6 (Roche). After 24 hr, cells were transfected with let-7 miRNA mimic (10 nM; QIAGEN) or control oligonucleotides (10 nM; QIAGEN) using HiPerFect® reagent (QIAGEN). After 24 hr of incubation, cells were lysed in passive lysis buffer (Promega) and luciferase activity was measured with the Dual-Luciferase Reporter Assay System (Promega) using TD-20/20 Luminometer (Turner Designs).

Growth Factors and Chemicals

Recombinant human FGF2 (R&D) and TGFβ1 (Peprotech) were reconstituted in 0.1% BSA/PBS. U0126 (Sigma), a MEK inhibitor, was reconstituted in DMSO and used at a final concentration of 10 µM. SB431542 (Sigma), a TGFBR1 kinase inhibitor, was reconstituted in DMSO and used at a final concentration of 10 µM in cell culture. Actinomycin D (Sigma), a DNA transcription suppressor, was reconstituted in acetone and used at a final concentration of 10 µg/ml in cell culture. Cycloheximide (Sigma), a protein synthesis inhibitor, was reconstituted in DMSO and used at a final concentration of 10 µM in cell culture.

Generation of Mice and Embryos

FRS2$^{flox/flox}$ (Lin Y, et al. *Genesis*. 45(9):554 (2007)) and FRS2α 2F (Gotoh N, et al. *Proc Natl Acad Sci USA*. 101(49):17144 (2004)) mice were previously described. Tie2-Cre transgenic mice or Cdh5-CreERT2 transgenic mice were crossed with R26R-lacZ [B6,129-Gt(ROSA) 26Sor$^{tm1Sho/J}$] (JAX SN:003309) or mT/Mg [B6,129(Cg)-Gt(ROSA)26Sor$^{tm4(ACTB-tdTomato,-EGFP)Luo}$/J] (JAX SN:007676) mice to generate endothelial cell-specific reporter mice. For embryo analysis, timed matings were set up and the morning of the vaginal plug was considered as embryonic day 0.5 (E0.5). Embryos were genotyped by PCR analysis of the yolk sacs. PCR genotyping was performed using the primers in Table 3.

TABLE 3

Primers for PCT genotyping FRS2$^{flox/flox}$ mice

| Primer | Primer Sequence (5' → 3') | | |
|---|---|---|---|
| FRS2 2F | AGAATGGTGGCACAAACCAATAATCC | SEQ ID NO: | 79 |
| | CAATTCTTAACACCCACAAGGCCG | SEQ ID NO: | 80 |
| FRS2$^{flox/flox}$ | GAGTGTGCTGTGATTGGAAGGCAG | SEQ ID NO: | 81 |
| | GCACGAGTGTCTGCAGACACATG | SEQ ID NO: | 82 |
| Rosa26 | GCGAAGAGTTTGTCCTCAACC | SEQ ID NO: | 83 |
| | AAAGTCGCTCTGAGTTGTTAT | SEQ ID NO: | 84 |
| | GGAGCGGGAGAAATGGATATG | SEQ ID NO: | 85 |
| Tie2-Cre | GCGGTCTGGCAGTAAAAACTATC | SEQ ID NO: | 86 |
| | GTGAAACAGCATTGCTGTCACTT | SEQ ID NO: | 87 |
| | CTAGGCCACAGAATTGAAAGATCT | SEQ ID NO: | 88 |
| | GTAGGTGGAAATTCTAGCATCATCC | SEQ ID NO: | 89 |

Statistical Analysis

Statistical comparisons between groups were performed by the one-way analysis of variance followed by the Student t-test. P values less than 0.05 were considered significant.

Results

To test the role of FGF signaling in EC, RNA interference was used to inhibit the expression of FRS2. Immunofluorescence staining showed that while control HUAEC display a typical rounded/cobblestone morphology, after FRS2 knockdown there was a distinct change in cell shape accompanied by expression of smooth muscle calponin (SM-calponin), a protein not normally expressed in the endothelium, while an endothelial marker VE-cadherin was still expressed. Western blotting confirmed the appearance of this and other smooth muscle cell markers in FRS2 knockdown cells. FACS analysis showed that both control and FRS2 knockdown EC expressed CD31 and were able to take up Dil-acLDL, ruling out smooth muscle cell contamination. Similar results were obtained in primary mouse FRS2$^{flox/flox}$ EC following Ad-Cre transduction (FIGS. 9A-9J).

These finding indicated that following FRS2 knockdown EC are undergoing Endo-MT. Since TGFβ signaling has been implicated in Endo-MT, the expression of genes involved in TGFβ signaling was examined. qPCR analysis demonstrated a marked increase in expression of TGFβ1 and TGFβ2, all three TGFβ receptors and several collagen isoforms that are stimulated by TGFβ signaling (Table 4; FIGS. 1A-1F). Western blotting confirmed increased expression and activation of TGFβ signaling. Transduction of HUAEC with dominant negative FGFR1 or FRS2 mutants resulted in a similar increase in TGFβ signaling and smooth muscle/mesenchymal marker expression (FIGS. 10A-10F).

TABLE 4 mRNA expression profiles in HUAECs after FRS2 knockdown

| Genes Up-Regulated | (Fold Change) FRS2 shRNA/Controls |
|---|---|
| BMP4 | 5.26 |
| TGFβ1 | 6.3 |
| TGFβ2 | 53.3 |
| IGF1 | 147.65 |
| IGFBP3 | 244.89 |
| COL1A1 | 28.56 |
| COL1A2 | 5.01 |
| COL3A1 | 6.76 |

To confirm the relevance of our findings beyond the primary EC, FRS2 was knocked down in primary human mammary epithelial cells (HuMEC) that are typically used in EMT studies. mRNA expression profiles were assessed using quantitative PCR arrays with cDNA from control or FRS2 knockdown cells. Genes with a statistically significant up-regulation greater than 5-fold are shown in Table 5. Similar to observations in EC, FRS2 knockdown in HuMEC resulted in the change from the normal rounded epithelial cell to a spindle-like mesenchymal phenotype, increased expression of mesenchymal markers including vimentin, N-cadherin, snail, ZEB1 (zinc finger E-box binding homeobox 1) and ZEB2, and decreased expression of EMT repressor miRNAs mir-200b and mir-200c (FIGS. 11A-11M). FRS2 knockdown in human foreskin and atrial cells also resulted in increased TGFβ signaling (FIGS. 12A-12H). Collectively, these data support the hypothesis that basal FGF signaling inhibits TGFβ-mediated Endo-MT.

TABLE 5 mRNA expression profiles in HuMECs after FRS2 knockdown

| Genes Up-Regulated During EMT | (Fold Change) FRS2 shRNA/Control |
|---|---|
| CDH2 | 5.4 |
| MMP3 | 22.82 |
| SNAI1 | 12.4 |
| ZEB1 | 14.95 |
| ZEB2 | 14.05 |

Figures 2A, 2B, 2C, 2D, 2E, 2F:
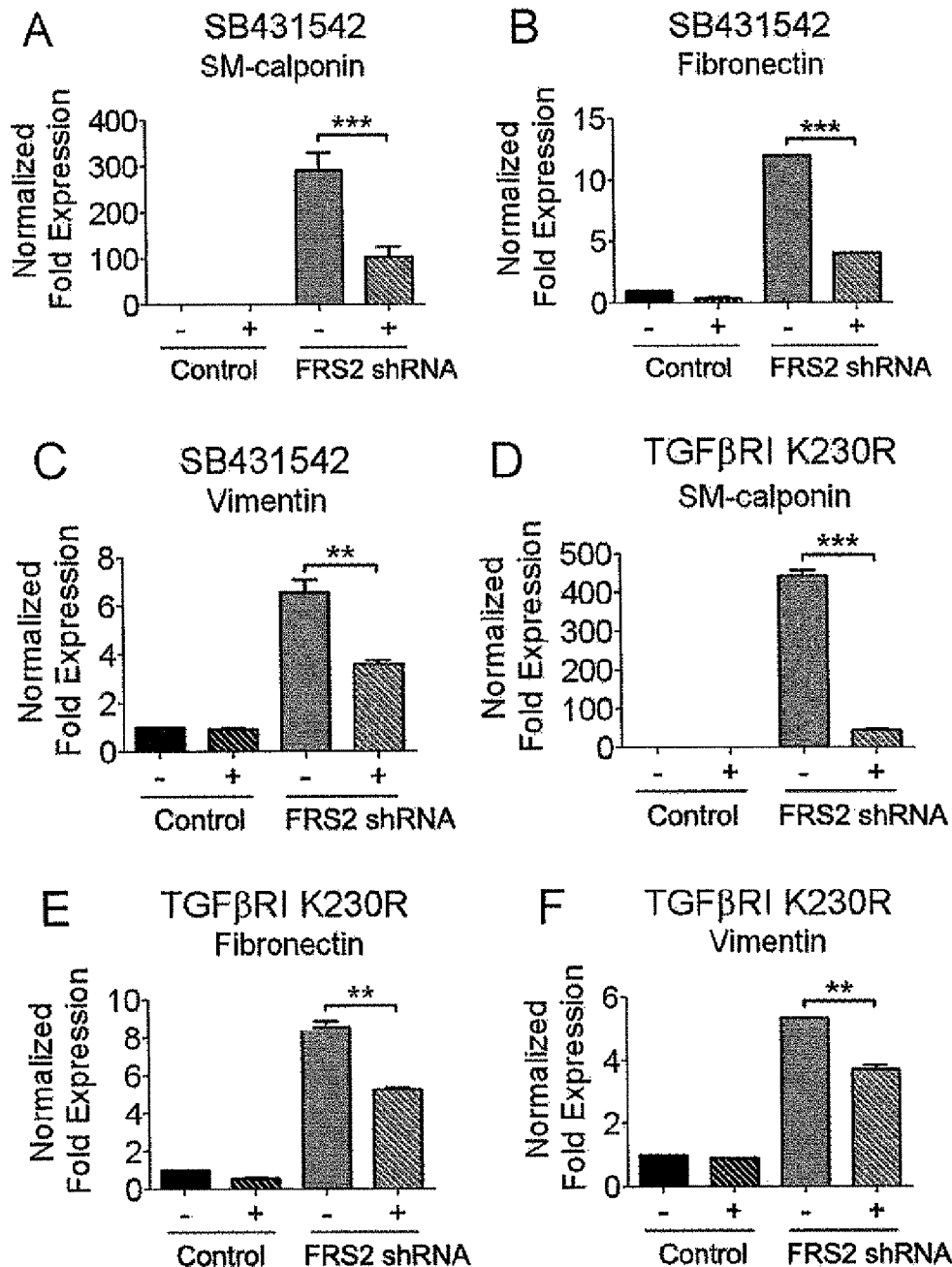
FIGS. 2A-2I are bar graphs showing qRT-PCR mRNA expression (normalized fold expression) of SM-calponin (FIGS. 2A, 2D, 2G), Fibronectin (FIGS. 2B, 2E, 2H), and Vimentin (FIGS. 2C, 2F, 2I) in ECs treated with the TGFβR1 inhibitor SB431542 (FIGS. 2A-2C), transduced with the dominant negative TGFβR1 construct TGFβR1 K230R (FIGS. 2D-2F), or treated with Smad2 shRNA (FIGS. 2G-2I). $p<0.01$; $*p<0.001$; NS: not significant compared to control.
Figures 2G, 2H, 2I:
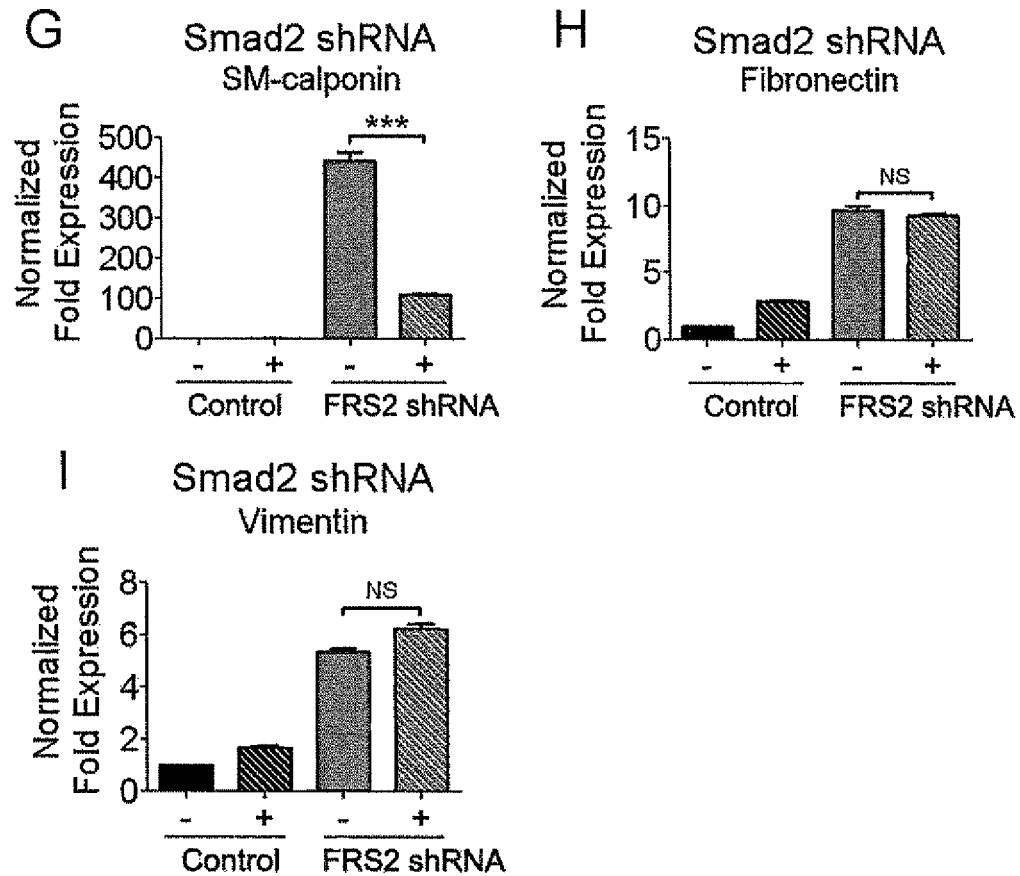

To demonstrate that activation of TGFβ signaling following FRS2 knockdown is indeed necessary for Endo-MT, three different experimental approaches were used to silence it. Treatment of FRS2 knockdown EC with TGFβR1 inhibitor SB431542 significantly decreased SM-calponin, fibronectin and vimentin expression (FIGS. 2A-2C). Similar results were seen after transduction of a dominant negative TGFβR1 construct (TGFβR1 K230R) (FIGS. 2D-2F). Finally, since SMAD2 activation was detected following FRS2 knockdown, its expression was silencing using a specific shRNA. This resulted in a significant decrease in SM-calponin, but not in fibronectin and vimentin expression (FIGS. 2G-2I).

Example 2

Figures 3A, 3B:
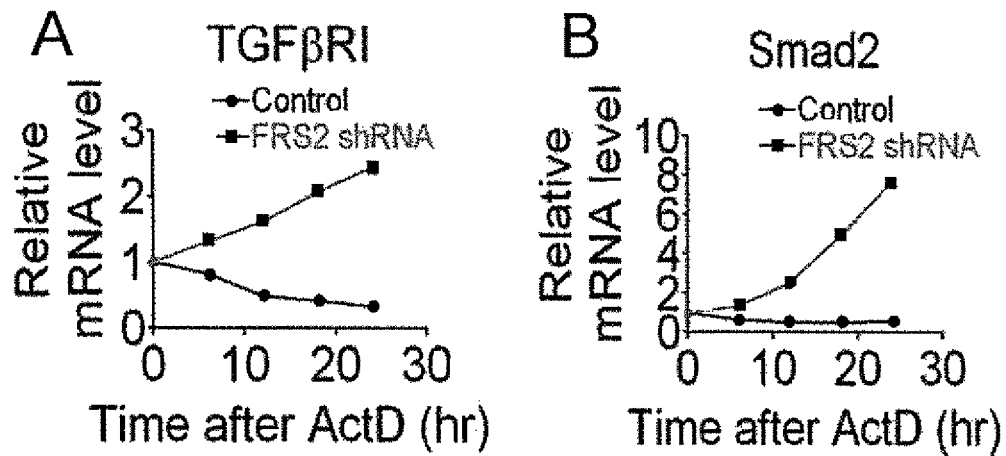
FIGS. 3A-3B are graphs showing qRT-PCR mRNA expression (relative mRNA level) of TGFβRI (FIG. 3A) and Smad2 (FIG. 3B) as a function of time (hr) after 10 μg/ml actinomycin D (ActD) in HUAEC treated with control (-○-) or FRS2 shRNA (-■-).
Figure 3C:
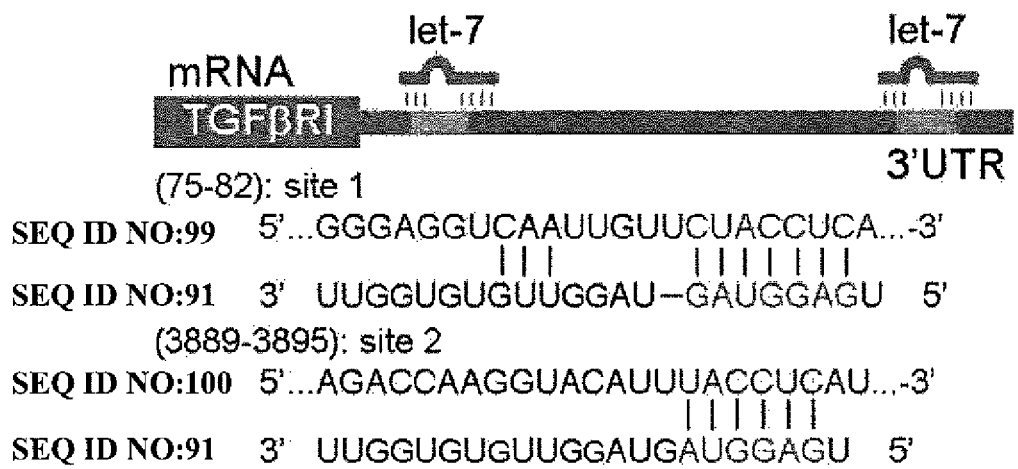
FIGS. 3C-3D show alignment of let-7 sequences with the 3'ITRs of the human TGFβR1 and Smad2.
Figure 3D:
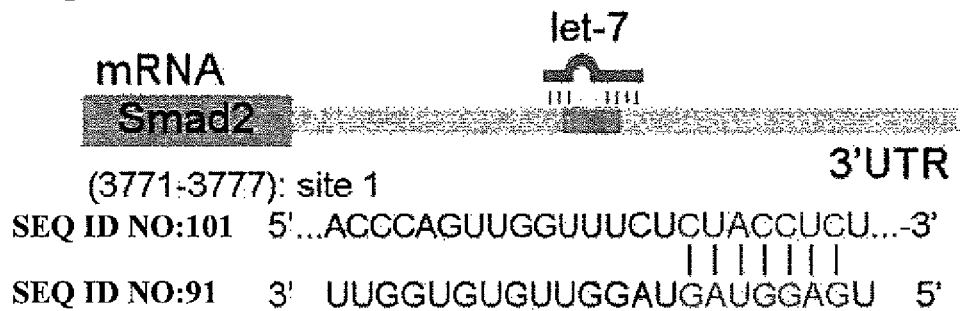
Figures 3E, 3F, 3G, 3H, 3I, 3J:
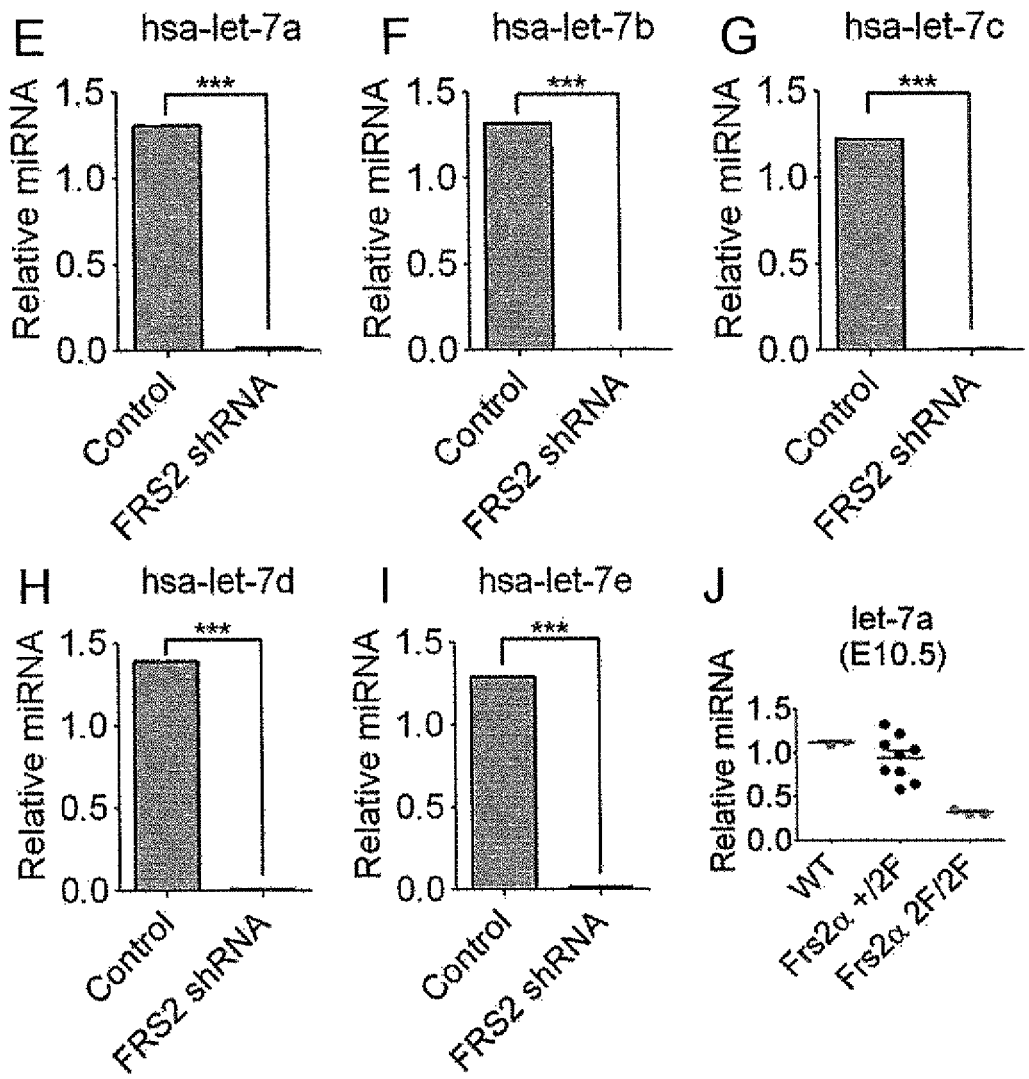
FIGS. 3E-3J are bar graphs showing qRT-PCR miRNA expression (relative expression) of hsa-let-7a (FIG. 3E), hsa-let-7b (FIG. 3F), has-let-7c (FIG. 3G), hsa-let-7d (FIG. 3H), hsa-let-7e (FIG. 3I) and let-7a (3J) in HUAEC treated with control (left bars) or FRS2 shRNA (right bars).
Figures 3K, 3L, 3M, 3N, 3O, 3P:
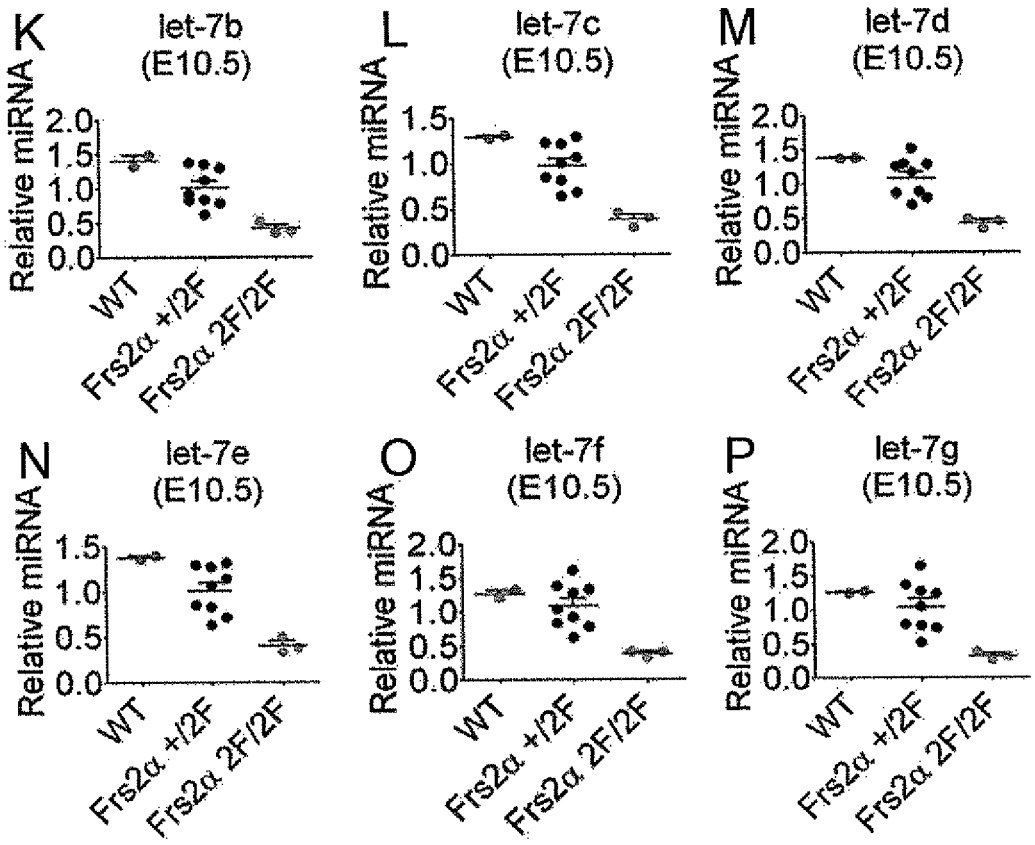
FIGS. 3K-3P are plots showing qRT-PCR miRNA expression (relative expression) of let-7b (FIG. 3K), let-7c (FIG. 3L), let-7d (FIG. 3M), let-7e (FIG. 3N), let-7f (FIG. 3O), and let-7g (FIG. 3P) in E10.5 wild-type (first row), FRS2α +/2F (second row), and FRS2α 2F/2F (third row) embryos. Each dot on the graphs represents one embryo.

FGF Signaling Regulates TGFβR1 mRNA Stability Via Regulation of Let7 miRNA Expression Next, the mechanism responsible for increased TGFβR1 and SMAD2 expression following FGF signaling shutdown was examined. Quantitative analyses of TGFβR1 and Smad2 mRNA half-life showed a marked increase following a knockdown of FRS2 expression (FIGS. 3A-3B). This indicates the presence of miRNA regulating the stability of these messages. In silico analysis of TGFβR1 and Smad2 messages identified binding sites for let-7 family of miRNAs (SEQ ID NO:91) with an exact match to the seed sequence of let-7 in TGFβR1 3'-UTR 75-82 (SEQ ID NO:99) and 3889-3895 (SEQ ID NO:100) and in Smad2 3'-UTR 3771-3777 (SEQ ID NO:101) downstream from the stop codon. miRNA array analysis demonstrated a 24 to 120 fold reduction in expression of all let-7 family members following FRS2 knockdown that was confirmed by qPCR (FIGS. 3C-3H, Table 6).

TABLE 6 mRNA expression of let-7 after FRS2 knockdown

| let-7 family | (Fold Change) FRS2 shRNA/Control |
|---|---|
| hsa-let-7a | −26.26 |
| hsa-let-7b | −108.01 |
| hsa-let-7c | −119.84 |
| hsa-let-7d | −37.66 |
| hsa-let-7e | −41.5 |
| hsa-let-7f | −23.83 |
| hsa-let-7g | −24.34 |
| hsa-let-7i | −66.49 |

To confirm that FGF signaling controls let-7 miRNA expression, mouse embryos with defective FGF signaling were examined following a knock-in of a mutant FRS2α construct (FRS2α 2F/2F). A gene dosage-dependent reduction in let-7 levels was observed (FIGS. 3H-3N).

Example 3

Let-7 Regulates TGFβR1 Expression in Endothelial Cells

Materials and Methods

In Vivo Let-7 Antagomir Delivery

Mice were administrated with either phosphate buffered saline (PBS) or AF12 complexes at 2 mg/kg body weight in 0.2 ml per injection via lateral tail vein. Measurements of miRNA or mRNA levels in endothelial cells were performed 6 days after the injection.

Results

Figure 4A:
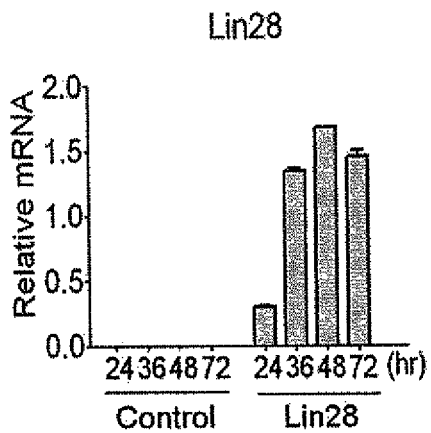
FIG. 4A is a graph showing qRT-PCR miRNA expression (relative mRNA level) of Lin28 in HUAEC 24 hr (rows 1 and 5), 36 hr (rows 2, and 6), 48 hours (rows 3 and 7) or 72 hours (rows 4 and 8) after transduction with an empty vector (rows 1-4) or a vector expressing lin28 (rows 5-8).
Figures 4B, 4C, 4D, 4E:
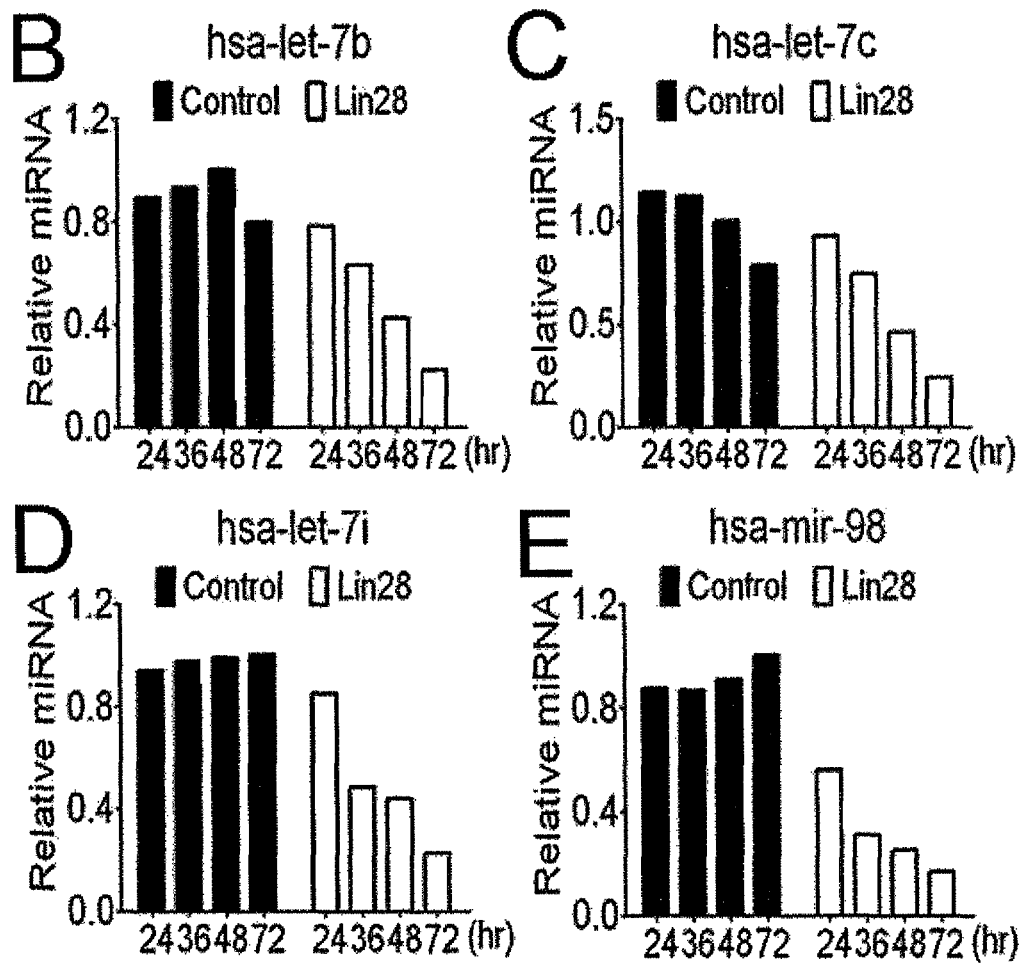
FIGS. 4B-4E are bar graphs showing qRT-PCR miRNA expression (relative mRNA level) of hsa-let-7b (FIG. 4B), has-let-7c (FIG. 4C), hsa-let-7i (FIG. 4D), and hsa-mir-98 (FIG. 4E) in HUAEC 24 hr (rows 1 and 5), 36 hr (rows 2, and 6), 48 hours (rows 3 and 7) or 72 hours (rows 4 and 8) after transduction with an empty vector (rows 1-4) or a vector expressing lin28 (rows 5-8).
Figure 4F:
FIG. 4F is an illustration of the let-7 sponge decoy.
Figures 4G, 4H:
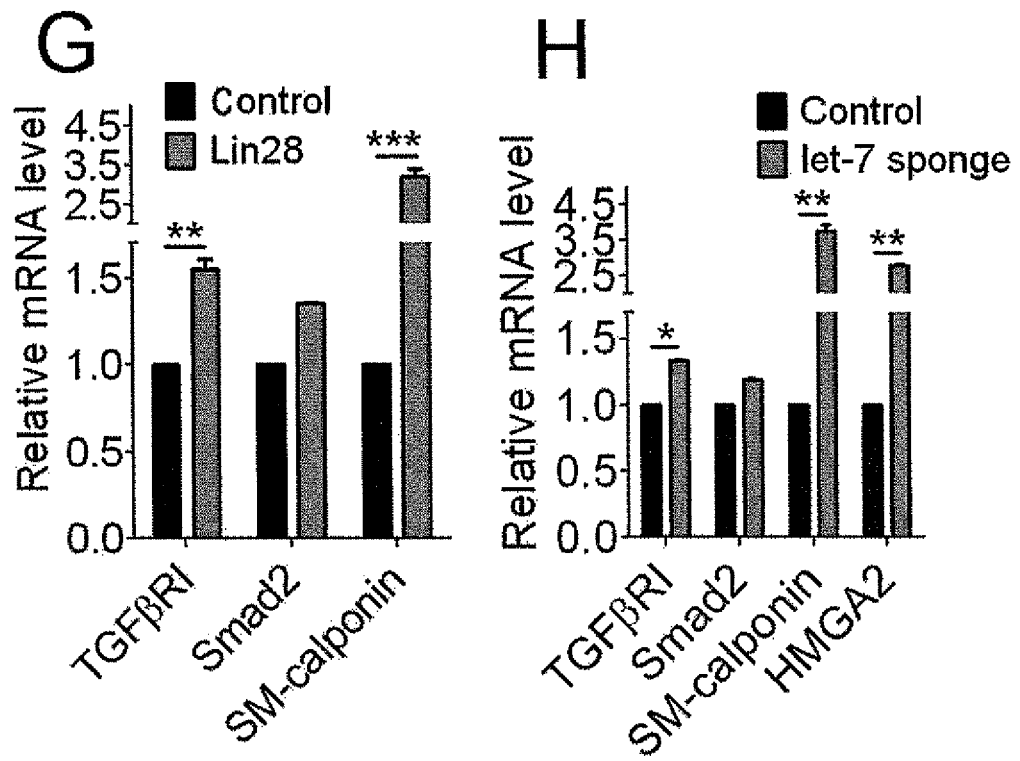
FIG. 4G is a bar graphs showing qRT-PCR mRNA expression (relative mRNA level) of TGFβRI (rows 1 and 2), Smad2 (rows 3 and 4), and SM-calponin (rows 5 and 6) in control (sold bars) and lin28 overexpressing (shaded bars) HUAEC.
FIG. 4H is a bar graphs showing qRT-PCR mRNA expression (relative mRNA level) of TGFβRI (rows 1 and 2), Smad2 (rows 3 and 4), SM-calponin (rows 5 and 6), and HMGA2 (rows 7 and 8) in control (solid bars) or let-7 sponge overexpressing (shaded bars) HUAEC.
Figures 4I, 4J, 4K:
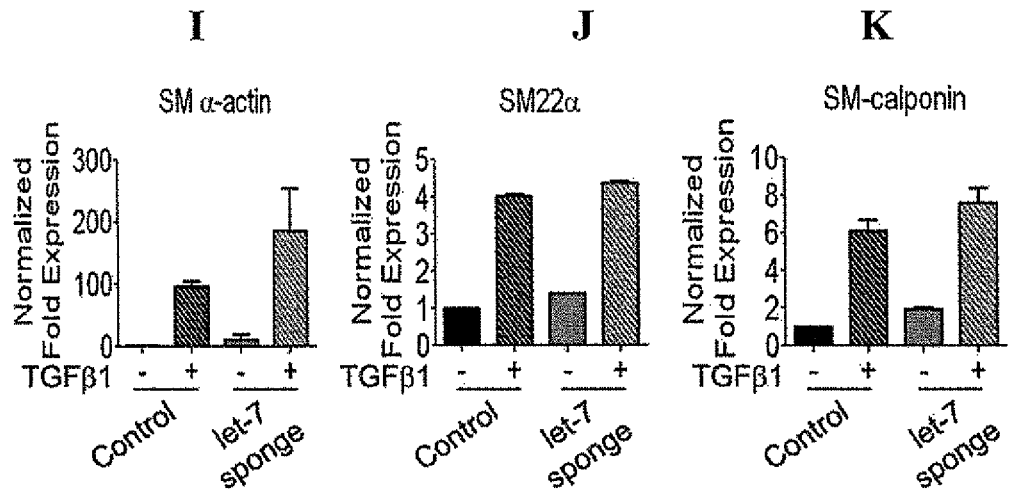
FIGS. 4I-4K are bar graphs showing qRT-PCR mRNA expression (relative mRNA level) of SM α-actin (FIG. 4I), SM22α (FIG. 4J), and SM-calponin (FIG. 4K) in control (rows 1 and 2)) or let-7 sponge overexpressing (rows 3 and 4) HUAEC untreated (−, rows 1 and 2) or treated with TGFβ1 (+, rows 2 and 4).

To further explore let-7 role in regulation of TGFβ signaling, the expression of let-7 family members was inhibited in an FGF-independent manner. Transfection of Lin28 (FIG. 4A), a known inhibitor of let-7 biogenesis (Viswanathan S R and Daley G Q. Cell. 140(4):445 (2010)) resulted in a profound reduction of let-7b and 7c expression and an increase in TGFβ1 and smooth muscle expression (FIGS. 4B-4F). Similarly, viral transduction of a let-7 "sponge" (Table 7; FIG. 4E) into EC led to a marked increase in TGFβR1 expression and appearance of Endo-MT markers expression (FIGS. 4H-4K).

TABLE 7 sequences in let-7 sponge decoy

| let-7 family | Sequence (5' → 3') | |
|---|---|---|
| hsa-let-7a | UGAGGUAGUAGGUUGUAUAGUU | SEQ ID NO: 90 |
| hsa-let-7b | UGAGGUAGUAGGUUGUGUGGUU | SEQ ID NO: 91 |
| hsa-let-7c | UGAGGUAGUAGGUUGUAUGGUU | SEQ ID NO: 92 |
| hsa-let-7d | UGAGGUAGUAGGUUGCAUAGU | SEQ ID NO: 93 |
| hsa-let-7e | UGAGGUAGGAGGUUGUAUAGU | SEQ ID NO: 94 |
| hsa-let-7f | UGAGGUAGUAGAUUGUAUAGUU | SEQ ID NO: 95 |
| hsa-let-7g | UGAGGUAGUAGUUUGUACAGU | SEQ ID NO: 96 |
| hsa-let-7i | UGAGGUAGUAGUUUGUGCUGU | SEQ ID NO: 97 |
| mir-98 | UGAGGUAGUAAGUUGUAUUGUU | SEQ ID NO: 98 |

Figure 4L:
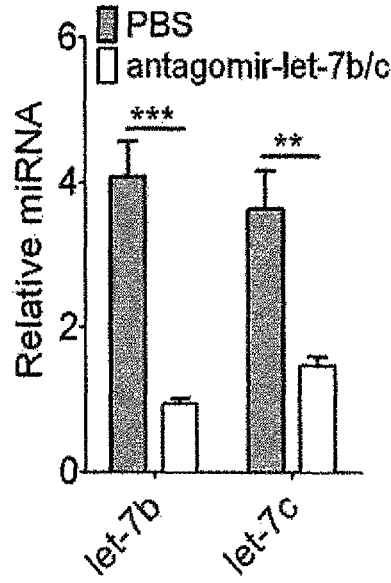
FIG. 4L is a bar graph showing qRT-PCR miRNA expression (relative mRNA level) of let-7b (rows 1 and 2) or let-7c (rows 3 and 4) in liver endothelial cells of mice injected intravenously with PBS (shaded bars) or a single injection of 2 mg/kg cholesterol formulated antagomir-let-7b/c (open bars) that were isolated at 6 days. n=5 mice in each group.
Figure 4M:
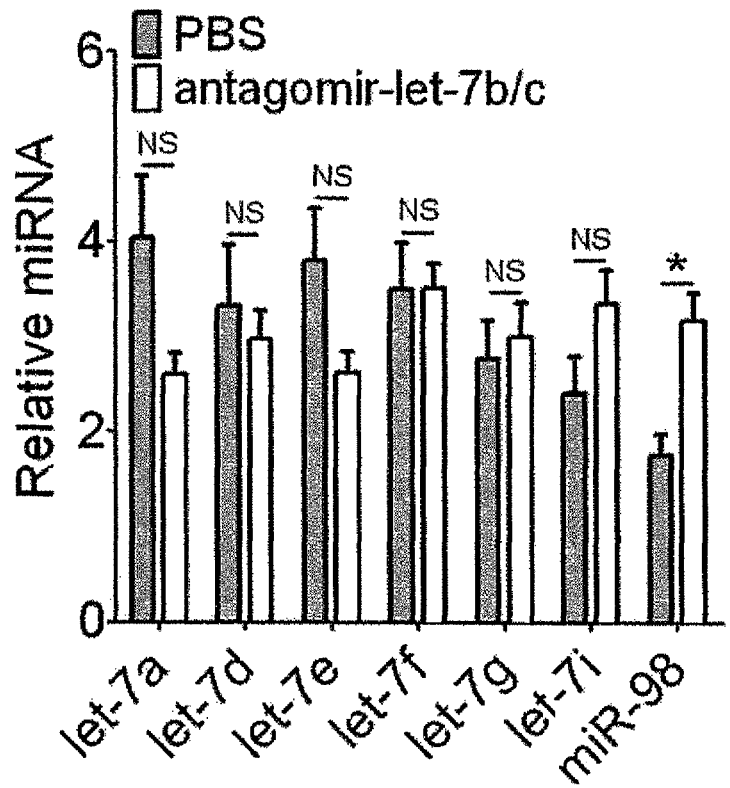
FIG. 4M is a bar graph showing qRT-PCR miRNA expression (relative mRNA level) of let-7a (rows 1 and 2), let-7d (rows 3 and 4), let-7e (rows 5 and 6), let-7f (rows 7 and 8), let-7g (rows 9 and 10), let-7i (rows 11 and 12), miR-98 (rows 13 and 14) in liver endothelial cells of mice injected intravenously with PBS (shaded bars) or a single injection of 2 mg/kg cholesterol formulated antago-mir-let-7b/c (open bars) that were isolated at 6 days. n=5 mice in each group.
Figure 4N:
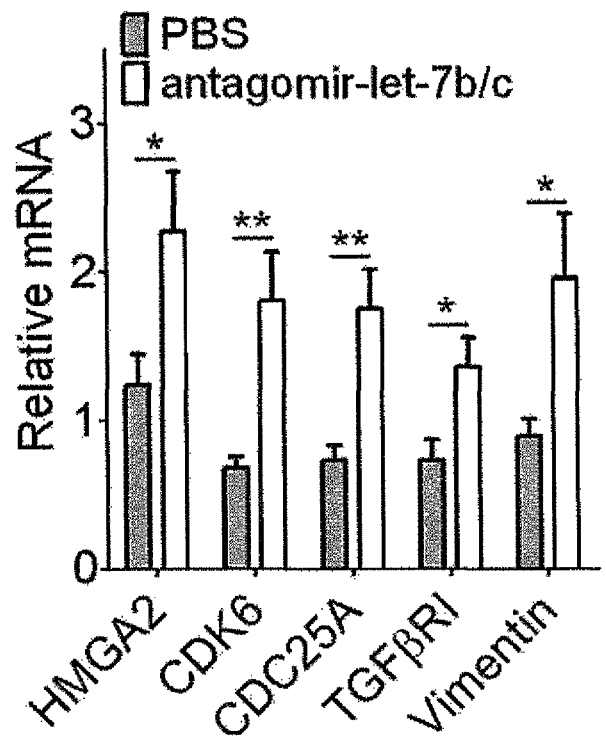
FIG. 4N is a bar graph showing qRT-PCR miRNA expression (relative mRNA level) of HMGA2 (rows 1 and 2), CDK6 (rows 3 and 4), CDC25A (rows 5 and 6), TGFβR1 (rows 7 and 8), and Vimentin (rows 9 and 10) in liver endothelial cells of mice injected intravenously with PBS (shaded bars) or a single injection of 2 mg/kg cholesterol formulated antagomir-let-7b/c (open bars) that were isolated at 6 days.

To determine the in vivo relevance of let-7 inhibition in the regulation of TGFβRI, let-7b and let-7c miRNAs were directly targeted in mice using cholesterol formulated antagomirs for improved stability and endothelial cell delivery. A single tail vein injection of 2 mg/kg of cholesterol-formulated let-7b/c antagomirs did not produce any alterations in mice's overall health, body weight or food intake. Six days later the animals were sacrificed and let-7 family expression was determined in freshly isolated primary liver EC. There was a significant reduction in expression of let-7b and let-7c miRNA in EC from antagomirs-treated compared to control mice (FIG. 4L). At the same time, there was no change in expression of other let-7 family members (FIG. 4M). This reduction in let-7b/c levels was confirmed by increased expression of known let-7 target genes HMGA2, CDK6, and CDC25A (FIG. 4N). Finally, let-7b/c antagomirs-treated mice EC demonstrated a significant increase in TGFβRI and vimentin expression (FIG. 4N).

Figure 5A:
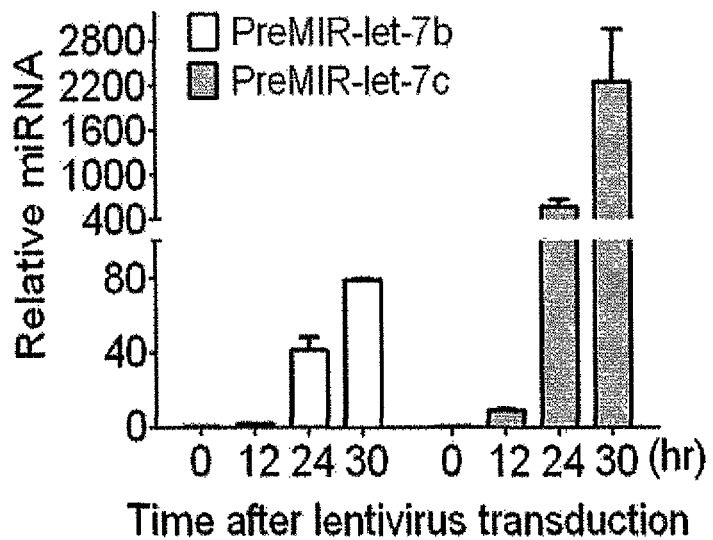
FIG. 5A is a bar graph showing qRT-PCR miRNA expression (relative mRNA level) of let-7b (open bars) and let-7c (shaded bars) in HUAEC 0 hrs (rows 1 and 5), 12 hrs (rows 2 and 6), 24 hrs (rows 3 and 7) and 30 hours (rows 4 and 8)
Figures 5B, 5C, 5D, 5E, 5F, 5G, 5H, 5I:
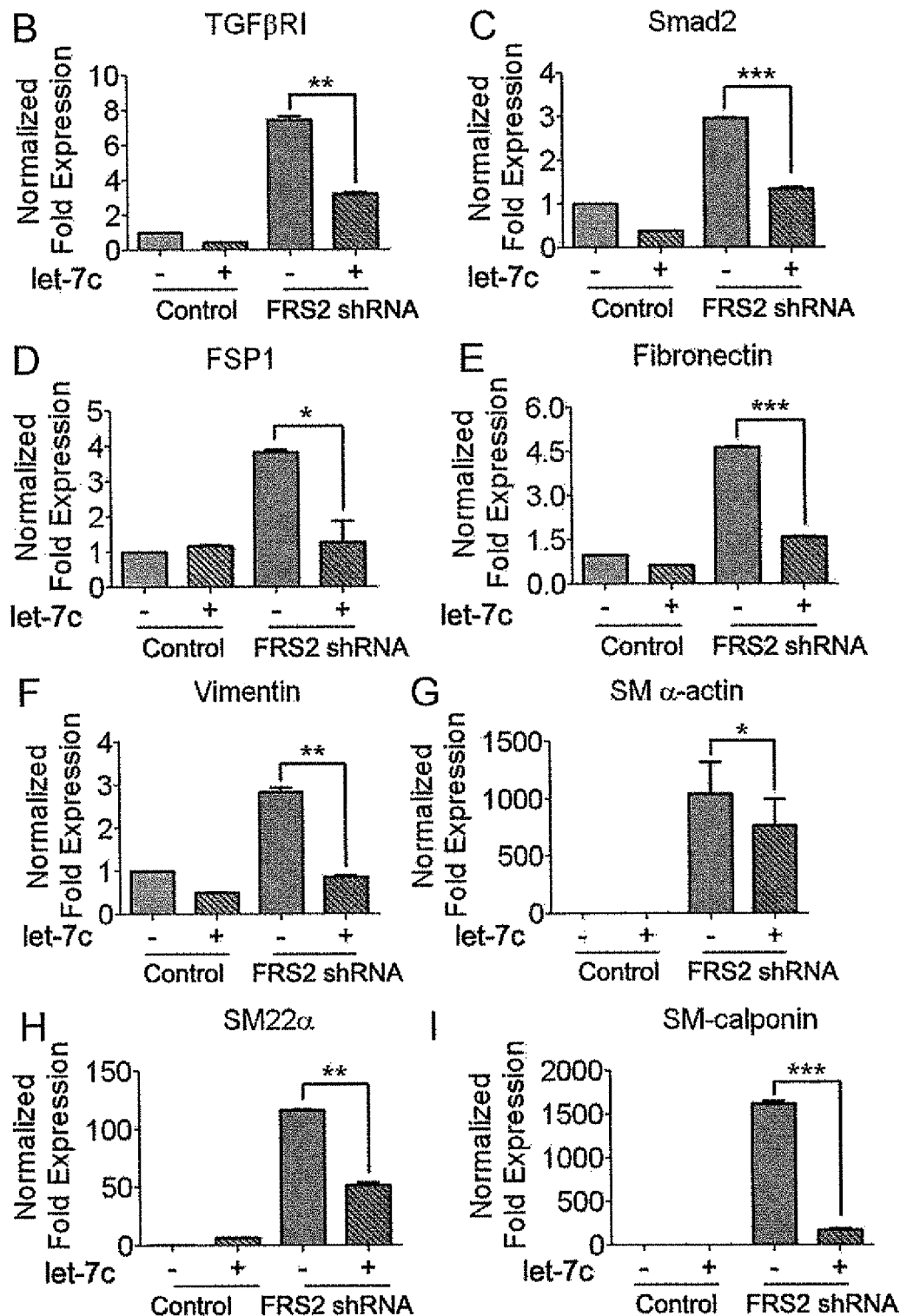
FIGS. 5B-5I are bar graphs showing qRT-PCR mRNA expression (relative mRNA level) of TGFβRI (FIG. 5B), Smad2 (FIG. 5C), FSP1 (FIG. 5D), Fibronectin (FIG. 5E), Vimentin (FIG. 5F), SM α-actin (FIG. 5G), SM22α (FIG. 5H), and SM-calponin (FIG. 5I) in control (rows 1 and 2) and FRS2 knockdown (rows 3 and 4) HUAEC cells transduced with empty vector (rows 1 and 3) or a lentiviruses expressing let-7c (rows 2 and 4). $*p<0.05$; $p<0.01$; $*p<0.001$ compared to control.
Figures 6A, 6B, 6C, 6D, 6E, 6F, 6G:
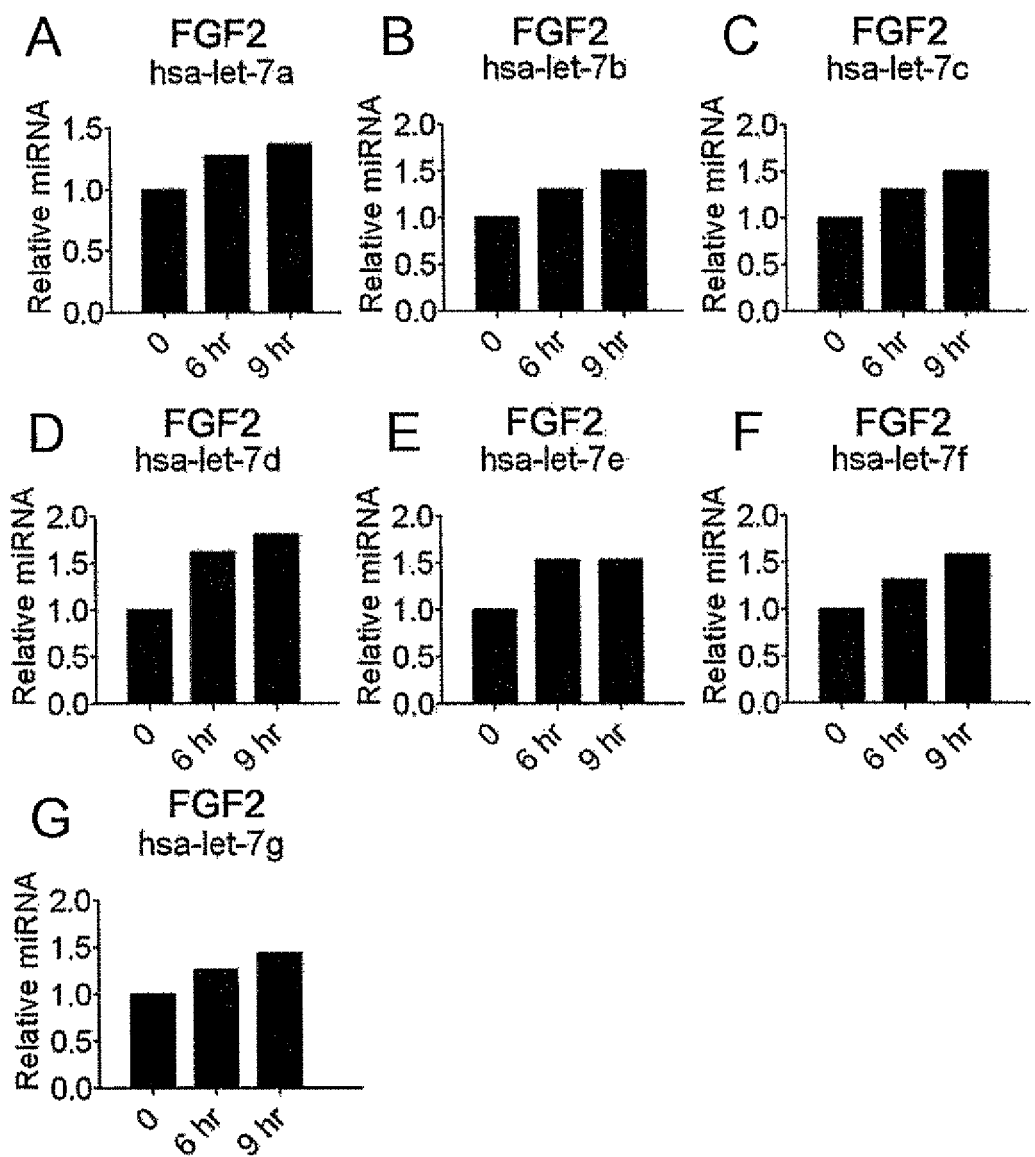
FIGS. 6A-6G are bar graphs showing qRT-PCR miRNA expression (relative mRNA level) of hsa-let-7a (FIG. 6A), hsa-let-7b (FIG. 6B), hsa-let-7e (FIG. 6C), hsa-let-7d (FIG. 6D), hsa-let-7e (FIG. 6E), hsa-let-7f (FIG. 6F), and hsa-let-7g (FIG. 6G) in HUAEC 0 hrs (row 1), 6 hrs (row 2), and 9 hrs (row 3) after FGF2 treatment.
Figures 6H, 6I, 6J, 6K, 6L, 6M:
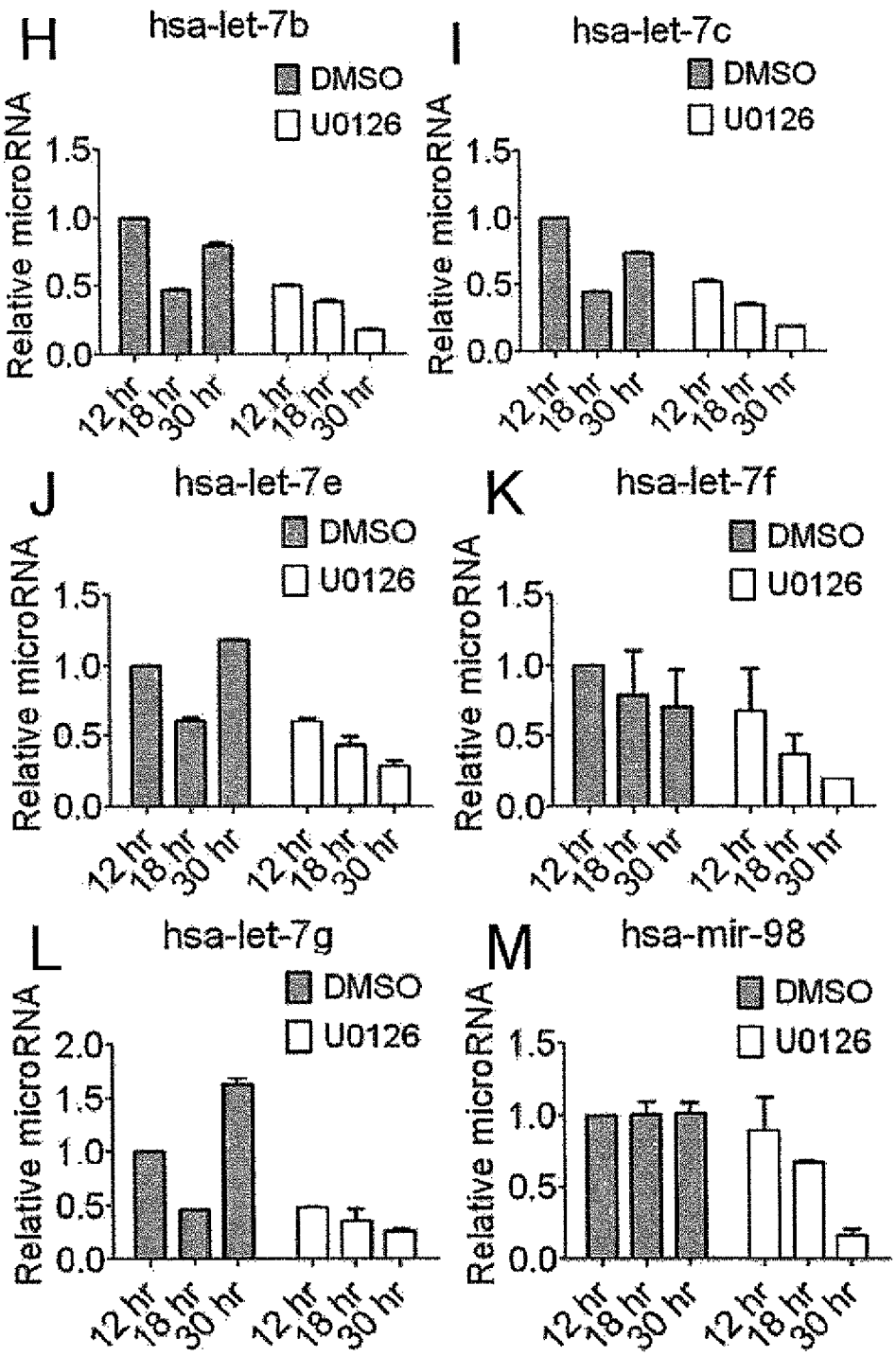
FIGS. 6H-6M are bar graphs showing qRT-PCR miRNA expression (relative mRNA level) of hsa-let-7b (FIG. 6H), hsa-let-7c (FIG. 6I), hsa-let-7e (FIG. 6J), hsa-let-7f (FIG. 6K), hsa-let-7g (FIG. 6L), and hsa-mir-98 (FIG. 6M) in HUAEC 12 hrs (rows 1 and 4), 18 hrs (row 2 and 5), and 30 hrs (row 3 and 6) after treatment with DMSO control (shaded bars) or U0126 (solid bars).
Figure 6N:
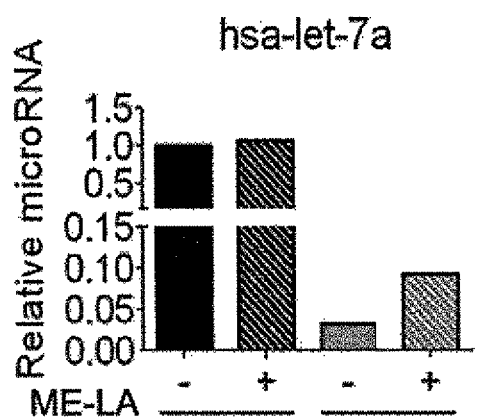
FIGS. 6N-6Q are bar graphs showing qRT-PCR miRNA expression (relative mRNA level) of hsa-let-7a (FIG. 6N), hsa-let-7b (FIG. 6O), hsa-let-7c (FIG. 6P), and hsa-let-7e (FIG. 6Q) in control (rows 1 and 2) and FRS2 knockdown (rows 3 and 4) HUAEC transduced with an empty vector (−, rows 1 and 3) or with a constitutively active ERK (Ad-ME-LA) (+, rows 2 and 4).
Figure 6O:
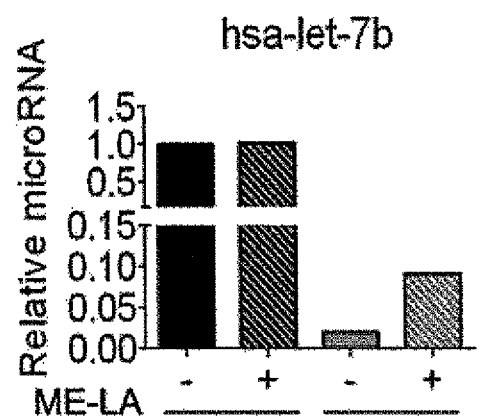
Figure 6P:
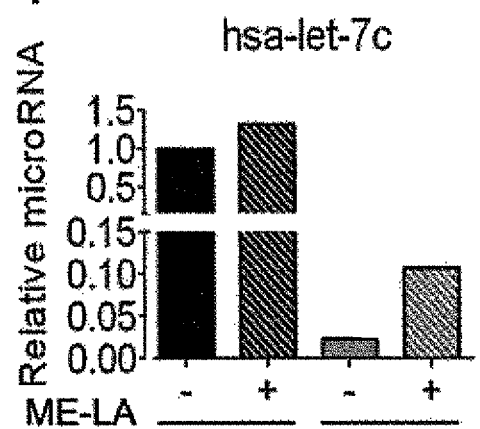
Figure 6Q:
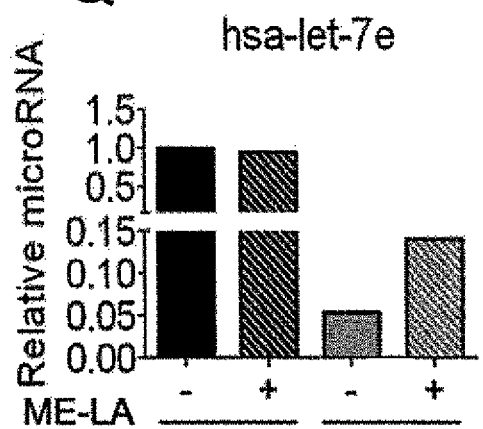

While reduction in Let-7b/c expression induced Endo-MT, expression of these miRNAs in primary EC in vitro following FRS2 knockdown (FIG. 5A) fully inhibited TGFβR1 and SMAD2 expression and prevented activation of TGFβ signaling. As a result, expression of all SMC and mesenchymal markers declined to pre-FRS2 knockdown levels (FIGS. 5B-5I).

To gain an insight into the molecular mechanism by which FGF controls let-7 expression, it was next determined whether FGF stimulation of normal EC affects its levels. FGF2 treatment of EC resulted in a time dependent increase in expression of all let-7 family miRNAs (FIGS. 6A-6G). Since FGFR1/FRS2 complex primarily activates the ERK1/2 pathway (Gotoh N, et al. *Proc Natl Acad Sci USA*. 101(49):17144 (2004)), the role of ERK1/2 in regulation of let-7 expression was investigated. Treatment of EC with a MEK inhibitor U0126 led to a decrease in let-7 expression (FIGS. 6H-6M). To determine if ERK activation can restore let-7 expression in EC with suppressed FGF signaling, EC subjected to FRS2 knockdown were transduced with an adenoviral vector encoding a constitutively active ERK (Ad-ME-LA) (Robinson M J, et al. *Curr Biol*. 8(21):1141 (1998)) or LacZ control. Transduction of Ad-ME-LA, but not of LacZ, increased let-7 expression, suppressed activation of TGFβ signaling including inhibition of Smad2 phosphorylation, and inhibited smooth muscle genes expression (FIG. 6N-6Q), indicating that regulation of TGFβ signaling by FGF is mediated by activation of the Erk1/2-dependent signaling mechanism.

Example 4

TGFβ-Mediated Endo-MT Plays a Role in Vascular Graft Stenosis

Materials and Methods
Scaffold Fabrication & TEVG Implantation

Scaffolds were constructed from a nonwoven polyglycolic acid (PGA) mesh (Concordia Fibers) and a co-polymer sealant solution of poly-L-lactide and -ε-caprolactone (P(CL/LA)) as previously described (Roh J D, et al. *Biomaterials*. 29(10):1454 (2008)). For scaffold seeding studies, bone marrow was collected from the femurs of syngeneic C57BL/6 mice. Following purification of the mononuclear cell component using Histopaque-1086 (Sigma) centrifugation, one million mononuclear cells were manually pipetted onto the scaffold. The seeded scaffold was incubated in RPMI 1640 Medium (Gibco) overnight prior to implantation as previously described (Rob J D, et al. *Biomaterials*. 29(10):1454 (2008)). TEVG scaffolds were inserted into the infrarenal inferior vena cava (IVC) of 8-10 week old, female mice as previously described (Roh J D, et al. *Biomaterials*. 29(10):1454 (2008)).

In Vivo Microcomputed Tomography

Micro-CT imaging was performed using wild-type CB 17 mice at 10 weeks postoperatively as previously described using micro-CT scanner (eXplore CT120; GE Healthcare, USA).

sFGFR1-IIIc Adenovirus Administration sFGFR1-IIIc adenovirus was previously described (Murakami M, et al. *J Clin Invest*. 118(10):3355 (2008)) at a dose of $5 \times 10^{10}$ viral particles per mouse 1 week prior to TEVG implantation by tail vein injection. Control mice were given equivalent volumes of sterile PBS. Serum level of sFGFR1-IIIc was measured by a Human IgG Subclass Profile kit (Invitrogen).

Mouse Treatment with SB431542

Mice treated with TGFβRI kinase inhibitor were treated with SB431542 hydrate (Sigma) in DMSO given by intraperitoneal injection twice a day from post-operative day 0 to post-operative day 14 at a dose of 10 mg/kg. Control mice were treated with equivalent volumes of sterile DMSO.

TEVG Analysis

Explanted grafts were pressure fixed in 10% formalin overnight and then embedded in paraffin or glycolmethacrylate using previously published methods (Roh J D, et al. *Proc Natl Acad Sci USA*. 107(10):4669 (2010)). Sections were stained with H&E or Gomori Trichrome. Graft luminal diameters were measured using ImageJ software. Stenosis was defined as greater than 50% decrease in luminal diameter. Critical stenosis was defined as 80% narrowing of the luminal diameter. Graft occlusion was defined as 100% narrowing of the luminal diameter. For EM studies scaffolds were cut into 0.5 mm thick cross-sections and imaged on a FEI XL-30 scanning electron microscope (Hillsboro) as previously described (Roh J D, et al. *Biomaterials*. 29(10):1454 (2008)). TGFβ positive cell area was measured using ImageJ software. Two separate sections of each explant were counterstained with hematoxalin and imaged at 400× magnification. The number of nuclei was then counted in five regions of each section and averaged. LacZ/SMA colocalized cells were quantified in the same manner using double immunofluorescent staining imaged under 60× confocal magnification.

Tamoxifen Administration 100 mg tamoxifen (Sigma) was dissolved in 5 ml corn oil (20 mg/ml final concentration). The solution was mixed at 37° C. overnight. Pups were pipette fed with 0.05 mg/g tamoxifen solution every other day for 8 times.

Whole Mount X-Gal Staining

The expression of LacZ in scaffolds was detected by X-gal (β-glactosidase) staining using beta-gal staining kit according to the manufacturer's instructions (MILLIPORE). Following X-gal staining, the scaffolds were refixed, dehydrated, embedded in paraffin, and sectioned at 6 μm. The paraffin sections were then countered with eosin before being photographed.

Results

Figures 7A, 7B, 7C:
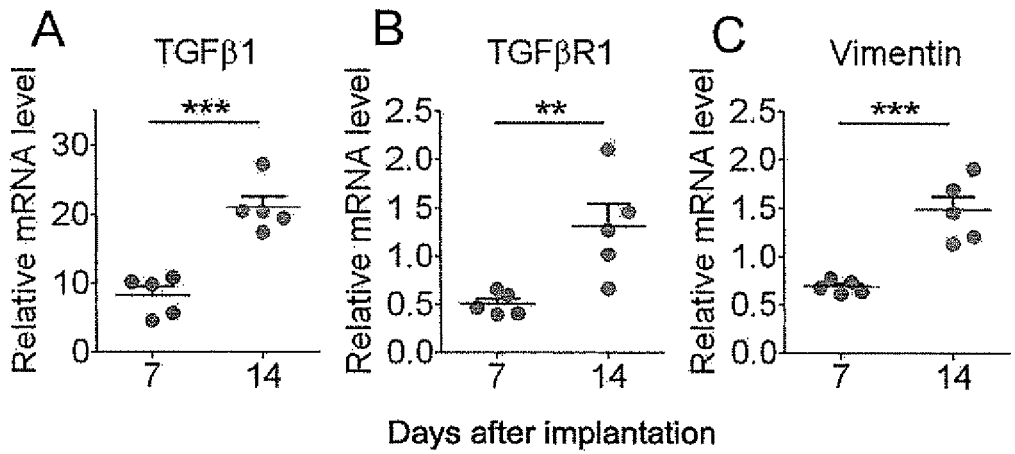
FIGS. 7A-7C are plots showing qRT-PCR mRNA expression (relative mRNA level) of TGFβ1 (FIG. 7A), TGFβRI (FIG. 7B), and vimentin (FIG. 7C) in occluded TEVG at day 7 (row 1) and day 14 (row 2). Each dot on graph represents gene expression level in one TEVG; $p<0.01$; $*p<0.001$ compared to control.

A tissue-engineered vascular graft (TEVG) stenosis model (Roh J D, et al. *Biomaterials*. 29(10):1454 (2008)) was used to examine whether Endo-MT plays a role in vivo. Following implantation into the inferior vena cava in an infrarenal position, TEVG develops extensive neointima composed of SMC and extracellular matrix leading to severe graft stenosis. Immunocytochemistry and qPCR analysis shows extensive deposition of TGFβ and increased TGFβ1, TGFβR1 and vimentin expression (FIGS. 7A-7C).

Figures 7D, 7E:
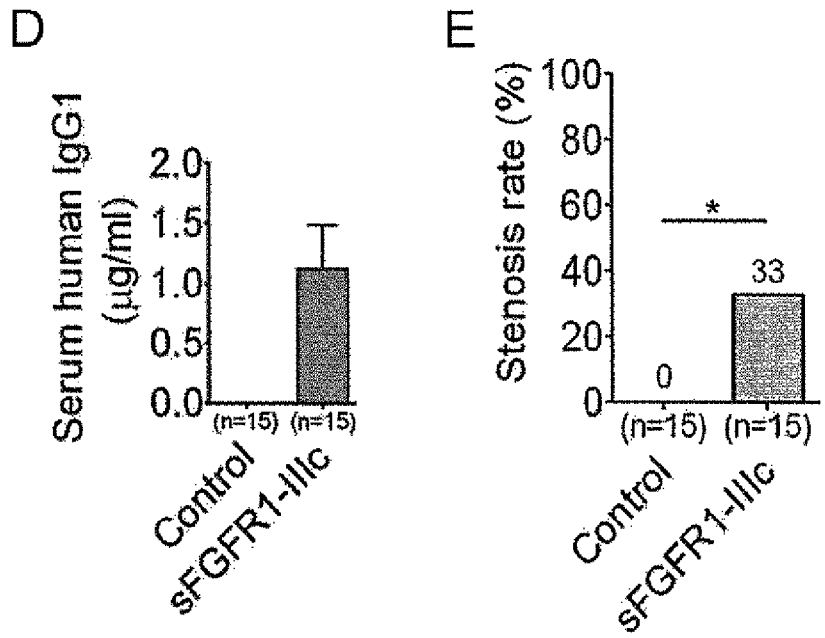
FIGS. 7D-7E are bar graphs showing TEVG stenosis rate (FIG. 7D) and serum IgG1 (µg/ml) (FIG. 7E) in control (row 1) and sFGFR1-IIIc treated (row 2) mice. Data shown represents mean±SD from 2 wells per group.

To determine if transcriptional regulation of TGFβR1 by FGF signaling plays a role in TEVG stenosis, a soluble FGF trap (sFGFR1-IIIc), which has been previously demonstrated to virtually shutdown FGF signaling (Murakami M, et al. *J Clin Invest*. 118(10):3355 (2008)), was systemically expressed one week before implantation of TEVG "seeded" with bone marrow mononuclear cells, a procedure known to dramatically improve the graft patency (Roh J D, et al. *Proc Natl Acad Sci USA*. 107(10):4669 (2010)). Two weeks after graft implantation, there were significantly higher TEVG neointima burden and stenosis rate in mice injected with Ad-sFGFR1-IIIc compared to saline-injected control mice (FIG. 7D-7E).

Figures 8A, 8B, 8C, 8D, 8E:
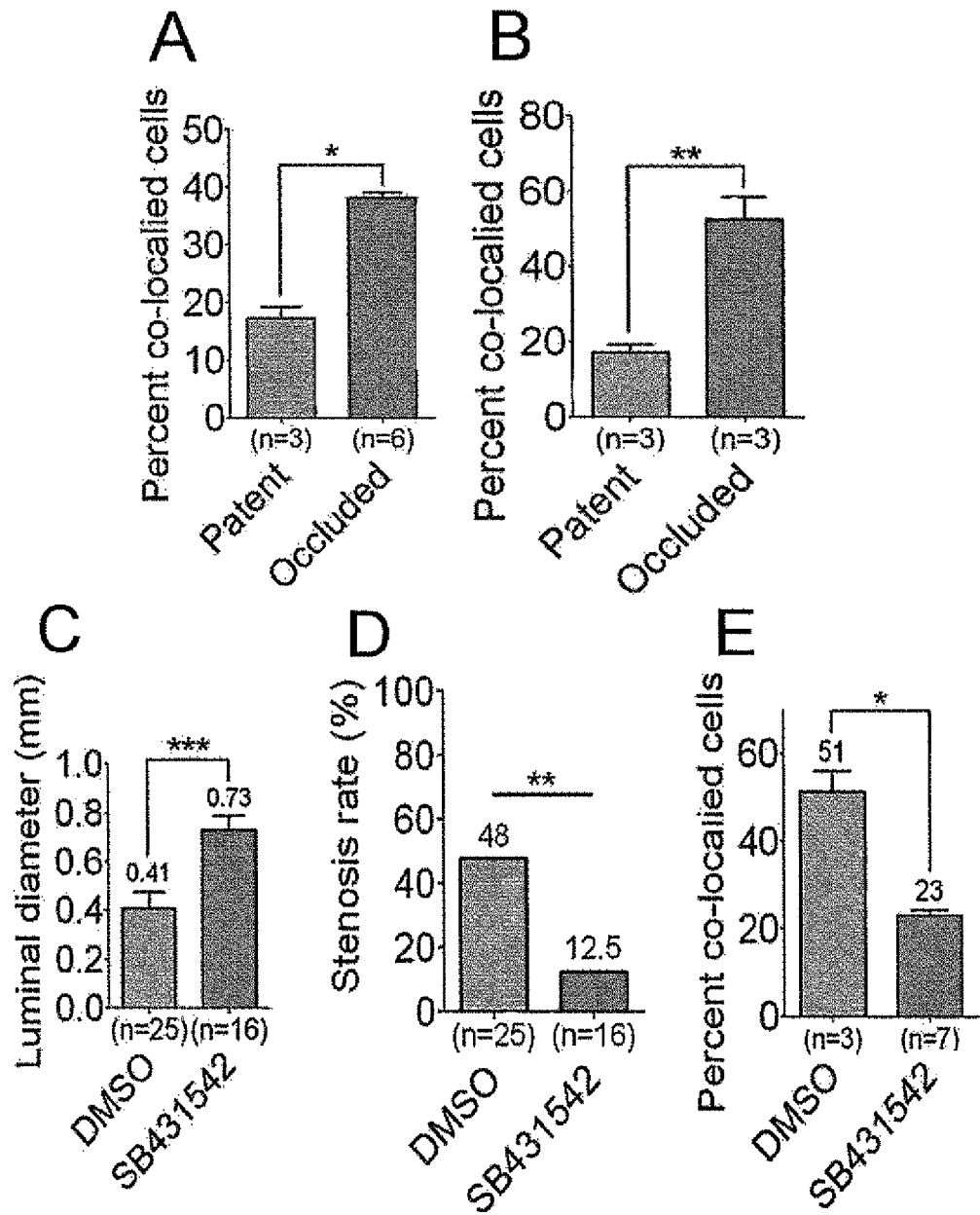
FIGS. 8A-8B are bar graphs showing the percentage of cells with co-localized LacZ and SM α-actin in patent (row 1) and occluded (row 2) neointimal cells following TEVG insertion in Tie2-Cre; RosaLacZ mice (FIG. 8A) and Cdh5-CreERT2; RosaLacZ mice (FIG. 8B), with the latter Cre activated by tamoxifen administration on day P2.
FIGS. 8C-8E are bar graphs showing luminal diameter (mm) (FIG. 8C), stenosis rate (%) (FIG. 8D), and percentage of cells with co-localized LacZ and SM α-actin (FIG. 8E) in Tie2-CreXRosa26 mice treated with DMSO (row 1) or the TGFβR1 inhibitor SB431542 (row 2) after TEVG implantation. Data are presented as mean±SD; $*p<0.05$; $p<0.01$; $*p<0.001$.
Figures 9A, 9B, 9C, 9D, 9E, 9F:
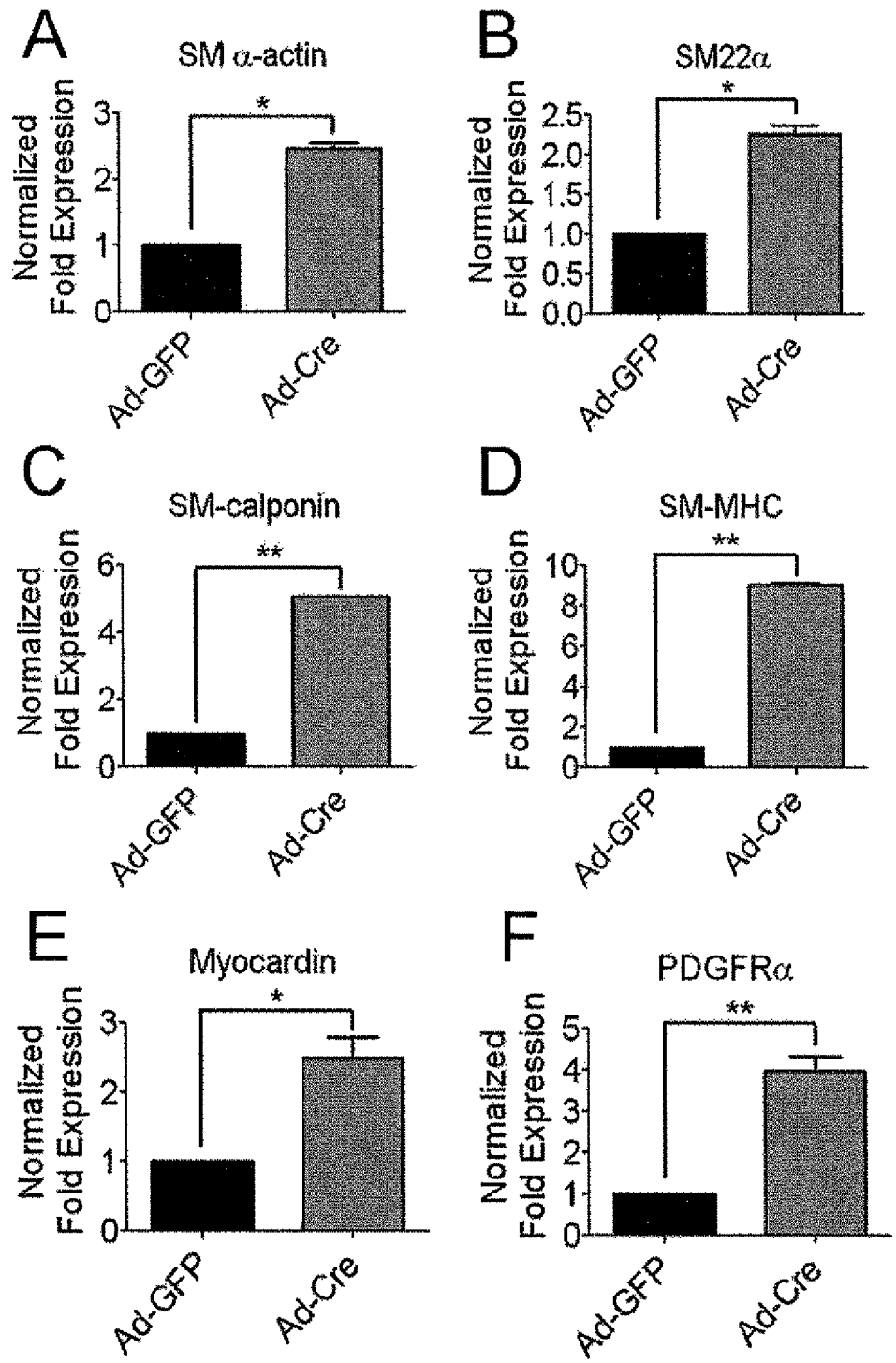
FIGS. 9A-9J are bar graphs showing qRT-PCR mRNA expression (relative mRNA level) of SM α-actin (FIG. 9A), SM22α (FIG. 9B), SM-calponin (FIG. 9C), SM-MHC (FIG. 9D), Myocardin (FIG. 9E), PDGFRα (FIG. 9F), PDGFRβ (FIG. 9G), Vimentin (FIG. 9H), NG2 (FIG. 9I), and Runx1 (FIG. 9J) in primary mouse endothelial cells transduced with adenovirus-GFP (sold bars) or adenovirus-Cre (shaded bars) at 4 days. $*p<0.05$; $p<0.01$; $*p<0.001$.
Figures 9G, 9H, 9I, 9J:
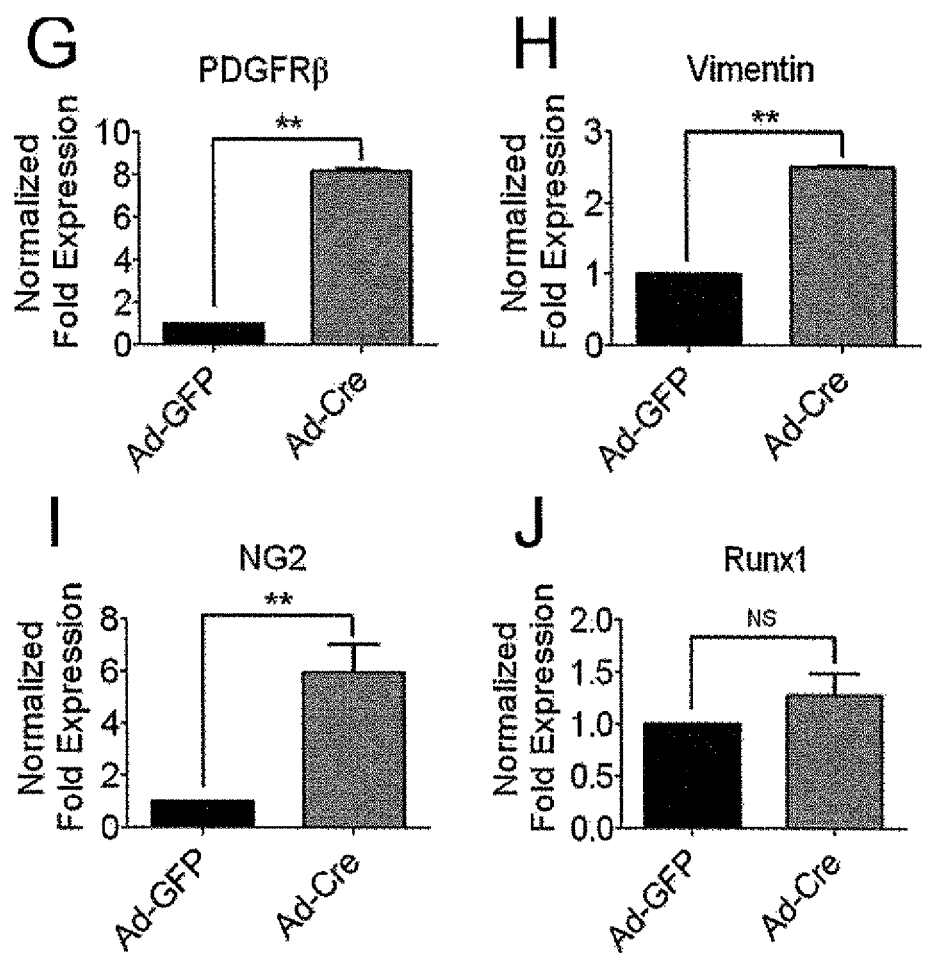
Figure 10A:
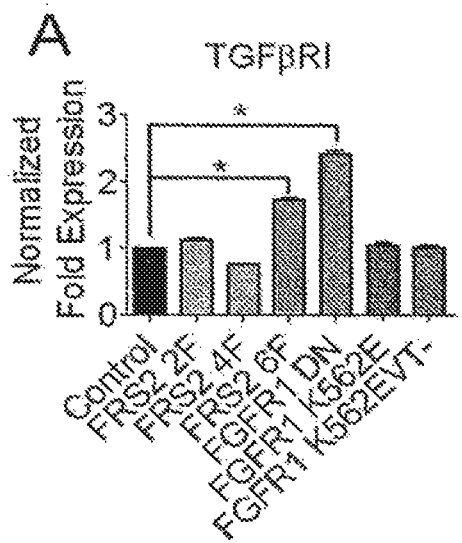
FIGS. 10A-10F are bar graphs showing qRT-PCR mRNA expression (relative mRNA level) of TGFβRI (FIG. 10A), TGFβRII (FIG. 10B), SM α-actin (FIG. 10C), SM22α (FIG. 10D), SM-calponin (FIG. 10E), and Fibronectin (FIG. 10F) in control (row 1) or FRF2 2F (row 2), FRS2 4F (row 3), FRS2 6F (row 3), FGFR1 dominant negative (row 4), FGFR1 K562E (row 5), or FGFR1 K562EVT (row 6) mutant overexpressing HUAEC.
Figure 10B:
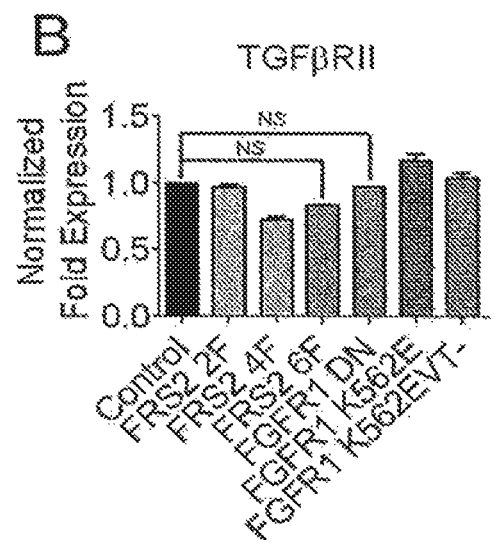
Figure 10C:
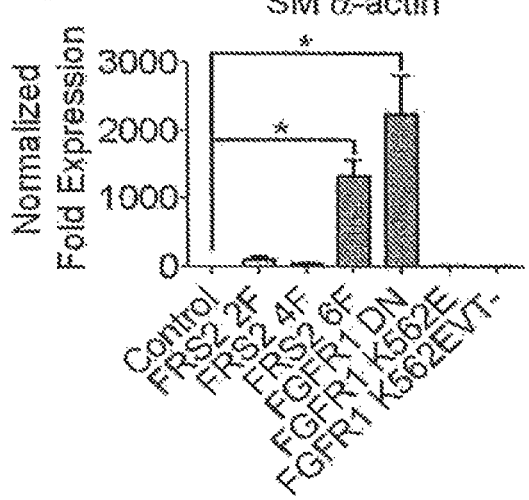
Figure 10D:
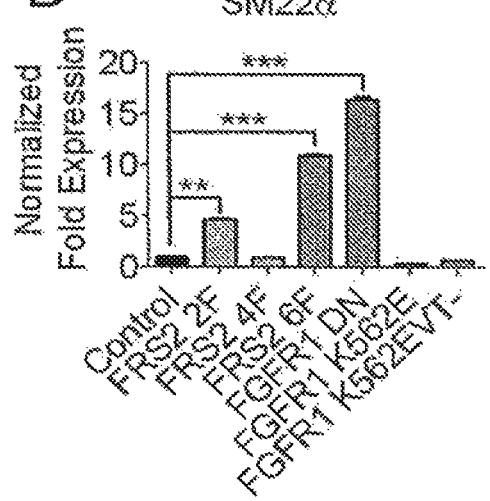
Figure 10E:
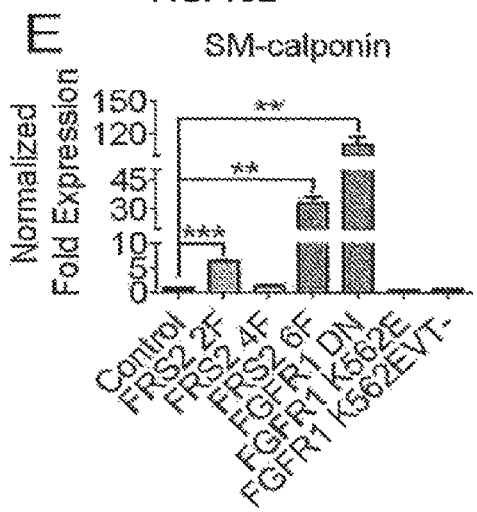
Figure 10F:
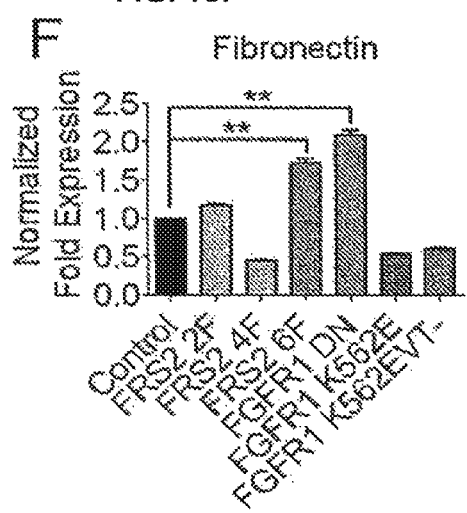
Figure 11A:
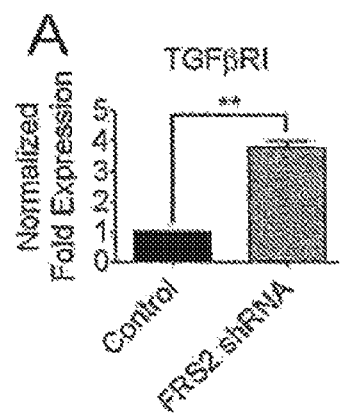
Figure 11B:
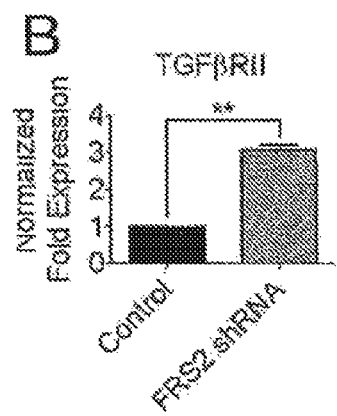
Figure 11C:
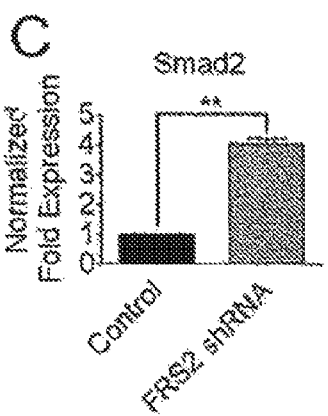
Figure 11D:
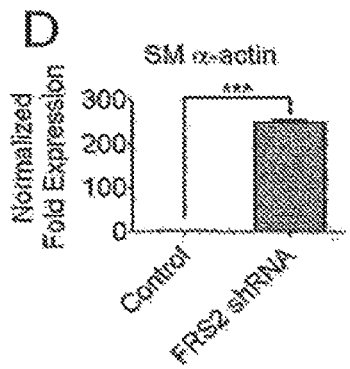
Figure 11E:
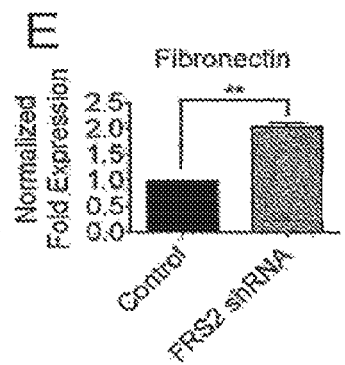
Figure 11F:
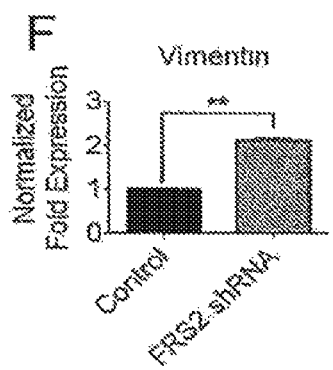
Figure 11L:
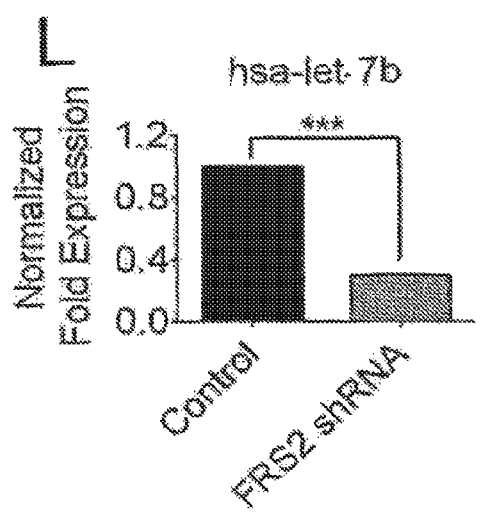
Figure 11M:
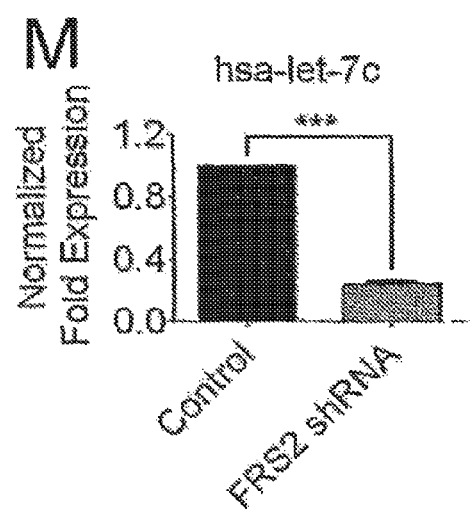
Figures 12A, 12B, 12C, 12D:
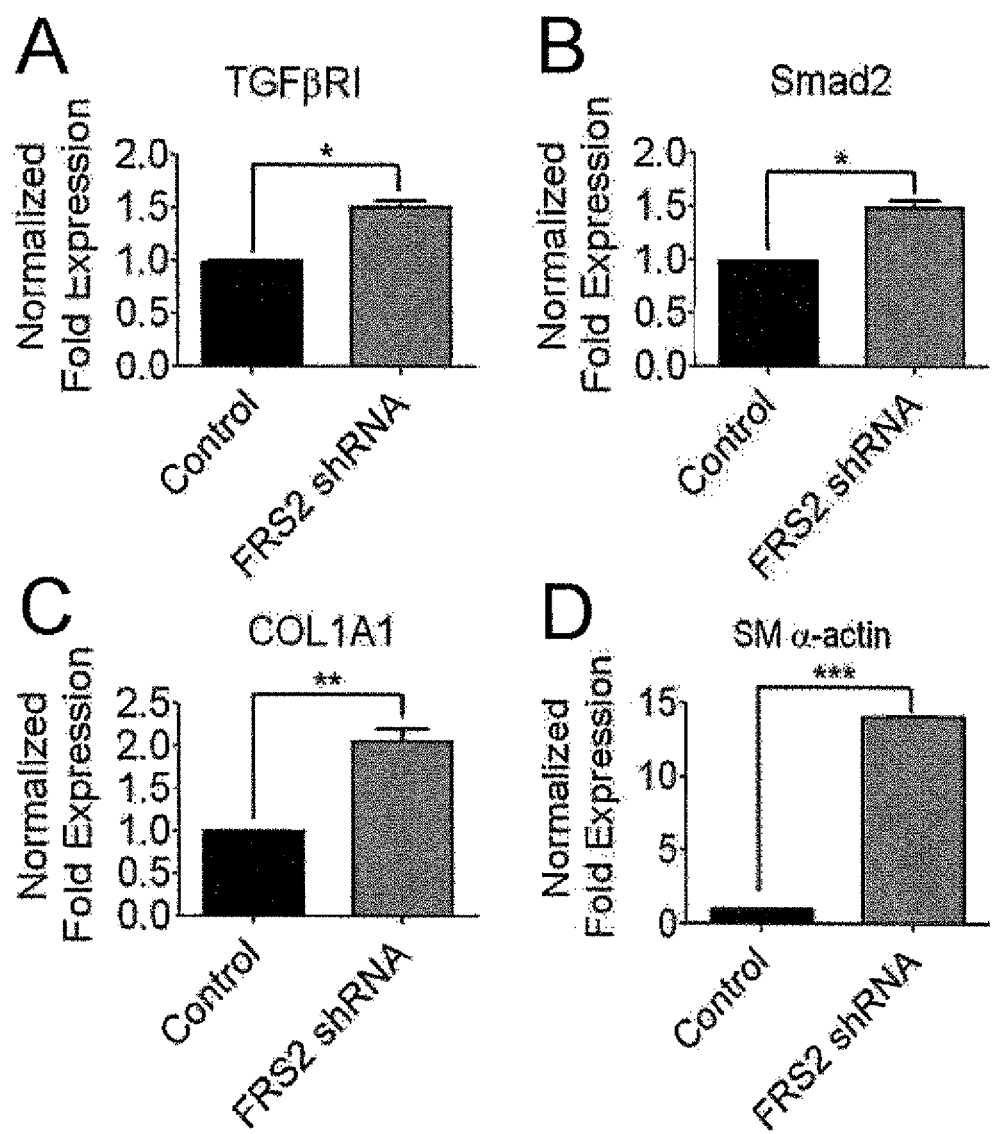
FIGS. 12A-12D are bar graphs showing qRT-PCR mRNA expression (relative mRNA level) of TGFβR1 (FIG. 12A), Smad2 (FIG. 12B), COL1A1 (FIG. 12C), and SM α-actin (FIG. 12D) in control (solid bars) and FRS2 knockdown (shaded bars) foreskin cells.
Figures 12E, 12F, 12G, 12H:
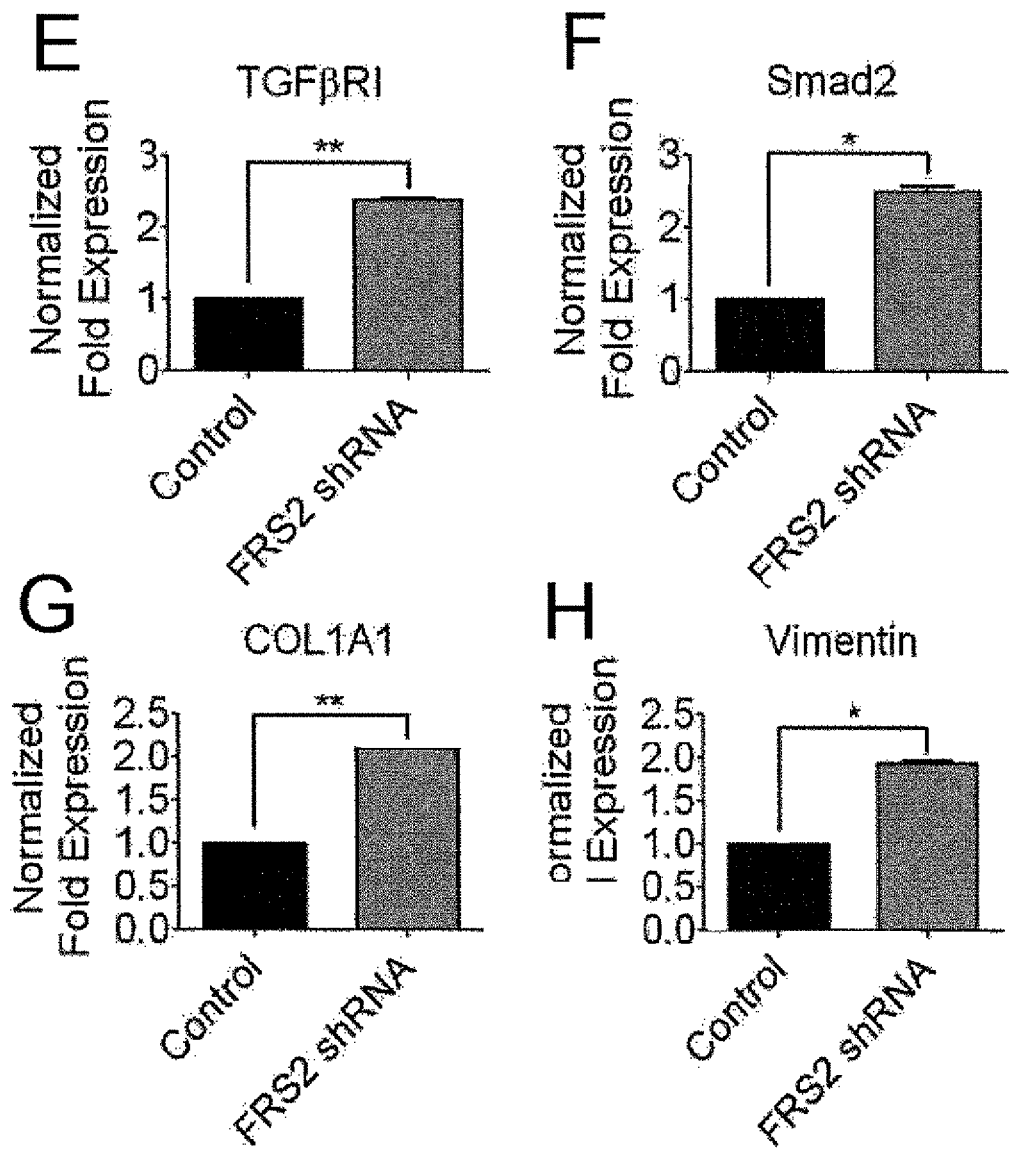
FIGS. 12E-12H are bar graphs showing qRT-PCR mRNA expression (relative mRNA level) of TGFβR1 (FIG. 12E), Smad2 (FIG. 12F), COL1A1 (FIG. 12G), and Vimentin (FIG. 12H) in control (solid bars) and FRS2 knockdown (shaded bars) atrial cells.
Figure 13:
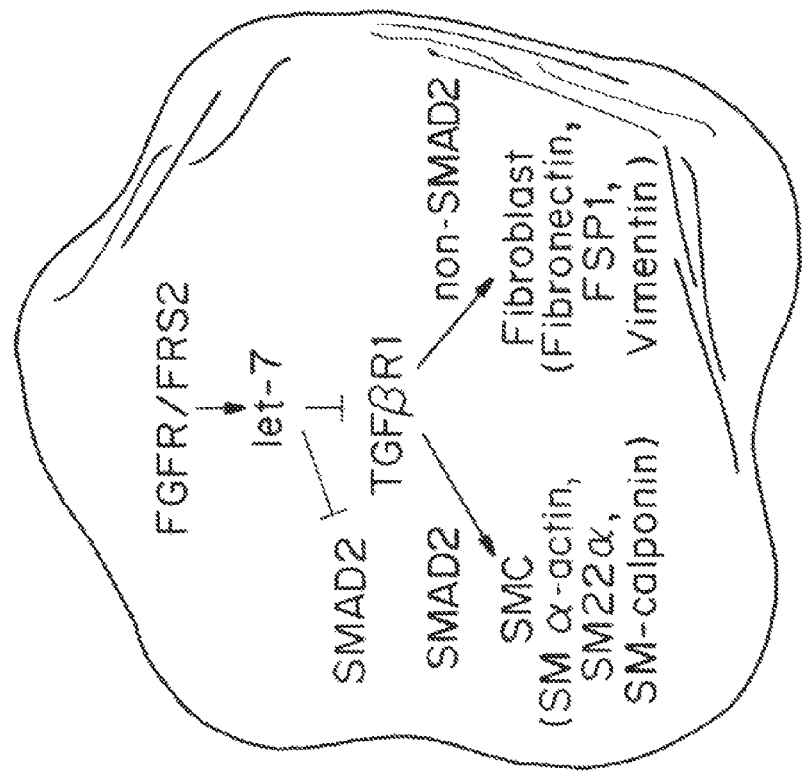
FIG. 13 is an illustration of the FGF/TGFβ signaling pathway involved in endothelial-to-mesenchymal (Endo-MT) transition. TGFβ activity through TGFβRI promotes Endo-MT via SMAD2-dependent (smooth muscle cells) and SMAD2-indendent (fibroblasts) pathways. TGFβR1 and SMAD2 are inhibited by let-7, which is activated by FGF signaling through FGFR. As let-7 decreases, TGFβ activity increases and Endo-MT.
Figure 13:
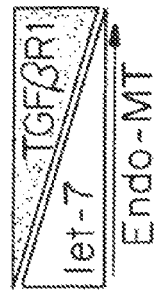
Figure 13:
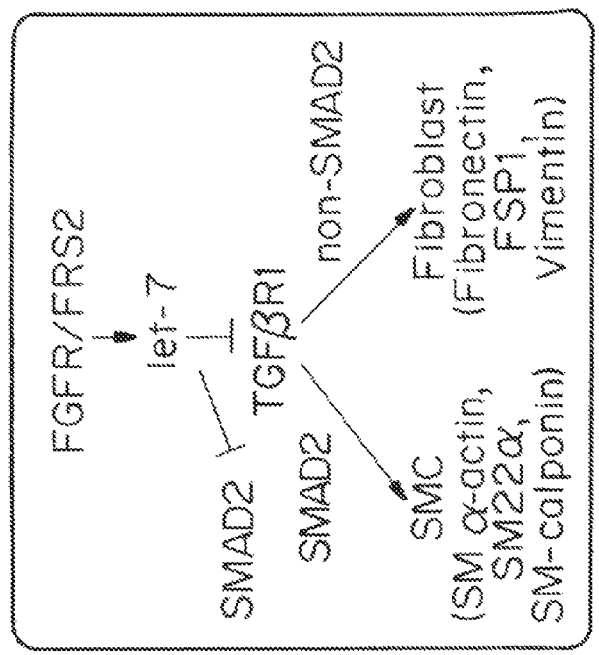

To determine if Endo-MT contributes to this process, lineage analysis of neointimal cells was performed following TEVG insertion into Rosa26 mice crossed with Tie2-Cre or Cdh5CreERT2 mice with the latter Cre activated by tamoxifen administration on day P2. In both cases LacZ-positive cells are found throughout the entire neointima. Confocal analysis of neointima samples double stained for LacZ and SM α-actin demonstrates co-localization of both markers in 40-50% of SMC (FIGS. 8A-8B).

Tie2-CreXRosa26 mice were treated with the TGFBR1 inhibitor SB-431542 at 10 mg/kg twice daily by intraperitoneal administration for 2 weeks following implantation of our TEVG (n=16). Matched control mice received intraperitoneal injection of sterile DMSO (n=25). Results of these studies showed that TGFBR1 inhibitor treatment significantly increases TEVG luminal diameter and graft patency at 2 weeks in unseeded grafts (p<0.001 for diameter, p<0.01 for stenosis) (FIGS. 8C and 8D). Drug treatment also allows for proper neotissue creation with an organized CD31 positive endothelial cell layer lining an SMA positive smooth muscle cell layer in contrast to the typical untreated control graft that occludes as a result of accumulation of SMA positive smooth muscle cells.

In order to unravel the mechanism by which SB-431542 treatment prevents TEVG stenosis, we treated mice from the Tie2 lineage-tracing model (n=10) with TGFBR1 inhibitor drug and then performed confocal analysis and cellular quantification of TEVG samples double stained for LacZ and SMA. Results of these studies showed that drug treatment improves patency by reducing the occurrence of EMT, as demonstrated by a significant reduction in LacZ-positive smooth muscle cells in occluded grafts in drug treated mice (p<0.05) (FIG. 8E).

Example 5

Local Delivery of TGFBR1 Inhibitor Inhibits Stenosis without Cell Seeding and Maintains Normal Neovessel Formation Materials and Methods Microparticle Synthesis and Characterization SB-431542 was encapsulated in avidin-coated PLGA microparticles using a modified oil/water single emulsion technique as previously described (Fahmy, T. M., et al. *Biomaterials* 26:5727-5736 (2005)). Control microparticles were synthesized without SB-431542. Microparticle size and morphology were analyzed via scanning electron microscopy (SEM) as previously described (Rob, J. D., et al. *Proc Natl Acad Sci USA* 107:4669-4674 (2010)).

Preparation of Adhesive Peptide Tether

Poly-L-lysine-LC-LC-biotin (pLLB) was synthesized and used as an adhesive peptide tether to enhance loading of PGA-P(CL/LA) scaffolds with avidin-coated microparticles. 1.66 mg EZ-Link sulfo NHS-LC-LC-biotin was reacted with 10 ml of a 0.1 mg/ml solution of poly-L-lysine (MW 70,000-150,000, Sigma) in PBS for 2 hours at 4 C, dialyzed in PBS for 72 hours, and stored at 4 C.

Loading of TEVG Scaffolds with SB-431542-Eluting Microparticles

Nonspecific adsorption of avidin-coated PLGA microparticles to PGA-P(CL/LA) scaffolds not treated with pLLB was titrated by incubating trimmed scaffolds with 1 ml of 1, 5, or 10 mg/ml of microparticles in PBS for 10, 30 or 60 minutes. Particle-loaded TEVG scaffolds were immediately snap frozen in liquid nitrogen and lyophilized for 6 hours before imaging. Scaffold loading efficiency was determined with ImageJ software from three SEM images per scaffold cross-section, inner surface, and outer surface by calculating the mean surface density of particles. The effect of scaffold pretreatment with pLLB on scaffold loading efficiency was assessed from particle loading density as above after PGA-P(CL/LA) scaffolds were incubated with 1 ml of 0.01, 0.1 or 1 mg/ml pLLB for 60 minutes on a rotary shaker, washed with dH2O, incubated with 1 ml 5 mg/ml avidin-coated PLGA microparticles, washed with dH$_2$O, snap frozen in liquid nitrogen, lyophilized for 6 hours, and imaged by SEM. For in vitro and in vivo studies, PGA-P(CL/LA) scaffolds were incubated with pLLB for 30 minutes at 20 C, washed with dH2O, incubated with 5 mg/ml empty or SB-431542-eluting avidin-coated PLGA microparticles for 30 minutes, washed with dH2O, snap frozen in liquid nitrogen, and lyophilized for 6 hours before desiccated storage.

Characterization of SB-431542 Release from Microparticles and Scaffolds

Total encapsulation was approximated as the amount of SB-431542 released over a 14-day period. Percent encapsulation efficiency was calculated as total encapsulation divided by maximum theoretical encapsulation. 5 mg of avidin-coated PLGA microparticles containing SB-431542, PGA-P(CL/LA) trimmed scaffolds and treated with pLLB and SB-431542-eluting microparticles as above, and SB-431542-eluting PGA-P(CL/LA) trimmed scaffolds were incubated with PBS in triplicate on a rotary shaker at 37° C. Samples were removed at specific time points and centrifuged at 13200 RPM for 10 minutes. 300 μl of supernatant was drawn and replaced with 300 μl PBS. Concentration of SB-431542 in supernatant diluted with 600 μl PBS was determined by spectrophotometry at 320 nm.

Bioactivity of Encapsulated SB-431542

SB-431542 was released into 1 ml PBS from 10 mg avidin-coated PLGA microparticles and one untrimmed SB-431542-eluting PGA-P(CL/LA) scaffold in 2 ml microcentrifuge tubes at 37° C. At 48 hours, samples were centrifuged at 13200 RPM for 10 minutes, supernatants were collected and analyzed by spectrophotometry at 320 nm. SB-431542 concentrations were adjusted to 10 μM by dilution with PBS. 3T3 human fibroblasts were plated at 500,000/well and stimulated at confluence with 700 ul 10 μM SB-431542 in PBS eluted from particles or scaffolds, a stock solution of 10 or 1 μM SB-431542 containing <1% DMSO, or PBS. After 30 minutes at 37° C., cells were washed and stimulated with 200 ul 2 ng/ml recombinant human TGF-β1 (BD Biosciences) for 1 hour at 37 C. Cells were lysed and protein samples were separated by gel electrophoresis with a 12% polyacrylamide gel and probed with primary antibody to phosphorylated SMAD-2 (ser426/ser428, Cell Signaling Technology) and secondary goat anti-rabbit IgG (Cell Signaling Technology). The gel was stripped and reprobed with anti-SMAD2/3 as a loading control.

Results

Figure 14A:
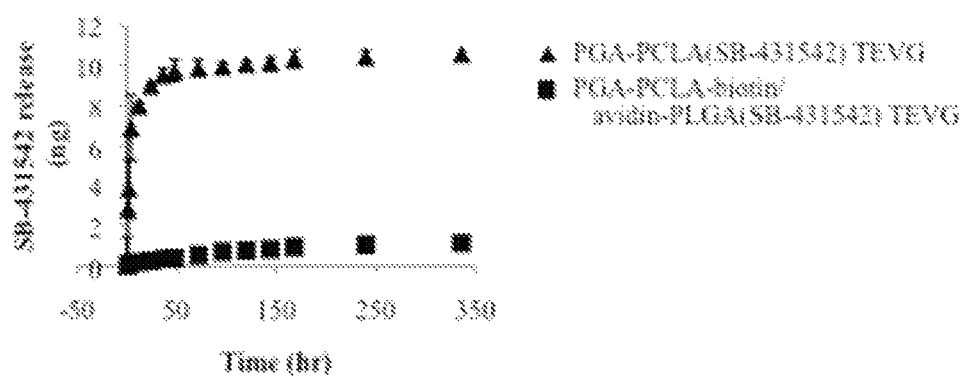
FIGS. 14A to 14B are graphs showing absolute (FIG. 14A) and fractional (FIG. 14B) release of SB-431542 from (■) tethered PLGA microparticles and (▲) PCLA phase of a PGA-PCLA TEVG scaffold.
Figure 14B:
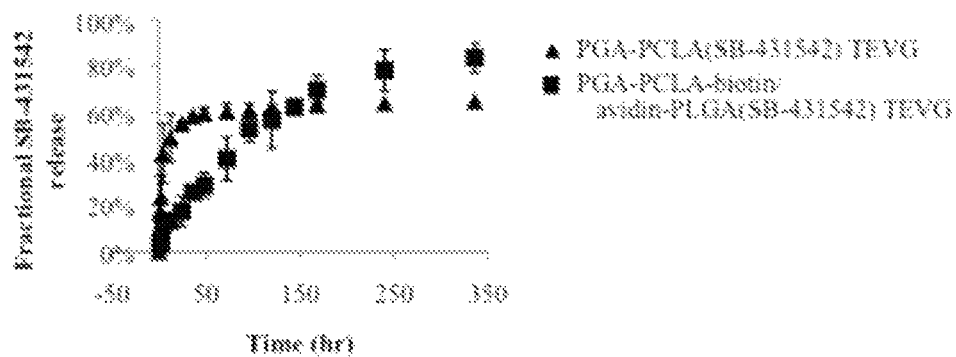
Figure 14C:
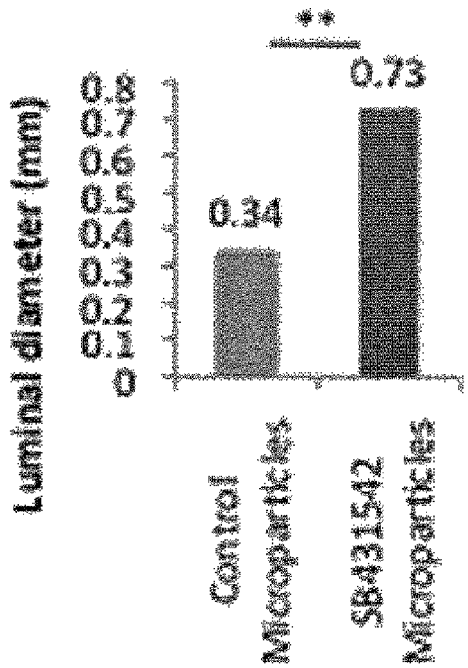
FIGS. 14C and 14D are bar graphs showing luminal diameter (mm) (FIG. 14C) and stenosis rate (%) of control microparticles (FIG. 14A, bar 1.
Figure 14D:
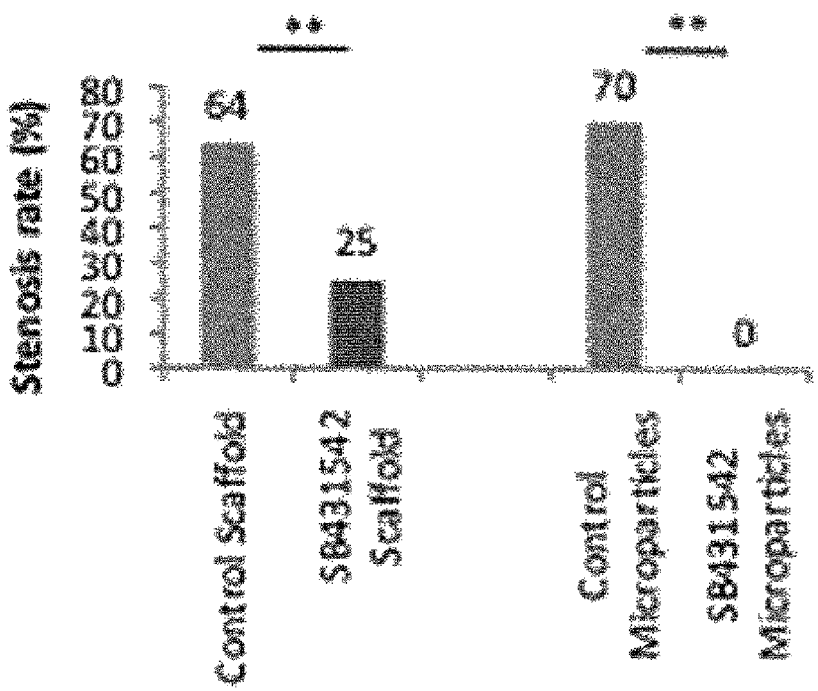

A microparticle system was developed for local delivery of the TGFBR1 inhibitor SB-431542 in order to minimize possible effects of systemic delivery. This system was characterized to show that there is steady release of the drug across the full 2-week time course during which the grafts are implanted (FIGS. 14A and 14B), and showed that the released drug maintains its biologic activity. A simpler local drug delivery system was also developed by which the TGFBR1 inhibitor was added to the solvent used to make the grafts. This system also demonstrated a favorable release profile and continued biologic activity of the released drug (FIGS. 14A and 14B). Both types of drug-eluting grafts were then implanted in the mouse model (n=10 for drug in microparticles, n=24 for drug in solvent) and their patency compared to grafts with empty microparticles (n=10) or control grafts (n=25). Results of these studies showed that local drug delivery significantly increases patency at 2 weeks in unseeded grafts (p<0.01) and also enabled neotissue creation (FIGS. 14C and 14D).

We claim:

1. A method for enhancing repair or regeneration of endothelial tissue while not promoting conversion of endothelial cells into smooth muscle cells in a subject in need thereof, comprising administering to the subject immediately before, at the time of or after implantation of a vascular scaffold, stent or graft, a pharmaceutical composition comprising an effective amount of a TGFβ inhibitor, a SMAD2 inhibitor, an FGF Receptor agonist, a Let-7 agonist, or a combination thereof to promote endothelial cell growth but not smooth muscle cell proliferation.

2. The method of claim 1, wherein the TGFβ inhibitor or SMAD2 inhibitor is selected from the group consisting of 4-[4-(1,3-Benzodioxol-5-yl)-5-(2-pyridinyl)-1H-imidazol-2-yl]-benzamide (SB431542), 2-(5-Chloro-2-fluorophenyl)-4-[(4-pyridyl)amino]pteridine (SB208), 6-[2-(1,1-Dimethylethyl)-5-(6-methyl-2-pyridinyl)-1H-imidazol-4-yl]quinoxaline (SB525334), 4-(5-(benzo[d][1,3]dioxol-5-yl)-4-(6-methylpyridin-2-yl)-1H-imidazol-2-yl)bicyclo[2.2.2]octane-1-carboxamide (SM16), 4-(2-(6-methylpyridin-2-yl)-5,6-dihydro-4H-pyrrolo[1,2-b]pyrazol-3-yl)quinoline-6-carboxamide (LY2157299), 3-((5-([1,2,4]triazolo[1,5-a]pyridin-6-yl)-4-(6-methylpyridin-2-yl)thiazol-2-ylamino)methyl)benzonitrile (EW-7203), and (2-butyl-4-chloro-1-{[2'-(1H-tetrazol-5-yl)biphenyl-4-yl]methyl}-1H-imidazol-5-yl)methanol (Losartan).

3. The method of claim 1, wherein the Let-7 agonist is a polynucleotide encoding a Let-7 pri-miRNA, pre-miRNA, mature miRNA, or RNAi effective in silencing TGFβRI gene expression.

4. The method of claim 3, wherein the Let-7 agonist comprises a nucleic acid sequence selected from the group consisting of SEQ ID NO:102, 103, 104, 105, 105, 106, 107, 108, 109, 110, 111, 112, or 113, or a fragment or variant thereof capable of binding a let-7 target sequence and silence TGFβRI gene expression.

5. The method of claim 1, wherein the FGF Receptor agonist is selected from the group consisting of an FGF protein, an FGFR agonistic antibody and a small molecule.

6. The method of claim 1, wherein the pharmaceutical composition is administered to the subject after implantation of a vascular scaffold, graft or stent.

7. The method of claim 1, wherein the pharmaceutical composition is coated on or incorporated into a vascular scaffold, graft or stent prior to implantation.

8. A method for increasing the patency of a polymeric vascular graft, scaffold or stent comprising administering to the graft, scaffold or stent an effective amount of a composition comprising a TGFβ inhibitor, a SMAD2 inhibitor, an FGF Receptor agonist, a Let-7 agonist, or a combination thereof to promote endothelial cell growth but not smooth muscle cell proliferation.

9. The method of claim 8, wherein the TGFβ inhibitor or SMAD2 inhibitor is selected from the group consisting of 4-[4-(1,3-Benzodioxol-5-yl)-5-(2-pyridinyl)-1H-imidazol-2-yl]-benzamide (SB431542), 2-(5-Chloro-2-fluorophenyl)-4-[(4-pyridyl)amino]pteridine (SB208), 6-[2-(1,1-Dimethylethyl)-5-(6-methyl-2-pyridinyl)-1H-imidazol-4-yl]quinoxaline (SB525334), 4-(5-(benzo[d][1,3]dioxol-5-yl)-4-(6-methylpyridin-2-yl)-1H-imidazol-2-yl)bicyclo[2.2.2]octane-1-carboxamide (SM16), 4-(2-(6-methylpyridin-2-yl)-5,6-dihydro-4H-pyrrolo[1,2-b]pyrazol-3-yl)quinoline-6-carboxamide (LY2157299), 3-((5-([1,2,4]triazolo[1,5-a]pyridin-6-yl)-4-(6-methylpyridin-2-yl)thiazol-2-ylamino)methyl)benzonitrile (EW-7203), and (2-butyl-4-chloro-1-{[2'-(1H-tetrazol-5-yl)biphenyl-4-yl]methyl}-1H-imidazol-5-yl)methanol (Losartan).

10. The method of claim 8, wherein the Let-7 agonist is a polynucleotide encoding a Let-7 pri-miRNA, pre-miRNA, mature miRNA, or RNAi effective in silencing TGFβRI gene expression.

11. The method of claim 10, wherein the Let-7 agonist comprises a nucleic acid sequence selected from the group consisting of SEQ ID NO:102, 103, 104, 105, 105, 106, 107, 108, 109, 110, 111, 112, or 113, or a fragment or variant thereof capable of binding a let-7 target sequence and silence TGFβRI gene expression.

12. The method of claim 8, wherein the FGF Receptor agonist is selected from the group consisting of an FGF protein, an FGFR agonistic antibody and a small molecule.

13. The method of claim 8, wherein the vascular graft, scaffold or stent comprises biodegradable or bioabsorbable polymers.

14. The method of claim 13, wherein the biodegradable or bioabsorbable polymers are selected from the group consisting of poly(lactic acid), poly(glycolic acid), polyanhydrides, poly(ortho)esters, polyesters, polyurethanes, poly(butic acid), poly(valeric acid), poly(caprolactone), poly(hydroxyalkanoates), and poly(lactide-co-caprolactone), or combinations, blends or co-polymers thereof.

15. The method of claim 13, wherein the biodegradable or bioabsorbable polymers are formed into a fiber-based mesh.

16. The method of claim 15, wherein the fiber-based mesh is a non-woven mesh.

17. The method of claim 13, wherein the vascular graft, scaffold or stent further comprises a polymeric sealant.

18. The method of claim 17, wherein the polymeric sealant comprises a co-polymer of ε-caprolactone and L-lactide.

19. The method of claim 8, wherein the pharmaceutical composition is coated on or incorporated into the vascular graft, scaffold or stent.

\* \* \* \* \*

UNITED STATES PATENT AND TRADEMARK OFFICE
CERTIFICATE OF CORRECTION

PATENT NO. : 9,446,175 B2
APPLICATION NO. : 14/123728
DATED : September 20, 2016
INVENTOR(S) : Christopher Breuer et al.

Page 1 of 1

It is certified that error appears in the above-identified patent and that said Letters Patent is hereby corrected as shown below:

In the Specification

Column 3, Line 19, replace "TGTGFβ inhibitor" with --TGF β inhibitor--.
Column 14, Line 26, replace "TGFTGFβ inhibitor" with --TGF β inhibitor--.
Column 16, Line 51, replace "TGFTGFβ inhibitor" with --TGF β inhibitor--.

In the Claims

Claim 4, Column 69, Lines 50-51, replace "105, 105, 106, 107, 108, 109, 110, 111, 112, or 113" with --105, 106, 107, 108, 109, 110, 111, 112, and 113--.
Claim 11, Column 70, Lines 42-43, replace "105, 105, 106, 107, 108, 109, 110, 111, 112, or 113" with --105, 106, 107, 108, 109, 110, 111, 112, and 113--.
Claim 14, Column 70, Lines 57-58, replace "or combinations" with --and combinations--.

Signed and Sealed this
Twentieth Day of June, 2017

Joseph Matal
*Performing the Functions and Duties of the*
*Under Secretary of Commerce for Intellectual Property and*
*Director of the United States Patent and Trademark Office*

SEQUENCE LISTING

<160> NUMBER OF SEQ ID NOS: 113

<210> SEQ ID NO 1
<211> LENGTH: 45
<212> TYPE: DNA
<213> ORGANISM: Artificial Sequence
<220> FEATURE:
<223> OTHER INFORMATION: Synthetic Construct

<400> SEQUENCE: 1
gctgaggaac aagtacatac ttttgttaac actacaggtg tgcaa                45

<210> SEQ ID NO 2
<211> LENGTH: 46
<212> TYPE: DNA
<213> ORGANISM: Artificial Sequence
<220> FEATURE:
<223> OTHER INFORMATION: Synthetic Construct

<400> SEQUENCE: 2
cttgcacacc tgtagtgtta acaaaagtat gtacttgttc ctcagc               46

<210> SEQ ID NO 3
<211> LENGTH: 50
<212> TYPE: DNA
<213> ORGANISM: Artificial Sequence
<220> FEATURE:
<223> OTHER INFORMATION: Synthetic Construct

<400> SEQUENCE: 3 gcccctgtc aacaaactgg tgtttgaaaa tataaacggg ctatctattc             50

<210> SEQ ID NO 4
<211> LENGTH: 50
<212> TYPE: DNA
<213> ORGANISM: Artificial Sequence
<220> FEATURE:
<223> OTHER INFORMATION: Synthetic Construct

<400> SEQUENCE: 4
gaatagatag cccgtttata ttttcaaaca ccagtttgtt gacaggggc             50

<210> SEQ ID NO 5
<211> LENGTH: 48
<212> TYPE: DNA
<213> ORGANISM: Artificial Sequence
<220> FEATURE:
<223> OTHER INFORMATION: Synthetic Construct

<400> SEQUENCE: 5
gagaagacct gcactattaa actttgaaaa tttaccatct ttgcctcc              48

<210> SEQ ID NO 6
<211> LENGTH: 48
<212> TYPE: DNA
<213> ORGANISM: Artificial Sequence
<220> FEATURE:
<223> OTHER INFORMATION: Synthetic Construct

<400> SEQUENCE: 6
ggaggcaaag atggtaaatt ttcaaagttt aatagtgcag gtcttctc              48

<210> SEQ ID NO 7
<211> LENGTH: 45
<212> TYPE: DNA
<213> ORGANISM: Artificial Sequence

```
<220> FEATURE:
<223> OTHER INFORMATION: Synthetic Construct

<400> SEQUENCE: 7
gatccaatgc ataactttgt taatacagag aatgtaacag tgccg          45

<210> SEQ ID NO 8
<211> LENGTH: 45
<212> TYPE: DNA
<213> ORGANISM: Artificial Sequence
<220> FEATURE:
<223> OTHER INFORMATION: Synthetic Construct

<400> SEQUENCE: 8
cggcactgtt acattctctg tattaacaaa gttatgcatt ggatc          45

<210> SEQ ID NO 9
<211> LENGTH: 46
<212> TYPE: DNA
<213> ORGANISM: Artificial Sequence
<220> FEATURE:
<223> OTHER INFORMATION: Synthetic Construct

<400> SEQUENCE: 9
gtttagaaca taggcaactc aattttatac aggtggattt ggaagg         46

<210> SEQ ID NO 10
<211> LENGTH: 46
<212> TYPE: DNA
<213> ORGANISM: Artificial Sequence
<220> FEATURE:
<223> OTHER INFORMATION: Synthetic Construct

<400> SEQUENCE: 10
ccttccaaat ccacctgtat aaaattgagt tgcctatgtt ctaaac         46

<210> SEQ ID NO 11
<211> LENGTH: 44
<212> TYPE: DNA
<213> ORGANISM: Artificial Sequence
<220> FEATURE:
<223> OTHER INFORMATION: Synthetic Construct

<400> SEQUENCE: 11
cacgcggcgc acagagctgt tcgctgtgat agacattgag agaa           44

<210> SEQ ID NO 12
<211> LENGTH: 44
<212> TYPE: DNA
<213> ORGANISM: Artificial Sequence
<220> FEATURE:
<223> OTHER INFORMATION: Synthetic Construct

<400> SEQUENCE: 12
ttctctcaat gtctatcaca gcgaacagct ctgtgcgccg cgtg            44

<210> SEQ ID NO 13
<211> LENGTH: 22
<212> TYPE: DNA
<213> ORGANISM: Artificial Sequence
<220> FEATURE:
<223> OTHER INFORMATION: Synthetic Construct

<400> SEQUENCE: 13
ggcatctgta agtggttcaa cg                                    22
```

```
<210> SEQ ID NO 14
<211> LENGTH: 19
<212> TYPE: DNA
<213> ORGANISM: Artificial Sequence
<220> FEATURE:
<223> OTHER INFORMATION: Synthetic Construct

<400> SEQUENCE: 14
ccctccttga ggcttcgga                                                  19

<210> SEQ ID NO 15
<211> LENGTH: 21
<212> TYPE: DNA
<213> ORGANISM: Artificial Sequence
<220> FEATURE:
<223> OTHER INFORMATION: Synthetic Construct

<400> SEQUENCE: 15
gatgggctct ctccagatca g                                               21

<210> SEQ ID NO 16
<211> LENGTH: 22
<212> TYPE: DNA
<213> ORGANISM: Artificial Sequence
<220> FEATURE:
<223> OTHER INFORMATION: Synthetic Construct

<400> SEQUENCE: 16
ggctgcatca ttcttgtcac tt                                              22

<210> SEQ ID NO 17
<211> LENGTH: 19
<212> TYPE: DNA
<213> ORGANISM: Artificial Sequence
<220> FEATURE:
<223> OTHER INFORMATION: Synthetic Construct

<400> SEQUENCE: 17
gggctgtgct gtctgttga                                                  19

<210> SEQ ID NO 18
<211> LENGTH: 21
<212> TYPE: DNA
<213> ORGANISM: Artificial Sequence
<220> FEATURE:
<223> OTHER INFORMATION: Synthetic Construct

<400> SEQUENCE: 18
tgattcccct caggtaaggc a                                               21

<210> SEQ ID NO 19
<211> LENGTH: 22
<212> TYPE: DNA
<213> ORGANISM: Artificial Sequence
<220> FEATURE:
<223> OTHER INFORMATION: Synthetic Construct

<400> SEQUENCE: 19
tccatgctag actcagaagt ca                                              22

<210> SEQ ID NO 20
<211> LENGTH: 21
<212> TYPE: DNA
<213> ORGANISM: Artificial Sequence
<220> FEATURE:
<223> OTHER INFORMATION: Synthetic Construct
```

```
<400> SEQUENCE: 20
tcccggtgga cacaattttt c                                         21

<210> SEQ ID NO 21
<211> LENGTH: 21
<212> TYPE: DNA
<213> ORGANISM: Artificial Sequence
<220> FEATURE:
<223> OTHER INFORMATION: Synthetic Construct

<400> SEQUENCE: 21
ttccaggagt gataccagct t                                         21

<210> SEQ ID NO 22
<211> LENGTH: 19
<212> TYPE: DNA
<213> ORGANISM: Artificial Sequence
<220> FEATURE:
<223> OTHER INFORMATION: Synthetic Construct

<400> SEQUENCE: 22 aggggggcgtg atgactagg                                           19

<210> SEQ ID NO 23
<211> LENGTH: 22
<212> TYPE: DNA
<213> ORGANISM: Artificial Sequence
<220> FEATURE:
<223> OTHER INFORMATION: Synthetic Construct

<400> SEQUENCE: 23
gcaggcaacg atgaaaacta ct                                        22

<210> SEQ ID NO 24
<211> LENGTH: 21
<212> TYPE: DNA
<213> ORGANISM: Artificial Sequence
<220> FEATURE:
<223> OTHER INFORMATION: Synthetic Construct

<400> SEQUENCE: 24
gcaacttgtg gcggatttgt a                                         21

<210> SEQ ID NO 25
<211> LENGTH: 21
<212> TYPE: DNA
<213> ORGANISM: Artificial Sequence
<220> FEATURE:
<223> OTHER INFORMATION: Synthetic Construct

<400> SEQUENCE: 25
gtcccagaca tcagggagta a                                         21

<210> SEQ ID NO 26
<211> LENGTH: 21
<212> TYPE: DNA
<213> ORGANISM: Artificial Sequence
<220> FEATURE:
<223> OTHER INFORMATION: Synthetic Construct

<400> SEQUENCE: 26
tcggatactt cagcgtcagg a                                         21

<210> SEQ ID NO 27
```

```
<211> LENGTH: 21
<212> TYPE: DNA
<213> ORGANISM: Artificial Sequence
<220> FEATURE:
<223> OTHER INFORMATION: Synthetic Construct

<400> SEQUENCE: 27
caacaagggt ccatcctacg g                                              21

<210> SEQ ID NO 28
<211> LENGTH: 19
<212> TYPE: DNA
<213> ORGANISM: Artificial Sequence
<220> FEATURE:
<223> OTHER INFORMATION: Synthetic Construct

<400> SEQUENCE: 28
atctgggcgg cctacatca                                                 19

<210> SEQ ID NO 29
<211> LENGTH: 22
<212> TYPE: DNA
<213> ORGANISM: Artificial Sequence
<220> FEATURE:
<223> OTHER INFORMATION: Synthetic Construct

<400> SEQUENCE: 29
aaacaagagc ggagatttga gc                                             22

<210> SEQ ID NO 30
<211> LENGTH: 19
<212> TYPE: DNA
<213> ORGANISM: Artificial Sequence
<220> FEATURE:
<223> OTHER INFORMATION: Synthetic Construct

<400> SEQUENCE: 30
tgtcgcagtg ttccatgcc                                                 19

<210> SEQ ID NO 31
<211> LENGTH: 19
<212> TYPE: DNA
<213> ORGANISM: Artificial Sequence
<220> FEATURE:
<223> OTHER INFORMATION: Synthetic Construct

<400> SEQUENCE: 31
aagctgcggc tagaggtca                                                 19

<210> SEQ ID NO 32
<211> LENGTH: 20
<212> TYPE: DNA
<213> ORGANISM: Artificial Sequence
<220> FEATURE:
<223> OTHER INFORMATION: Synthetic Construct

<400> SEQUENCE: 32
ccctcccttt gatggctgag                                                20

<210> SEQ ID NO 33
<211> LENGTH: 23
<212> TYPE: DNA
<213> ORGANISM: Artificial Sequence
<220> FEATURE:
<223> OTHER INFORMATION: Synthetic Construct

<400> SEQUENCE: 33
```

```
tcccaactac aggaccttttt tca                                           23

<210> SEQ ID NO 34
<211> LENGTH: 22
<212> TYPE: DNA
<213> ORGANISM: Artificial Sequence
<220> FEATURE:
<223> OTHER INFORMATION: Synthetic Construct

<400> SEQUENCE: 34
gcagtggtaa acctgatcca ga                                             22

<210> SEQ ID NO 35
<211> LENGTH: 19
<212> TYPE: DNA
<213> ORGANISM: Artificial Sequence
<220> FEATURE:
<223> OTHER INFORMATION: Synthetic Construct

<400> SEQUENCE: 35
cggctgcgag agaaattgc                                                 19

<210> SEQ ID NO 36
<211> LENGTH: 22
<212> TYPE: DNA
<213> ORGANISM: Artificial Sequence
<220> FEATURE:
<223> OTHER INFORMATION: Synthetic Construct

<400> SEQUENCE: 36
ccactttccg ttcaaggtca ag                                             22

<210> SEQ ID NO 37
<211> LENGTH: 17
<212> TYPE: DNA
<213> ORGANISM: Artificial Sequence
<220> FEATURE:
<223> OTHER INFORMATION: Synthetic Construct

<400> SEQUENCE: 37
gttgtcgacg acgagcg                                                   17

<210> SEQ ID NO 38
<211> LENGTH: 17
<212> TYPE: DNA
<213> ORGANISM: Artificial Sequence
<220> FEATURE:
<223> OTHER INFORMATION: Synthetic Construct

<400> SEQUENCE: 38
gcacagagcc tcgcctt                                                   17

<210> SEQ ID NO 39
<211> LENGTH: 22
<212> TYPE: DNA
<213> ORGANISM: Artificial Sequence
<220> FEATURE:
<223> OTHER INFORMATION: Synthetic Construct

<400> SEQUENCE: 39
aacagtgttg acatgaagag cc                                             22

<210> SEQ ID NO 40
<211> LENGTH: 22
<212> TYPE: DNA
```

```
<213> ORGANISM: Artificial Sequence
<220> FEATURE:
<223> OTHER INFORMATION: Synthetic Construct

<400> SEQUENCE: 40
tgtaaaacag cacgtcatcc tt                                              22

<210> SEQ ID NO 41
<211> LENGTH: 20
<212> TYPE: DNA
<213> ORGANISM: Artificial Sequence
<220> FEATURE:
<223> OTHER INFORMATION: Synthetic Construct

<400> SEQUENCE: 41
ttctgttcgc aggtgattgg                                                 20

<210> SEQ ID NO 42
<211> LENGTH: 20
<212> TYPE: DNA
<213> ORGANISM: Artificial Sequence
<220> FEATURE:
<223> OTHER INFORMATION: Synthetic Construct

<400> SEQUENCE: 42
catgttcagc tttgtggacc                                                 20

<210> SEQ ID NO 43
<211> LENGTH: 20
<212> TYPE: DNA
<213> ORGANISM: Artificial Sequence
<220> FEATURE:
<223> OTHER INFORMATION: Synthetic Construct

<400> SEQUENCE: 43
aacttgtcac cctctttgcc                                                 20

<210> SEQ ID NO 44
<211> LENGTH: 20
<212> TYPE: DNA
<213> ORGANISM: Artificial Sequence
<220> FEATURE:
<223> OTHER INFORMATION: Synthetic Construct

<400> SEQUENCE: 44
tcctcagcgc ttcttctttc                                                 20

<210> SEQ ID NO 45
<211> LENGTH: 20
<212> TYPE: DNA
<213> ORGANISM: Artificial Sequence
<220> FEATURE:
<223> OTHER INFORMATION: Synthetic Construct

<400> SEQUENCE: 45
aaaccaattc ttggagcagg                                                 20

<210> SEQ ID NO 46
<211> LENGTH: 20
<212> TYPE: DNA
<213> ORGANISM: Artificial Sequence
<220> FEATURE:
<223> OTHER INFORMATION: Synthetic Construct

<400> SEQUENCE: 46
ccataaaggg caaccaagag                                                 20
```

<210> SEQ ID NO 47
<211> LENGTH: 20
<212> TYPE: DNA
<213> ORGANISM: Artificial Sequence
<220> FEATURE:
<223> OTHER INFORMATION: Synthetic Construct

<400> SEQUENCE: 47
gatccaactg ctgctgaggt                                              20

<210> SEQ ID NO 48
<211> LENGTH: 20
<212> TYPE: DNA
<213> ORGANISM: Artificial Sequence
<220> FEATURE:
<223> OTHER INFORMATION: Synthetic Construct

<400> SEQUENCE: 48
aggcagacct aggaaatggc                                              20

<210> SEQ ID NO 49
<211> LENGTH: 20
<212> TYPE: DNA
<213> ORGANISM: Artificial Sequence
<220> FEATURE:
<223> OTHER INFORMATION: Synthetic Construct

<400> SEQUENCE: 49
cgggcatctg taagtggttc                                              20

<210> SEQ ID NO 50
<211> LENGTH: 20
<212> TYPE: DNA
<213> ORGANISM: Artificial Sequence
<220> FEATURE:
<223> OTHER INFORMATION: Synthetic Construct

<400> SEQUENCE: 50
cagacccttg gctgacttct                                              20

<210> SEQ ID NO 51
<211> LENGTH: 21
<212> TYPE: DNA
<213> ORGANISM: Artificial Sequence
<220> FEATURE:
<223> OTHER INFORMATION: Synthetic Construct

<400> SEQUENCE: 51
gaggagtcag tgaaggagtc a                                            21

<210> SEQ ID NO 52
<211> LENGTH: 21
<212> TYPE: DNA
<213> ORGANISM: Artificial Sequence
<220> FEATURE:
<223> OTHER INFORMATION: Synthetic Construct

<400> SEQUENCE: 52
ggcaagttga ttggagggat g                                            21

<210> SEQ ID NO 53
<211> LENGTH: 21
<212> TYPE: DNA
<213> ORGANISM: Artificial Sequence
<220> FEATURE:

<223> OTHER INFORMATION: Synthetic Construct

<400> SEQUENCE: 53
gccatcacca ctcaaaactg t                                          21

<210> SEQ ID NO 54
<211> LENGTH: 23
<212> TYPE: DNA
<213> ORGANISM: Artificial Sequence
<220> FEATURE:
<223> OTHER INFORMATION: Synthetic Construct

<400> SEQUENCE: 54
gcctgttgta tcccactgat cta                                        23

<210> SEQ ID NO 55
<211> LENGTH: 19
<212> TYPE: DNA
<213> ORGANISM: Artificial Sequence
<220> FEATURE:
<223> OTHER INFORMATION: Synthetic Construct

<400> SEQUENCE: 55
caaagccggc cttacagag                                             19

<210> SEQ ID NO 56
<211> LENGTH: 17
<212> TYPE: DNA
<213> ORGANISM: Artificial Sequence
<220> FEATURE:
<223> OTHER INFORMATION: Synthetic Construct

<400> SEQUENCE: 56
agcccagcca agcactg                                               17

<210> SEQ ID NO 57
<211> LENGTH: 20
<212> TYPE: DNA
<213> ORGANISM: Artificial Sequence
<220> FEATURE:
<223> OTHER INFORMATION: Synthetic Construct

<400> SEQUENCE: 57
gattttggac tgcacttcgc                                            20

<210> SEQ ID NO 58
<211> LENGTH: 20
<212> TYPE: DNA
<213> ORGANISM: Artificial Sequence
<220> FEATURE:
<223> OTHER INFORMATION: Synthetic Construct

<400> SEQUENCE: 58
gtccgaaccc agacacaagt                                            20

<210> SEQ ID NO 59
<211> LENGTH: 20
<212> TYPE: DNA
<213> ORGANISM: Artificial Sequence
<220> FEATURE:
<223> OTHER INFORMATION: Synthetic Construct

<400> SEQUENCE: 59
ctggctgcag cttattgatg                                            20

```
<210> SEQ ID NO 60
<211> LENGTH: 20
<212> TYPE: DNA
<213> ORGANISM: Artificial Sequence
<220> FEATURE:
<223> OTHER INFORMATION: Synthetic Construct

<400> SEQUENCE: 60
ctgagagagt ggatcgaggg                                                 20

<210> SEQ ID NO 61
<211> LENGTH: 21
<212> TYPE: DNA
<213> ORGANISM: Artificial Sequence
<220> FEATURE:
<223> OTHER INFORMATION: Synthetic Construct

<400> SEQUENCE: 61
caagcagagt acacacagca t                                               21

<210> SEQ ID NO 62
<211> LENGTH: 22
<212> TYPE: DNA
<213> ORGANISM: Artificial Sequence
<220> FEATURE:
<223> OTHER INFORMATION: Synthetic Construct

<400> SEQUENCE: 62
tgctccactt ttaacttgag cc                                              22

<210> SEQ ID NO 63
<211> LENGTH: 20
<212> TYPE: DNA
<213> ORGANISM: Artificial Sequence
<220> FEATURE:
<223> OTHER INFORMATION: Synthetic Construct

<400> SEQUENCE: 63
acggcgttac agtgtttctg                                                 20

<210> SEQ ID NO 64
<211> LENGTH: 21
<212> TYPE: DNA
<213> ORGANISM: Artificial Sequence
<220> FEATURE:
<223> OTHER INFORMATION: Synthetic Construct

<400> SEQUENCE: 64
gcacatacaa acggcctatc t                                               21

<210> SEQ ID NO 65
<211> LENGTH: 20
<212> TYPE: DNA
<213> ORGANISM: Artificial Sequence
<220> FEATURE:
<223> OTHER INFORMATION: Synthetic Construct

<400> SEQUENCE: 65
tctggttgtc acaggtggaa                                                 20

<210> SEQ ID NO 66
<211> LENGTH: 20
<212> TYPE: DNA
<213> ORGANISM: Artificial Sequence
<220> FEATURE:
<223> OTHER INFORMATION: Synthetic Construct
```

```
<400> SEQUENCE: 66
gcacgttcag aagtcggtta                                               20

<210> SEQ ID NO 67
<211> LENGTH: 20
<212> TYPE: DNA
<213> ORGANISM: Artificial Sequence
<220> FEATURE:
<223> OTHER INFORMATION: Synthetic Construct

<400> SEQUENCE: 67
catgagcctc tgcatcttcc                                               20

<210> SEQ ID NO 68
<211> LENGTH: 20
<212> TYPE: DNA
<213> ORGANISM: Artificial Sequence
<220> FEATURE:
<223> OTHER INFORMATION: Synthetic Construct

<400> SEQUENCE: 68
acagagctcc actcacgctc                                               20

<210> SEQ ID NO 69
<211> LENGTH: 20
<212> TYPE: DNA
<213> ORGANISM: Artificial Sequence
<220> FEATURE:
<223> OTHER INFORMATION: Synthetic Construct

<400> SEQUENCE: 69
cggctctttc gcttactgtt                                               20

<210> SEQ ID NO 70
<211> LENGTH: 21
<212> TYPE: DNA
<213> ORGANISM: Artificial Sequence
<220> FEATURE:
<223> OTHER INFORMATION: Synthetic Construct

<400> SEQUENCE: 70
tctctctgcc tacctcacct g                                             21

<210> SEQ ID NO 71
<211> LENGTH: 20
<212> TYPE: DNA
<213> ORGANISM: Artificial Sequence
<220> FEATURE:
<223> OTHER INFORMATION: Synthetic Construct

<400> SEQUENCE: 71
gcaaagattc cactttgcgt                                               20

<210> SEQ ID NO 72
<211> LENGTH: 20
<212> TYPE: DNA
<213> ORGANISM: Artificial Sequence
<220> FEATURE:
<223> OTHER INFORMATION: Synthetic Construct

<400> SEQUENCE: 72
gaaattgcag gaggagatgc                                               20

<210> SEQ ID NO 73
<211> LENGTH: 22
```

```
<212> TYPE: DNA
<213> ORGANISM: Artificial Sequence
<220> FEATURE:
<223> OTHER INFORMATION: Synthetic Construct

<400> SEQUENCE: 73
cagtcagctg catctgtaac ac                                               22

<210> SEQ ID NO 74
<211> LENGTH: 20
<212> TYPE: DNA
<213> ORGANISM: Artificial Sequence
<220> FEATURE:
<223> OTHER INFORMATION: Synthetic Construct

<400> SEQUENCE: 74
ccaggtgtaa gcgcagaaag                                                  20

<210> SEQ ID NO 75
<211> LENGTH: 19
<212> TYPE: DNA
<213> ORGANISM: Artificial Sequence
<220> FEATURE:
<223> OTHER INFORMATION: Synthetic Construct

<400> SEQUENCE: 75
caagaggcgc aaacaagcc                                                   19

<210> SEQ ID NO 76
<211> LENGTH: 20
<212> TYPE: DNA
<213> ORGANISM: Artificial Sequence
<220> FEATURE:
<223> OTHER INFORMATION: Synthetic Construct

<400> SEQUENCE: 76
ggttggcaat accgtcatcc                                                  20

<210> SEQ ID NO 77
<211> LENGTH: 24
<212> TYPE: DNA
<213> ORGANISM: Artificial Sequence
<220> FEATURE:
<223> OTHER INFORMATION: Synthetic Construct

<400> SEQUENCE: 77
atcaagatca ttgctcctcc tgag                                             24

<210> SEQ ID NO 78
<211> LENGTH: 21
<212> TYPE: DNA
<213> ORGANISM: Artificial Sequence
<220> FEATURE:
<223> OTHER INFORMATION: Synthetic Construct

<400> SEQUENCE: 78
ctgcttgctg atccacatct g                                                21

<210> SEQ ID NO 79
<211> LENGTH: 26
<212> TYPE: DNA
<213> ORGANISM: Artificial Sequence
<220> FEATURE:
<223> OTHER INFORMATION: Synthetic Construct

<400> SEQUENCE: 79
```
agaatggtgg cacaaaccaa taatcc 26

<210> SEQ ID NO 80
<211> LENGTH: 24
<212> TYPE: DNA
<213> ORGANISM: Artificial Sequence
<220> FEATURE:
<223> OTHER INFORMATION: Synthetic Construct

<400> SEQUENCE: 80
caattcttaa cacccacaag gccg 24

<210> SEQ ID NO 81
<211> LENGTH: 24
<212> TYPE: DNA
<213> ORGANISM: Artificial Sequence
<220> FEATURE:
<223> OTHER INFORMATION: Synthetic Construct

<400> SEQUENCE: 81
gagtgtgctg tgattggaag gcag 24

<210> SEQ ID NO 82
<211> LENGTH: 23
<212> TYPE: DNA
<213> ORGANISM: Artificial Sequence
<220> FEATURE:
<223> OTHER INFORMATION: Synthetic Construct

<400> SEQUENCE: 82
gcacgagtgt ctgcagacac atg 23

<210> SEQ ID NO 83
<211> LENGTH: 21
<212> TYPE: DNA
<213> ORGANISM: Artificial Sequence
<220> FEATURE:
<223> OTHER INFORMATION: Synthetic Construct

<400> SEQUENCE: 83
gcgaagagtt tgtcctcaac c 21

<210> SEQ ID NO 84
<211> LENGTH: 21
<212> TYPE: DNA
<213> ORGANISM: Artificial Sequence
<220> FEATURE:
<223> OTHER INFORMATION: Synthetic Construct

<400> SEQUENCE: 84
aaagtcgctc tgagttgtta t 21

<210> SEQ ID NO 85
<211> LENGTH: 21
<212> TYPE: DNA
<213> ORGANISM: Artificial Sequence
<220> FEATURE:
<223> OTHER INFORMATION: Synthetic Construct

<400> SEQUENCE: 85
ggagcgggag aaatggatat g 21

<210> SEQ ID NO 86
<211> LENGTH: 23
<212> TYPE: DNA
<213> ORGANISM: Artificial Sequence
<220> FEATURE:
<223> OTHER INFORMATION: Synthetic Construct

<400> SEQUENCE: 86
gcggtctggc agtaaaaact atc                                              23

<210> SEQ ID NO 87
<211> LENGTH: 23
<212> TYPE: DNA
<213> ORGANISM: Artificial Sequence
<220> FEATURE:
<223> OTHER INFORMATION: Synthetic Construct

<400> SEQUENCE: 87
gtgaaacagc attgctgtca ctt                                              23

<210> SEQ ID NO 88
<211> LENGTH: 24
<212> TYPE: DNA
<213> ORGANISM: Artificial Sequence
<220> FEATURE:
<223> OTHER INFORMATION: Synthetic Construct

<400> SEQUENCE: 88
ctaggccaca gaattgaaag atct                                             24

<210> SEQ ID NO 89
<211> LENGTH: 25
<212> TYPE: DNA
<213> ORGANISM: Artificial Sequence
<220> FEATURE:
<223> OTHER INFORMATION: Synthetic Construct

<400> SEQUENCE: 89
gtaggtggaa attctagcat catcc                                            25

<210> SEQ ID NO 90
<211> LENGTH: 22
<212> TYPE: RNA
<213> ORGANISM: Artificial Sequence
<220> FEATURE:
<223> OTHER INFORMATION: Synthetic Construct

<400> SEQUENCE: 90
ugagguagua gguuguauag uu                                               22

<210> SEQ ID NO 91
<211> LENGTH: 22
<212> TYPE: RNA
<213> ORGANISM: Artificial Sequence
<220> FEATURE:
<223> OTHER INFORMATION: Synthetic Construct

<400> SEQUENCE: 91
ugagguagua gguugugugg uu                                               22

<210> SEQ ID NO 92
<211> LENGTH: 22
<212> TYPE: RNA
<213> ORGANISM: Artificial Sequence
<220> FEATURE:
<223> OTHER INFORMATION: Synthetic Construct

<400> SEQUENCE: 92
ugagguagua gguuguaugg uu                                               22

```
<210> SEQ ID NO 93
<211> LENGTH: 21
<212> TYPE: RNA
<213> ORGANISM: Artificial Sequence
<220> FEATURE:
<223> OTHER INFORMATION: Synthetic Construct

<400> SEQUENCE: 93
ugagguagua gguugcauag u                                              21

<210> SEQ ID NO 94
<211> LENGTH: 21
<212> TYPE: RNA
<213> ORGANISM: Artificial Sequence
<220> FEATURE:
<223> OTHER INFORMATION: Synthetic Construct

<400> SEQUENCE: 94
ugagguagga gguuguauag u                                              21

<210> SEQ ID NO 95
<211> LENGTH: 22
<212> TYPE: RNA
<213> ORGANISM: Artificial Sequence
<220> FEATURE:
<223> OTHER INFORMATION: Synthetic Construct

<400> SEQUENCE: 95
ugagguagua gauuguauag uu                                             22

<210> SEQ ID NO 96
<211> LENGTH: 21
<212> TYPE: RNA
<213> ORGANISM: Artificial Sequence
<220> FEATURE:
<223> OTHER INFORMATION: Synthetic Construct

<400> SEQUENCE: 96
ugagguagua guuguacag u                                               21

<210> SEQ ID NO 97
<211> LENGTH: 21
<212> TYPE: RNA
<213> ORGANISM: Artificial Sequence
<220> FEATURE:
<223> OTHER INFORMATION: Synthetic Construct

<400> SEQUENCE: 97
ugagguagua guugugcug u                                               21

<210> SEQ ID NO 98
<211> LENGTH: 22
<212> TYPE: RNA
<213> ORGANISM: Artificial Sequence
<220> FEATURE:
<223> OTHER INFORMATION: Synthetic Construct

<400> SEQUENCE: 98
ugagguagua aguuguauug uu                                             22

<210> SEQ ID NO 99
<211> LENGTH: 23
<212> TYPE: RNA
<213> ORGANISM: Artificial Sequence
<220> FEATURE:
<223> OTHER INFORMATION: Synthetic Construct
```

```
<400> SEQUENCE: 99
gggaggucaa uuguucuacc uca                                              23

<210> SEQ ID NO 100
<211> LENGTH: 24
<212> TYPE: RNA
<213> ORGANISM: Artificial Sequence
<220> FEATURE:
<223> OTHER INFORMATION: Synthetic Construct

<400> SEQUENCE: 100
agaccaaggu acauuuuacc ucau                                             24

<210> SEQ ID NO 101
<211> LENGTH: 23
<212> TYPE: RNA
<213> ORGANISM: Artificial Sequence
<220> FEATURE:
<223> OTHER INFORMATION: Synthetic Construct

<400> SEQUENCE: 101
acccaguugg uuucucuacc ucu                                              23

<210> SEQ ID NO 102
<211> LENGTH: 80
<212> TYPE: RNA
<213> ORGANISM: Homo sapiens

<400> SEQUENCE: 102
ugggaugagg uaguagguug uauaguuuua gggucacacc caccacuggg agauaacuau      60
acaaucuacu gucuuuccua                                                  80

<210> SEQ ID NO 103
<211> LENGTH: 72
<212> TYPE: RNA
<213> ORGANISM: Homo sapiens

<400> SEQUENCE: 103
agguugaggu aguagguugu auaguuuaga auuacaucaa gggagauaac uguacagccu      60
ccuagcuuuc cu                                                          72

<210> SEQ ID NO 104
<211> LENGTH: 74
<212> TYPE: RNA
<213> ORGANISM: Homo sapiens

<400> SEQUENCE: 104
gggugaggua guagguugua uaguuugggg cucugcccug cuaugggaua acauacaau       60 cuacugucuu uccu                                                        74

<210> SEQ ID NO 105
<211> LENGTH: 83
<212> TYPE: RNA
<213> ORGANISM: Homo sapiens

<400> SEQUENCE: 105
cggggugagg uaguagguug uggguuuca gggcagugau guugcccuc ggaagauaac        60 uauacaaccu acugccuucc cug                                              83

<210> SEQ ID NO 106
```

```
<211> LENGTH: 84
<212> TYPE: RNA
<213> ORGANISM: Homo sapiens

<400> SEQUENCE: 106
gcauccgggu ugagguagua gguuguaugg uuuagaguua cacccuggga guuaacugua    60
caaccuucua gcuuuccuug gagc                                          84

<210> SEQ ID NO 107
<211> LENGTH: 87
<212> TYPE: RNA
<213> ORGANISM: Homo sapiens

<400> SEQUENCE: 107
ccuaggaaga gguaguaggu ugcauaguuu uagggcaggg auuuugccca caaggaggua    60
acuauacgac cugcugccuu ucuuagg                                       87

<210> SEQ ID NO 108
<211> LENGTH: 79
<212> TYPE: RNA
<213> ORGANISM: Homo sapiens

<400> SEQUENCE: 108
cccgggcuga gguaggaggu uguauaguug aggaggacac ccaaggagau cacuauacgg    60
ccuccuagcu uuccccagg                                                79

<210> SEQ ID NO 109
<211> LENGTH: 87
<212> TYPE: RNA
<213> ORGANISM: Homo sapiens

<400> SEQUENCE: 109
ucagagugag guaguagauu guauaguugu gggguaguga uuuuacccug uucaggagau    60
aacuauacaa ucuauugccu ucccuga                                       87

<210> SEQ ID NO 110
<211> LENGTH: 83
<212> TYPE: RNA
<213> ORGANISM: Homo sapiens

<400> SEQUENCE: 110
ugugggauga gguaguagau uguauaguuu uagggucaua ccccaucuug gagauaacua    60
uacagucuac ugucuuuccc acg                                           83

<210> SEQ ID NO 111
<211> LENGTH: 84
<212> TYPE: RNA
<213> ORGANISM: Homo sapiens

<400> SEQUENCE: 111
aggcugaggu aguaguuugu acaguuugag ggcucaugau accacccggu acaggagaua    60
acuguacagg ccacugccuu gcca                                          84

<210> SEQ ID NO 112
<211> LENGTH: 84
<212> TYPE: RNA
<213> ORGANISM: Homo sapiens

<400> SEQUENCE: 112
cuggcugagg uaguaguuug ugcuguuggu cgggguguga cauugcccgc uggagaaua     60
```

```
acugcgcaag cuacugccuu gcua                                              84

<210> SEQ ID NO 113
<211> LENGTH: 119
<212> TYPE: RNA
<213> ORGANISM: Homo sapiens

<400> SEQUENCE: 113
aggauucugc ucaugccagg gugagguagu aaguuguauu guugugggu agggauauua        60 ggccccaauu agaagauaac uauacaacuu acuacuuucc cuggugugug gcauauuca       119
```